(12) United States Patent
Daly et al.

(10) Patent No.: US 10,453,559 B2
(45) Date of Patent: Oct. 22, 2019

(54) METHOD AND SYSTEM FOR RAPID SEARCHING OF GENOMIC DATA AND USES THEREOF

(71) Applicant: KBIOBOX, LLC, Worcester, MA (US)

(72) Inventors: Kristopher Edward Daly, Worcester, MA (US); Kurtis Phillip Stephens, Worcester, MA (US)

(73) Assignee: KBIOBOX, LLC, Worcester, MA (US)

( * ) Notice: Subject to any disclaimer, the term of this patent is extended or adjusted under 35 U.S.C. 154(b) by 523 days.

(21) Appl. No.: 15/354,707

(22) Filed: Nov. 17, 2016

(65) Prior Publication Data

US 2017/0154154 A1  Jun. 1, 2017

Related U.S. Application Data

(62) Division of application No. 14/341,474, filed on Jul. 25, 2014, now Pat. No. 9,529,891.

(60) Provisional application No. 61/858,600, filed on Jul. 25, 2013.

(51) Int. Cl.

| G16B 50/00 | (2019.01) |
| G06F 16/22 | (2019.01) |
| G06F 16/24 | (2019.01) |
| G06F 16/245 | (2019.01) |
| G06F 16/248 | (2019.01) |
| G06F 16/28 | (2019.01) |
| G06F 16/2455 | (2019.01) |
| G16B 30/00 | (2019.01) |

(52) U.S. Cl.
CPC ............. *G16B 50/00* (2019.02); *G06F 16/22* (2019.01); *G06F 16/2282* (2019.01); *G06F 16/24* (2019.01); *G06F 16/245* (2019.01); *G06F 16/248* (2019.01); *G06F 16/24554* (2019.01); *G06F 16/285* (2019.01); *G16B 30/00* (2019.02)

(58) Field of Classification Search
CPC ........ G16B 50/00; G06F 16/22; G06F 16/245
See application file for complete search history.

(56) References Cited

U.S. PATENT DOCUMENTS

| 6,633,817 B1 | 10/2003 | Walker et al. |
| 6,691,109 B2 | 2/2004 | Bjornson et al. |
| 6,728,960 B1 | 4/2004 | Loomans |
| 7,783,589 B2 | 8/2010 | Hornkvist et al. |
| 8,010,501 B2 | 8/2011 | Bourdoncle et al. |

(Continued)

FOREIGN PATENT DOCUMENTS

WO    WO 2015/013657 A2    1/2015

OTHER PUBLICATIONS

DeSantis, et al., "Simrank: Rapid and Sensitive General-Purpose K-Mer Search Tool," *BMC Ecology*, 11(11):1-8, (2011).

(Continued)

*Primary Examiner* — Loc Tran
(74) *Attorney, Agent, or Firm* — Morse, Barnes-Brown & Pendleton, P.C.; Sean D. Detweiler, Esq.

(57) ABSTRACT

A method, apparatus and system for transforming genomic data into a computer database environment comprising a forward lookup table and a plurality of reverse lookup tables which relate consecutive overlapping reference sequence segments to reference sequences stored in the forward lookup table enables rapid and precise matching of undefined biological sequences with reference sequences.

31 Claims, 18 Drawing Sheets

Specification includes a Sequence Listing.

(56) References Cited

U.S. PATENT DOCUMENTS

| | | | |
|---|---|---|---|
| 8,583,655 B2 | 11/2013 | Elzinga | |
| 9,529,891 B2 | 12/2016 | Daly et al. | |
| 2004/0059721 A1 | 3/2004 | Patzer | |
| 2006/0286566 A1 | 12/2006 | Lapidus et al. | |
| 2008/0222094 A1* | 9/2008 | Cox | G16B 30/00 |
| 2009/0063471 A1 | 3/2009 | Erickson | |
| 2009/0081675 A1* | 3/2009 | Colston, Jr. | C12Q 1/689 |
| | | | 435/6.18 |
| 2009/0270277 A1 | 10/2009 | Glick et al. | |
| 2010/0029498 A1 | 2/2010 | Gnirke et al. | |
| 2012/0004111 A1 | 1/2012 | Colwell et al. | |
| 2014/0200166 A1 | 7/2014 | Van Rooyen et al. | |

OTHER PUBLICATIONS

Ensembl. Ensembl FTP Download [online] Mar. 23, 2009 [retrieved Jan. 9, 2015]. Available on the internet: <URL:https:/ /web.archive.org/web/2009032307 431 0/http:/ /www.ensembl.org/i nfo/data/ftp/i ndex.html>.

Fitch, et al., "Rapid Development of Nucleic Acid Diagnostics," *Proceedings of the IEEE*, 90(11):1708-1720, (2002).

Gnirke, et al., "Solution Hybrid Selection with Ultra-Long Oligo-nucleotides for Massively Parallel Targeted Sequencing," *Nature Biotechnology*, 27:182-189, (2009).

Huang, et al., "Application of a Superword Array in Genome Assembly," *Nucleic Acids Research*, 34(1):201-205, (2006).

Hyatt, et al., "Prodigal: Prokaryotic Gene Recognition and Translation Initiation Site Identification," *BMC Bioinformatics*, 11:119 (2010).

Miller, et al., "Assembly Algorithms for Next-Generation Sequencing Data," *Genomics*, 95:315-327, (2010).

Ning, et al., "SSAHA: A Fast Search Method for Large DNA Databases," *Genome Research*, 11:1725-1729, (2001).

Wu, et al., "Fast and SNP-Tolerant Detection of Complex Variants and Splicing in Short Reads," *Bioinformatics*, 26(7):873-881, (2010).

International Search Report for International Application PCT/US2014/48265, dated Jan. 22, 2015.

* cited by examiner

>gi|263191547|ref|NM_000249.3|Description|Homo sapiens mutL homolog 1
(MLH1), transcript variant 1, mRNA
GAAGAGACCCAGCAACCCACAGAGTTGAGAAATTTGACTGGCATTCAAGCTGTCCAATCAATAGCTGCCGCTGAAGGGTG
GGGCTGGATGGCGTAAGCTACAGCTGAAGGAAGAACGTGAGCACGAGGCACTGAGGTGATTGGCTGAAGGCACTTCCGTT
GAGCATCTAGACGTTTCCTTGGCTCTTCTGGCGCCAAAATGTCGTTCGTGGCAGGGGTTATTCGGCGGCTGGACGAGACA
GTGGTGAACCGCATCGCGGCGGGGGAAGTTATCCAGCGGCCAGCTAATGCTATCAAAGAGATGATTGAGAACTGTTTAGA
TGCAAAATCCACAAGTATTCAAGTGATTGTTAAAGAGGGAGGCCTGAAGTTGATTCAGATCCAAGACAATGGCACCGGGA
TCAGGAAGAAGATCTGGATATTGTATGTGAAAGGTTCACTACTAGTAAACTGCAGTCCTTTGAGGATTTAGCCAGTATT
TCTACCTATGGCTTTCGAGGTGAGGCTTTGGCCAGCATAAGCCATGTGGCTCATGTTACTATTACAACGAAAACAGCTGA
TGGAAAGTGTGCATACAGAGCAAGTTACTCAGATGGAAAACTGAAAGCCCCTCCTAAACCATGTGCTGGCAATCAAGGGA
CCCAGATCACGGTGGAGGACCTTTTTTTACAACATAGCCACGAGGAGAAAAGCTTTAAAAAATCCAAGTGAAGAATATGGG
AAAATTTTGGAAGTTGTTGGCAGGTATTCAGTACACAATGCAGGCATTAGTTTCTCAGTTAAAAAACAAGGAGAGACAGT
AGCTGATGTTAGGACACTACCCAATGCCTCAACCGTGGACAATATTCGCTCCATCTTTGGAAATGCTGTTAGTCGAGAAC
TGATAGAAATTGGATGTGAGGATAAAAACCCTAGCCTTCAAAATGAATGGTTACATATCCAATGCAAACTACTCAGTGAAG
AAGTGCATCTTCTTACTCTTCATCAACCATCGTCTGGTAGAATCAACTTCCTTGAGAAAAGCCATAGAAACAGTGTATGC
AGCCTATTTGCCCAAAAACACACACCCATTCCTGTACCTCAGTTTAGAAATCAGTCCCCAGAATGTGGATGTTAATGTGC
ACCCCACAAAGCATGAAGTTCACTTCCTGCACGAGGAGAGCATCCTGGAGCGGGTGCAGCAGCACATCGAGAGCAAGCTC
CTGGGCTCCAATTCCTCCAGGATGTACTTCACCCAGACTTTGCTACCAGGACTTGCTGGCCCCTCTGGGGAGATGGTTAA
ATCCACACAAGTCTGACCTCGTCTTCTACTTCTGGAAGTAGTGATAAGGTCTATGCCCACCAGATGGTTCGTACAGATT
CCCGGGAACAGAAGCTTGATGCATTTCTGCAGCCTCTGAGCAAACCCCTGTCCAGTCAGCCCCAGGCCATTGTCACAGAG
GATAAGACAGATATTTCTAGTGGCAGGGCTAGGCAGCAAGATGAGGAGATGCTTGAACTCCCAGCCCCTGCTGAAGTGGC
TGCCAAAAATCAGAGCTTGGAGGGGGATACAACAAAGGGGACTTCAGAAATGTCAGAGAAGAGAGGACCTACTTCCAGCA
ACCCCAGAAAGAGACATCGGGAAGATTCTGATGTGGAAATGGTGGAAGATGATTCCCGAAAGGAAATGACTGCAGCTTGT
ACCCCCCGGAGAAGGATCATTAACCTCACTAGTGTTTTGAGTCTCCAGGAAGAAATTAATGAGCAGGGACATGAGGTTCT
CCGGGAGATGTTGCATAACCACTCCTTCGTGGGCTGTGTGAATCCTCAGTGGGCCTTGGCACAGCATCAAACCAAGTTAT
ACCTTCTCAACACCACCAAGCTTAGTGAAGAACTGTTCTACCAGATACTCATTTATGATTTTGCCAATTTTGGTGTTCTC
AGGTTATCGGAGCCAGCACCGCTCTTTGACCTTGCCATGCTTGCCTTAGATAGTCCAGAGAGTGGCTGGACAGAGGAAGA
TGGTCCCAAAGAAGGACTTGCTGAATACATTGTTGAGTTTCTGAAGAAGAAGGCTGAGATGCTTGCAGACTATTTCTCTT
TGGAAATTGATGAGGAAGGGAACCTGATTGGATTACCCCTTCTGATTGACAACTATGTGCCCCCTTTGGAGGGACTGCCT
ATCTTCATTCTTCGACTAGCCACTGAGGTGAATTGGGACGAAGAAAAGGAATGTTTTGAAAGCCTCAGTAAAGAATGCGC
TATGTTCTATTCCATCCGGAAGCAGTACATATCGAGGAGTCGACCCTCTCAGGCCAGCAGAGTGAAGTGCCTGGCTCCA
TTCCAAACTCCTGGAAGTGGACTGTGGAACACATTGTCTATAAAGCCTTGCGCTCACACATTCTGCCTCCTAAACATTTC
ACAGAAGATGGAAATATCCTGCAGCTTGCTAACCTGCCTGATCTATACAAAGTCTTTGAGAGGTGTTAAATATGGTTATT
TATGCACTGTGGGATGTGTTCTTCTTTCTCTGTATTCCGATACAAAGTGTTGTATCAAAGTGTGATATACAAAGTGTACC
AACATAAGTGTTGGTAGCACTTAAGACTTATACTTGCCTTCTGATAGTATTCCTTTATACACAGTGGATTGATTATAAAT
AAATAGATGTGTCTTAACATAA (SEQ ID NO: 7)

*FIG. 16*

Maize Iranian mosaic virus query sequence :
MDTEEPISQDDLDALDGLLQAEEGEEETTDEDGGSMLGGMGDYHLKSALRGFDDMMRHPIFRKEFEKAIVS
FNISHNNMLSQIETMFFMMNDTPHPRRGMLLGDFQQRVVALPHGEDVFDIIHAEICVLHPHLQLSLSVSAVR
DIVRLVMEKVAKDDFASMTWAAAIMIKNFIPAWKKRGKQLLDWPSVNFDAETGYVRMVLEGDLIIYMGSDI
CHEKYPNVRWAPVSYILNGADKLAERYNVRLYSGICDHLSIPDRVSLDDLNRIIDVGDRCLDELGNEGYAVIAS
YEALLAGIIQMRDDDKLIADVGLLRRTTLEEFANTRGGKYLAEWDRMFLNMSAEQVACAHGLYRIWGLPVV
DILGGILKMKEVASVKKCPDESVLKDIGRQFKEMFFTAYHRLHKHYPKSDILPGFPKKSYHEALQNNTSINVK
VVGYVFLDWDYVELKQNFEVPYSWNLVHNLKDKAISPTRKEIYHTLVRRNTIFGAENRRGILKSLKMETVQL
REFLQSVNDDGLPDEDRIIGVYPKERELKIKARLFSLMSFKLRLYIVSTEALLGDKILKYFPQITMSLDMLTMIK
KMFRVSSQTTRGDDSVTVIFNLDFVKWNLQMRKNICHPVFRQLGELFGMKDLYDRTHDLFRTSTIYLCSGEG
ELTADPEYGVNPNGIWAWTGDESGKEGLRQKGWTILTVVAIMLIAKRHNVDVSLMGGGDNQVLGITISGMV
RDSMNGLTDESKGVASKIIKSFTDDLLTTFQDLGLPLKASETWVSDSLFMYNKHMFYKGIPLRSPLKAVSRIF
PLANDSIMTLDNMINNISSGVKAACMKERNGIPLIFLKALSYRRAAEIVLTLHPLVTCFRAPSLPTQGIVMRSS
KKTNVKVTSKQLRNYFACCLTGASIMGTPGTIHVTDMIMRGFPDPLTGHLAFIGALATRIQSVHLRAAVEKMS
HMSINRSIEYAKLVEDPASINHDAPTHGLNELRQMSRDFLMKTTLATNPYLTDLFSLLDRKSESAFYEQLCSA
EELDVKVLHEIAGATLYGYTNGIASRIDQTRTVRALNENEDVMKRMADAEWRYVGYLLARDILTHDLVPDEC
SRVSADRYRLYSWRKPVIGVTVPHPIEMCSVTSQTRTSYMDAVICWSDNVQGNDIYTTMGLGKIYQGSYTKE
RFKATDIAAAYGNEDILSKAVRIQKLINWRYDETSNFADIIRLTLKAITDADTEGFHRSKEEIKGEFDHRRGISG
DISGGIPNFLVTPTSHFSSTTSSWTSHSRGGKNENIHFQSVLINLLYRAMVFRGSSLSTSPVVWYSEERCPHCIV
EIREPDPSRTTPKLDKIPTAPGNPFAFIESINVKLDYHHIVEIHKGNEEEENLINSSWDGTNISCNQEAGLLLFLM
VIGSRQISESFILLMRERVQASEVLQMVINRITLMRRMGLDKQFPVRSTSCLNLLLGTDQNLSRCHDRFGVEIV
SGSWEKGIQLDASFIYRDDLATTGDLHVNVYLQNVPLQLALSHAASRVEVQRCLECCAIISDRVSKRDSPNHL
HWRCPEHMDKDFSPTIVRIHSEKLIKGENIIDGHEFSIPFIDEPVALEVADRTEADLNEWSMPIYMYSAWENI
LPQLYVTMKSAILYTKVTSHVEDEITLINLVARCLNDLRRSMSIYVLSDEFSGTEINNKYDNMRLLPPGIRDTIR
LYEESKHEVCKETALVVNPSSKAPIEGGSLHVIWADNWTQVRETTGHMYHTSVRIASGYCGILEVFDRETPAL
FSLAGSVLSWEKKPIDHERAKIQETPIQLSRVLGCSRLGVRGMRWVMWDSALGLERIIRTLRSKLLSLSSNPG
RADHWKRACQKILKTFMISLYAHVQGDMLERAGSLVGVRVHGALSGITAVHDAASENRLQRRQYIYIKENSK
EGPFILRNRVERRISLMSAVYDLLG    (SEQ ID NO: 8)

*FIG. 17*

METHOD AND SYSTEM FOR RAPID SEARCHING OF GENOMIC DATA AND USES THEREOF

RELATED APPLICATION

This application is a division of, and claims priority to and the benefit of, co-pending U.S. patent application Ser. No. 14/341,474, filed Jul. 25, 2014, which claimed priority to U.S. Provisional Application No. 61/858,600, filed Jul. 25, 2013, for all subject matter contained therein. The disclosures of said applications are hereby incorporated herein by reference in their entirety.

FIELD OF THE INVENTION

The present invention relates to a method for at least one query sequence with at least one reference sequence. In particular, the present invention relates to a computer-implemented method, apparatus and system that provide high-performance, high-speed sequence searches for the precise matching of an undefined biological sequence with one or more known biological sequences.

BACKGROUND

Comparison of unidentified sequences present in a sample (e.g., biological sample) against known sequences can provide useful information about the nature of the sequence. For instance, unidentified nucleic acids and/or proteins present in a biological sample can be sequenced and compared against known sequences to determine the identity and function of the nucleic acid and/or protein, as well as its source (i.e., organism). In this way, a sample containing an unknown mixture of nucleic acids and/or proteins obtained from an individual can be analyzed to determine whether any of the nucleic acids and/or proteins in the sample is foreign.

Existing sequence databases are already vast and continue to grow at an astonishing pace. For example, the human genome project and other similar sequencing initiatives have resulted in an enormous amount of sequence information available in both private and public databases. Sequence similarity searching is used both to compare a single sequence against the sequences in a single database, and is also used to compare many new sequences against multiple databases. Furthermore, sequence alignment and database searches are performed worldwide thousands of times each day. Therefore, the importance of rapidly and accurately comparing new sequence data against such sequence databases is increasing.

Various programs and algorithms are available for performing database sequence similarity searching. For a basic discussion of bioinformatics and sequence similarity searching, see BIOINFORMATICS: A Practical Guide to the Analysis of Genes and Proteins, Baxevanis and Ouellette eds., Wiley-Interscience (1998) and Biological Sequence Analysis: Probabilistic Models of Proteins and Nucleic Acids, Durbin et al., Cambridge University Press (1998). The FASTA program was among the first algorithms used for conducting sequence alignment searching. (Lipman and Pearson, "Rapid and sensitive protein similarity searches," Science, Vol. 227, PP. 1435-1441 (1985); Pearson and Lipman, "Improved tools for biological sequence comparison," Proc. Natl. Acad. Sci., Vol. 85, pp. 2444-2448 (1988)). The FASTA program conducts optimized searches for local alignments using a substitution matrix. The program uses "word hits" to identify possible matches and then performs the more time-consuming optimization search. Another popular algorithm for sequence similarity searching is the BLAST (Basic Local Alignment Search Tool) algorithm, which is employed in programs such as blastp, blastn, blastx, tblastn, and tblastx. (Altschul et al., "Local alignment statistics," Methods Enzymol., Vol. 266, pp. 460-480 (1996); Altschul et al., "Gapped BLAST and PSI-BLAST: A new generation of protein database search programs," Nucl. Acids Res., Vol. 25, pp. 3389-3402 (1997); Karlin et al., "Methods for assessing the statistical significance of molecular sequence features by using general scoring schemes," Proc. Natl. Acad. Sci., Vol. 87, pp. 2264-2268 (1990); Karlin et al., "Applications and statistics for multiple high-scoring segments in molecular sequences," Proc. Natl. Acad. Sci., Vol. 90, pp. 5873-5877 (1993)). The BLAST program identifies segments, optionally with gaps, that are similar between a query sequence and a database sequence, evaluates the statistical significance of all identified matches, and selects only those matches that satisfy a preset significance threshold.

More recently, a DNA sequence searching algorithm referred to as SSAHA reportedly conducts DNA sequences searches as many as three to four orders of magnitude faster than FASTA and BLAST has been described (Mullikin et al, "SSAHA: A Fast Search Method for Large DNA Databases," Genome Research, Vol. 11, pp. 1725-1729 (2001)). The SSAHA algorithm is based on organizing the DNA database into a hash table data structure using a two-bits-per-base binary representation. Sequences in the database are preprocessed by breaking them into consecutive k-tuples of k continuous bases and then using a hash table to store the position of each occurrence of each k-tuple. Searching a query sequence in the database is performed by obtaining from the hash table the "hits" for each k-tuple in the query sequence and then sorting the results to identify exact matches between k-tuples which can be concatenated to identify the sequences in the database which match the query sequence.

However, SSAHA experiences some shortcomings. For example, although the two-bits-per-base representation employed is compact and efficient to process, it has the disadvantage that it is impossible to encode any characters apart from four valid bases (i.e., A, C, G, T). Therefore, while creating hash tables SSAHA requires a user to choose between either ignoring any unrecognized characters entirely and translating unrecognized characters into one of the four bases, resulting in potentially diminished sensitivity. Moreover, SSAHA is ill-equipped for searching protein sequences due to its two-bits-per-base representation. As another example, the SSAHA algorithm's sensitivity is limited by k-tuple size. That is, under no circumstances can the SSAHA algorithm detect a match of less than k consecutive matching base pairs between a query sequence and a subject sequence. Actually, SSAHA requires 2k−1 consecutive matching bases to ensure that the algorithm will register a hit in the matching region. Thus, for a k-tuple size of 15, SSAHA requires 29 consecutive matching bases to ensure that the algorithm will detect a hit in the matching region. In comparison, the default settings of FASTA and BLAST require at least 6 and 12 base pairs, respectively, to detect a match. SSAHA can be adapted to increase sensitivity by allowing one substitution between k-tuples at a cost of approximately 10-fold decrease in search speed. In addition, by modifying the hash table generation code so that k-tuples are hashed base-by-base SSAHA can be adapted to guarantee that any run of k consecutive matching bases will be detected by the algorithm, at a cost of a k-fold increase in CPU time and in the size of the hit list L for a given k. In other words, for SSAHA's ideal k-tuple size of 15, increasing the sensitivity of SSAHA in this manner would result in a 15-fold increase in CPU time. Finally, SSAHA builds hash tables and stores them in active memory (RAM) every time the algorithm runs, which means that the preprocessing step of generating hash tables is performed every time a query is processed, resulting in reduced query processing speed.

SUMMARY

There is a need for a method of organizing genomic data into an efficient format that facilitates rapid searching and matching of undefined biological sequences with known sequences. The present invention is directed toward further solutions to address this need, in addition to having other desirable characteristics. Specifically, the present invention provides a method and system for transforming genomic data into a computer database environment comprising a forward lookup table and a plurality of reverse lookup tables which relate consecutive overlapping reference sequence segments to reference sequences stored in the forward lookup table.

In accordance with one aspect of the present invention, a computer-implemented method of transforming genomic data is provided. In the method, a data processing system can receive genomic data comprising a plurality of reference sequences. The data processing system can construct a forward lookup table and at least one reverse lookup table which relates reference sequence segments stored therein to reference sequences stored in the forward lookup table. The reference sequence segments each include a first string of contiguous characters having a string length equal to a preselected positive integer k and each reference sequence can include a second string of contiguous characters having a string length equal to a positive integer Y. The data processing system can construct the forward lookup table by transforming the genomic data into a plurality of records in the forward lookup table, for example, by parsing the genomic data to create a reference sequence record in the forward lookup table for each reference sequence in the genomic data. The data processing system can construct the at least one reverse lookup table comprises by transforming each reference sequence record in the forward lookup table into a set of Y−k+1 consecutive overlapping reference sequence segments, and storing each reference sequence segment thus transformed in a record in the at least one reverse lookup table. The data processing system can store the forward lookup table and the at least one reverse lookup table in a computer database environment maintained in a non-transitory computer readable storage medium and accessible by the data processing system.

In some implementations, each consecutive overlapping reference sequence segment in the set generated corresponds to the string of k contiguous characters that is obtained by moving incrementally, one character at time, along the second string of contiguous characters, starting at a first offset (I=0), and continuing to a last offset (I=Y−k). In some implementations, each consecutive overlapping reference sequence segment in the set shares k−1 contiguous characters with at least one other consecutive overlapping reference sequence segment in the set. In some implementations, each record in the at least one reverse lookup table contains a reference sequence segment in which the first string of contiguous characters corresponds to k contiguous characters in the second string of contiguous characters, a pointer indicating which reference sequence record contains the reference sequence segment, and an offset (I) indicating a position at which the reference sequence segment begins in the second string of contiguous characters.

In some implementations, the at least one reverse lookup table includes a first reverse lookup table, and n additional reverse lookup tables where n is a positive integer greater than or equal to 2. The preselected positive integer k can differs for each reverse lookup table. In some implementations, the preselected positive integer k is largest for the first reverse lookup table and the preselected positive integer k for each additional reverse lookup table is a divisor of k that decreases as the number of reverse lookup tables increases. In some implementations, the at least one reverse lookup table comprises a first reverse lookup table, and at least a second reverse lookup table. In some implementations, the preselected positive integer k for the first reverse lookup table is 100 and the preselected positive integer k for the second reverse lookup table is 50. In some implementations, the at least one reverse lookup table comprises a first reverse lookup table, a second reverse lookup table, and at least a third reverse lookup table. In some implementations, the preselected positive integer k for the first reverse lookup table is 100, the preselected positive integer k for the second reverse lookup table is 50, and the preselected positive integer k for the third reverse lookup table is 10.

Each record in the forward lookup table can contain information to genomic sequences stored therein. In some implementations, each record in the forward lookup table contains genomic sequence information selected from the group consisting of database of origin, accession number, recommended name, organism name, gene name, protein existence number, and sequence version. In some implementations, the plurality of reference sequences are selected from the group consisting of nucleic acid sequences and protein sequences.

In some implementations, the non-transitory computer readable storage medium is not RAM. In some implementations, the non-transitory computer readable storage medium is selected from the group consisting of at least one hard disk drive, at least one solid state drive, and a combination of the at least one hard disk drive and the at least one solid state drive.

In accordance with another aspect of the present invention, a computer-implemented method of matching at least one query sequence with at least one reference sequence is provided. In the method, a data processing system receives a query including at least one query sequence. The at least one query sequence is a third string of contiguous characters having a string length equal to L. The data processing system selects at least a first reverse lookup table of at least one reverse lookup table in a computer database environment that has the largest preselected positive integer k that is less than or equal to L. The computer database environment is maintained in a non-transitory computer readable storage medium and associated with the data processing system. The computer database environment includes a forward lookup table and the at least one reverse lookup table which relates reference sequence segments stored therein to reference sequences stored in the forward lookup table. The reference sequence segments each include a first string of contiguous characters having a string length equal to a preselected positive integer k which differs for each of the at least one reverse lookup tables and each reference sequence includes a second string of contiguous characters having a string length equal to a positive integer Y. Each of the at least one reverse lookup tables includes a set of Y−k+1 consecutive overlapping reference sequence segments for each reference sequence record stored in the forward lookup table. The data processing system transforms the at least one query sequence into at least a first set of L/k consecutive non-overlapping query sequence segments by partitioning the third string of contiguous characters into L/k consecutive non-overlapping segments where k is equal to the preselected positive integer k for the at least the first reverse lookup table selected. The data processing system queries the at least the first set of L/k consecutive non-overlapping query sequence segments transformed against each set of Y−k+1 consecutive overlapping reference sequence segments in the at least the first reverse lookup table selected for matching reference and query sequence segments. The data processing system outputs at least one reference sequence that matches the at least one query sequence.

In some implementations, each record in the at least one reverse lookup table contains (I) a reference sequence segment in which the first string of contiguous characters corresponds to k contiguous characters in the second string of contiguous characters, (2) a pointer indicating which reference sequence record contains the reference sequence segment, and (3) a first offset ($I_1$) indicating a position at which the reference sequence segment begins in the second string of contiguous characters, and wherein each reference sequence record comprises a column indicating a species of origin associated with the reference sequence.

In the method, the data processing system performs a step of reconstructing each of the matching reference sequence segments for each species of origin to create a fourth string of contiguous characters. The step of reconstructing includes: i) filtering the results of the query by species of origin to create a set of matching reference sequence segments for each species of origin, ii) sorting the set of matching reference sequence segments for each species of origin by the first offset ($I_1$) in ascending order, and concatenating the sorted set of matching reference sequence segments for each species of origin to reconstruct each of the matching reference sequence segments into the fourth string of contiguous characters. The data processing performs a step of determining whether any gaps remain in the fourth string of contiguous characters for each species of origin.

When no gaps are determined to remain in the fourth string of contiguous characters, the data processing system can perform a step of outputting a report comprising the at least one reference sequence that matches the at least one query sequence, wherein the report comprises a histogram for the at least one query sequence indicating the most likely species of origin of the at least one query sequence.

When gaps are determined to remain in the fourth string of contiguous characters for a species of origin, the data processing system can perform a step of determining, for each gap present in the fourth string of contiguous characters, a fifth string of contiguous character gaps having a string length equal to positive integer $k_1$, which is equal to the preselected positive integer k for the at least the first reverse lookup table, and a corresponding second offset ($I_2$) indicating the position in the fourth string of contiguous characters at which the fifth string of contiguous character gaps begins. When the step of determining is complete, the data processing system can perform a step of selecting, at least a second reverse lookup table in the computer database environment that has a preselected positive integer $k_2$ that is less than the preselected positive integer k for the at least the first reverse look lookup table selected. Alternatively, or additionally, the data processing system can perform a sliding matching algorithm, a permutative matching algorithm, or a hybrid matching algorithm to fill the remaining gaps in the fourth string of contiguous characters and outputting a report comprising the at least one reference sequence that matches the at least one query sequence. The report is selected from the group consisting of a histogram for the at least one query sequence indicating the most likely species of origin of the at least one query sequence, an alignment of the at least one query sequence with one or more matching reference sequences in the forward lookup table, and identification of a polymorphism in the at least one query sequence selected from the group consisting of an insertion, a deletion, or a mutation.

In some implementations, the data processing system can perform a step of transforming the at least one query sequence into at least a second set of L/$k_2$ consecutive non-overlapping query sequence segments by partitioning the third string of contiguous characters into L/$k_2$ consecutive non-overlapping segments where $k_2$ is equal to the preselected positive integer $k_2$ for the at least the second reverse lookup table selected. The data processing system can perform a step of partitioning the fifth string of contiguous character gaps into $k_1$/$k_2$ consecutive non-overlapping strings of contiguous character gaps each comprising a sixth string of $k_2$ contiguous character gaps and the corresponding second offset ($I_2$) indicating the position in the fourth string of contiguous characters at which the sixth string of $k_2$ contiguous character gaps begins. The data processing system can then query, for each sixth string of $k_2$ contiguous character gaps in the fourth string of contiguous characters, the at least the second set of L/$k_2$ consecutive non-overlapping query sequence segments generated against each set of Y−k+1 consecutive overlapping reference sequence segments in the at least the second reverse lookup table selected having a first offset ($I_1$) equal to the corresponding second offset ($I_2$), for matching query and reference sequence segments. When matching query and reference sequence segments are returned, the data processing system can perform a step of inserting each matching reference sequence segment obtained into the gaps determined to remain in the fourth string of contiguous characters at the second offset ($I_2$) to fill the gaps and form a seventh string of contiguous characters. Next, the data processing system can perform a step of determining whether any gaps remain in the seventh string of contiguous characters for each species of origin.

When no gaps are determined to remain in the seventh string of contiguous characters, the data processing system can perform step of outputting a report that includes the at least one reference sequence that matches the at least one query sequence. The report can be a histogram for the at least one query sequence indicating the most likely species of origin of the at least one query sequence, an alignment of the at least one query sequence with one or more matching reference sequences in the forward lookup table, and identification of a polymorphism in the at least one query sequence selected from the group consisting of an insertion, a deletion.

When gaps are determined to remain the seventh string of contiguous characters for a species of origin, the data processing step can perform a step of determining, for each gap remaining in the seventh string of contiguous characters, an eighth string of contiguous character gaps having a string length equal to positive integer $k_2$, which is equal to the preselected positive integer k, for the at least the second reverse lookup table, and a corresponding third offset ($I_3$) indicating the position in the seventh string of contiguous characters at which the eighth string of contiguous character gaps begins. The data processing system can then perform a step of selecting, via the data processing system, at least a third reverse lookup table in the computer database environment that has a preselected positive integer $k_3$ that is less than the preselected positive integer $k_2$ for the at least the second reverse look lookup table selected. Alternatively, or additionally, the data processing system can perform a sliding matching algorithm, a permutative matching algorithm, or a hybrid matching algorithm to fill the remaining gaps in the fourth string of contiguous characters, and/or outputting a report comprising the at least one reference sequence that matches the at least one query sequence. The report can include a histogram for the at least one query sequence indicating the most likely species of origin of the at least one query sequence, an alignment of the at least one query sequence with one or more matching reference sequences in the forward lookup table, and identification of a polymorphism in the at least one query sequence selected from the group consisting of an insertion, a deletion, or a mutation.

In some implementations, the data processing system can then perform a step of transforming the at least one query sequence into at least third second set of $L/k_3$ consecutive non-overlapping query sequence segments by partitioning the third string of contiguous characters into $L/k_3$ consecutive non-overlapping segments where $k_3$ is equal to the preselected positive integer $k_3$ for the at least the third reverse lookup table selected. The data processing system can then perform a step of partitioning the eighth string of contiguous character gaps into $k_2/k_3$ consecutive non-overlapping strings of contiguous character gaps each comprising a ninth string of $k_3$ contiguous character gaps and the corresponding third offset ($I_3$) indicating the position in the seventh string of contiguous characters at which each ninth string of $k_3$ contiguous character gaps begins. The data processing system next can perform a step of querying, for each ninth string of $k_3$ contiguous character gaps in the seventh string of contiguous characters, the at least the third set of $L/k_3$ consecutive non-overlapping query sequence segments generated against each set of $Y-k+1$ consecutive overlapping reference sequence segments in the at least the third reverse lookup table selected having a first offset ($I_1$) equal to the corresponding third offset ($I_3$), for matching query and reference sequence segments. When the query is complete, the data processing system can perform a step of inserting each matching reference sequence segment obtained into the gaps determined to remain in the seventh string of contiguous characters at the third offset ($I_3$) to fill gaps and form a tenth string of contiguous characters.

When the tenth string is formed the data processing system can then perform a step of determining whether any gaps remain in the tenth string of contiguous characters for each species of origin. When no gaps are determined to remain in the tenth string of contiguous characters, the data processing system can perform a step of outputting a report that includes the at least one reference sequence that matches the at least one query sequence. The report can include a histogram for the at least one query sequence indicating the most likely species of origin of the at least one query sequence, an alignment of the at least one query sequence with one or more matching reference sequences in the forward lookup table, and identification of a polymorphism in the at least one query sequence selected from the group consisting of an insertion, a deletion, or a mutation. When gaps are determined to remain in the tenth string of contiguous characters, the data processing system can then perform a step of determining, for each gap remaining in the tenth string of contiguous characters, an eleventh string of contiguous character gaps having a string length equal to positive integer $k_4$, which is equal to the preselected positive integer $k_3$ for the at least the third reverse lookup table, and a corresponding fourth offset ($I_4$) indicating the position in the tenth string of contiguous characters at which the eleventh string of contiguous character gaps begins. Alternatively, or additionally, the data processing system can perform a sliding matching algorithm, a permutative matching algorithm, or a hybrid matching algorithm to fill the remaining gaps in the fourth string of contiguous characters, and/or a step of outputting a report comprising the at least one reference sequence that matches the at least one query sequence. The report can include a histogram for the at least one query sequence indicating the most likely species of origin of the at least one query sequence, an alignment of the at least one query sequence with one or more matching reference sequences in the forward lookup table, and identification of a polymorphism in the at least one query sequence selected from the group consisting of an insertion, a deletion, or a mutation.

In some implementations, the sliding matching algorithm comprises determining a gap length G and offset K for each gap remaining in the reconstructed sequence, transforming each gap having length G into two consecutive non-overlapping segments comprising a first overlapping segment comprising an overlapping portion beginning at offset $K=K-\frac{1}{2} G$ and a gap portion beginning at offset K and a second overlapping segment comprising a gap portion beginning at offset $K=K+\frac{1}{2} G$ and an overlapping portion beginning at offset $K=K+G$, transforming the at least one query sequence into two query sequence segments comprising a first query sequence segment comprising G contiguous characters beginning at an offset I corresponding to the offset K of the overlapping portion of the first overlapping segment and a second query sequence segment comprising G contiguous characters beginning at an offset I corresponding to the offset K of the gap portion of the second overlapping segment, querying the first and second query sequences against the reference sequence in the forward lookup table for each species and inserting matching query sequence characters and reference sequence characters into a reconstructed sequence to reduce any gaps remaining in the sequence after gap filling.

In some implementations, the permutative matching algorithm comprises generating all possible characters available to fill the gaps and querying each of the possible characters at each position in the gap against the reverse lookup table comprising a preselected positive integer k that is equal to the gap length. In some implementations, the hybrid matching algorithm comprises a combination of the permutative matching algorithm and the sliding matching algorithm.

In some implementations, the non-transitory computer readable storage medium is not RAM. In some implementations, the non-transitory computer readable storage medium is selected from the group consisting of at least one hard drive, at least one solid state drive, and a combination of at least one hard drive and at least one solid state drive.

In some implementations, the step of querying is always performed without concurrently constructing each of the at least one reverse lookup tables. In some implementations, the data processing system comprises a thread manager configured to concurrently generate the set of $Y-k+1$ consecutive overlapping query sequence segments, query the set of $Y-k+1$ consecutive overlapping query sequence segments against the at least the first set of $L/k$ consecutive non-overlapping reference sequence segments, create a set of matching reference sequence segments for each species of origin. In some implementations, the thread manager is optionally configured to apply the sliding matching algorithm, permutative matching algorithm, and hybrid matching algorithm concurrently with transforming the at least one query sequence into the at least the first set of L/k consecutive non-overlapping query sequence segments, querying the at least the first set of L/k consecutive non-overlapping query sequence segments against each set of Y−k+1 consecutive overlapping reference sequence segments, and creating the set of matching reference sequence segments for each species of origin.

In some implementations, the at least one query sequence comprises a plurality of query sequences comprising n query sequences where n is a positive integer greater than 2, and the thread manager is configured to concurrently transform the plurality of query sequences into sets of consecutive non-overlapping query sequence segments and process the consecutive non-overlapping query sequence segments, and consolidate data correlating to each of the concurrently processed sequences to generate a report selected from the group consisting of a histogram for the at least one query sequence indicating the most likely species of origin of the at least one query sequence, an alignment of the at least one query sequence with one or more matching reference sequences in the forward lookup table, and identification of a polymorphism in the at least one query sequence selected from the group consisting of an insertion, a deletion, or a mutation.

In accordance with yet another aspect of the present invention, a data processing system for matching at least one query sequence with at least one reference sequence is provided. The data processing system includes a computer database environment that includes a forward lookup table and a plurality of reverse lookup tables maintained in a non-transitory computer readable storage medium and configured to relate each set of Y−k+1 consecutive overlapping reference sequence segments stored in records of the plurality of reverse lookup tables to reference sequences stored in records of the forward lookup table. Each set of Y−k+1 consecutive overlapping reference sequence segments includes a first string of contiguous characters having a length equal to a preselected positive integer k which differs for each of the reverse lookup tables. The data processing system also includes a processor circuit. The processor circuit includes a thread manager configured to create a maximum number of threads available in response to receiving a query comprising at least one query sequence comprising a second string of contiguous characters having a length equal to a positive integer L. The maximum number of threads includes a first at least one thread for partitioning the at least one query sequence, a second at least one thread for querying the plurality of reverse lookup tables, and a third at least one thread for gap filling. The maximum number of threads performs asynchronously and in parallel the following steps of transforming, querying, gap filling, and outputting. The processor circuit is configured to perform asynchronously and in parallel a step of transforming, for each query sequence via the first at least one thread, each query sequence of the at least one query sequence into a set of L/k consecutive non-overlapping equally sized query sequence segments each having a string length of k contiguous characters which corresponds to the preselected positive integer k for each reverse lookup table in the computer database environment. The processor circuit is configured to perform asynchronously and in parallel a step of querying, via the second at least one thread, each set of transformed consecutive non-overlapping query sequence segments comprising the string length of k contiguous characters against the corresponding reverse lookup table comprising the preselected positive integer k for each set of Y−k+1 consecutive overlapping reference sequence segments in the corresponding reverse lookup table that match non-overlapping query sequence segments, wherein matching sets of Y−k+1 consecutive overlapping reference sequence segments are sorted by species and preselected positive integer k to create a set of equally sized matching reference sequence segments for each species. The processor circuit is configured to perform asynchronously and in parallel a step of gap filling, for each set of equally sized matching refer sequence segments via the third at least one thread, to match the at least one query sequence with at least one reference sequence in the forward lookup table. The processor circuit is configured to perform asynchronously and in parallel a step of outputting, the at least one reference sequence that matches the at least one query sequence.

BRIEF DESCRIPTION OF THE FIGURES

These and other characteristics of the present invention will be more fully understood by reference to the following detailed description in conjunction with the attached drawings, in which:

FIG. 16 is a nucleic acid sequence used as at least one query sequence in a comparative analysis between an exemplary implementation of a method according to the present invention and BLAST; and FIG. 17 is a protein sequence used as at least one query sequence in an homology analysis to detect homologous viruses in an exemplary implementation of a method according to the present invention.

DETAILED DESCRIPTION

Figure 1:
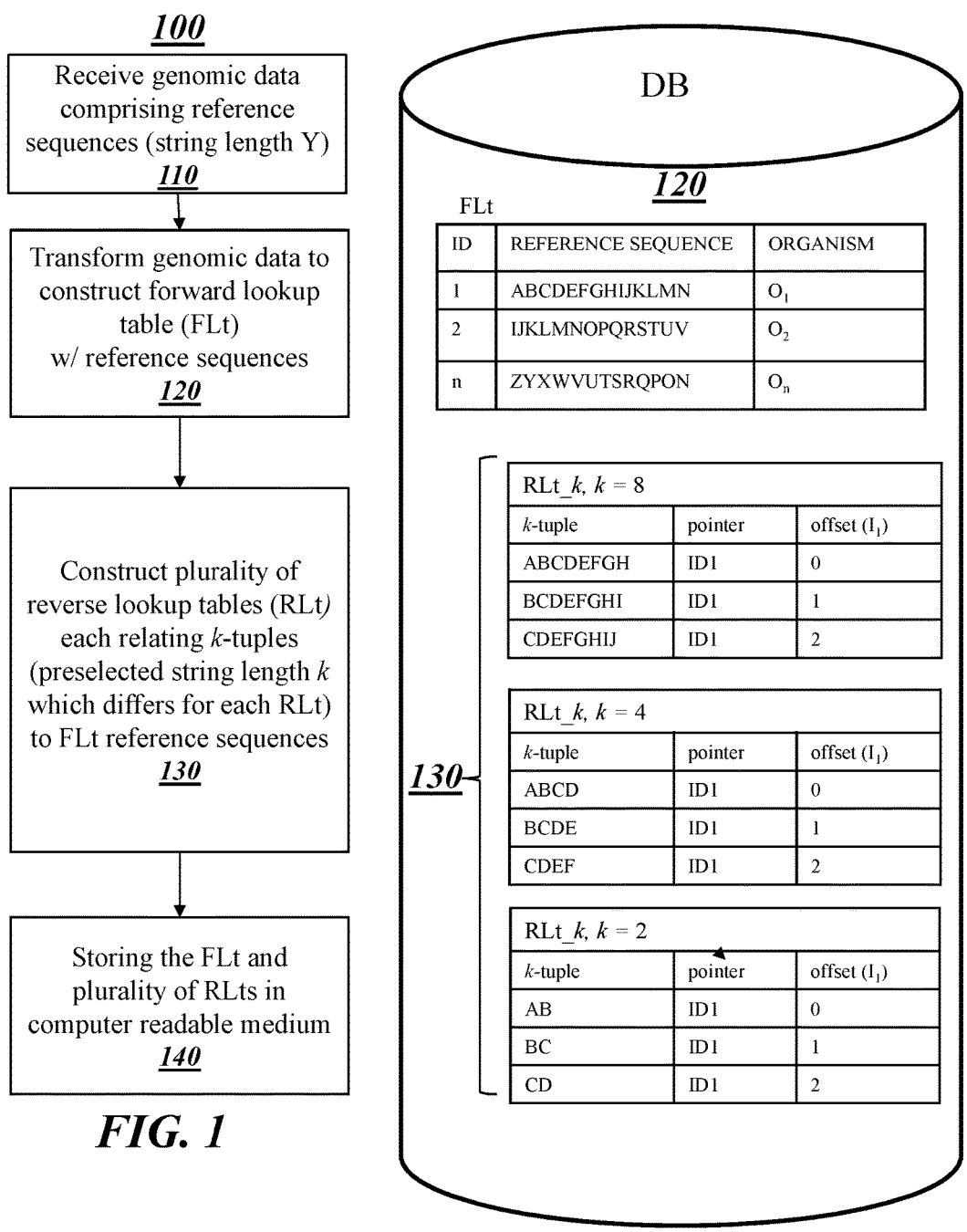
FIG. 1 is a flow chart and schematic illustrating an overview of a process for transforming genomic data into a computer database environment comprising a forward lookup table and a plurality of reverse lookup tables which relate consecutive overlapping reference sequence segments to reference sequences stored in the forward lookup table in accordance with an example embodiment of the present invention.

An illustrative embodiment of the present invention relates to a method, apparatus, and system for transforming genomic data into a computer database environment comprising a forward lookup table and a plurality of reverse lookup tables which relate consecutive overlapping reference sequence segments to reference sequences stored in the forward lookup table. The at least one reverse lookup table is constructed by transforming each reference sequence record in the forward lookup table into a set of Y−k+1 consecutive overlapping reference sequence segments, and storing each reference sequence segment thus transformed in a record in the at least one reverse lookup table. The transformed genomic data in the computer database environment can be used for matching at least one query sequence with at least one reference sequence, for example, for rapid and precise identification of an undefined query sequence. The at least one query sequence is transformed into at least a first set of L/k consecutive non-overlapping query sequence segments by partitioning the third string of contiguous characters into L/k consecutive non-overlapping segments where k is equal to the preselected positive integer k for each consecutive overlapping reference sequence segment in at least a first reverse lookup table. Each transformed set of L/k consecutive non-overlapping query sequence segments is queried against each set of Y−k+1 consecutive overlapping reference sequence segments in the at least the first reverse lookup table for transformed consecutive non-overlapping query sequence segments matching transformed consecutive overlapping reference sequence segments to match the at least one query sequence with at least one reference sequence in the computer database environment. The method, apparatus, and system are configured for implementation in a cascading parallelized fashion, which efficiently and accurately match undefined query sequences with reference sequences by orders of magnitude faster than existing algorithms.

FIGS. 1 through 17, wherein like parts are designated by like reference numerals throughout, illustrate an example embodiments of a method, apparatus and system for transforming genomic data and matching undefined query sequences to reference sequences in the transformed genomic data, according to the present invention. Although the present invention will be described with reference to the example embodiment or embodiments illustrated in the figures, it should be understood that many alternative forms can embody the present invention. One of skill in the art will additionally appreciate different ways to alter the parameters of the embodiment(s) disclosed, such as the size, shape, or type of elements or materials, in a manner still in keeping with the spirit and scope of the present invention.

Referring now to FIG. 1, there is shown a flow chart of and schematic illustrating a computer-implemented method 100 for transforming genomic data into a computer database environment comprising a forward lookup table and a plurality of reverse lookup tables which relate consecutive overlapping reference sequence segments to reference sequences stored in the forward lookup table in accordance with an example embodiment of the present invention. It should be appreciated that references to tables herein can also refer to views or other similar data structures. In an exemplary implementation, method 100 begins with a step 110 of receiving, via a data processing system, genomic data comprising a plurality of reference sequences. As used herein, "reference sequence" refers to a biological sequence deposited in either a publicly available or private database. Reference sequences can include nucleic acid sequences (e.g., any form of DNA or RNA) and protein sequences of any length.

The genomic data received in step 110 is then transformed via the data processing system in step 120 to construct a forward lookup table and at least one reverse lookup table (step 130), which relates reference sequence segments stored therein to reference sequences stored in the forward lookup table 120. The reference sequence segments each comprise a first string of contiguous characters having a string length equal to a preselected positive integer k and each reference sequence comprises a second string of contiguous characters having a string length equal to a positive integer Y. As used herein, the terms "reference sequence segment and "k-tuple" are used interchangeably to refer to a first string of contiguous characters having a string length equal to k corresponding to any one of Y−k+1 possible consecutive overlapping segments of k contiguous characters in the second string of contiguous characters having the string length of k.

Figure 2:
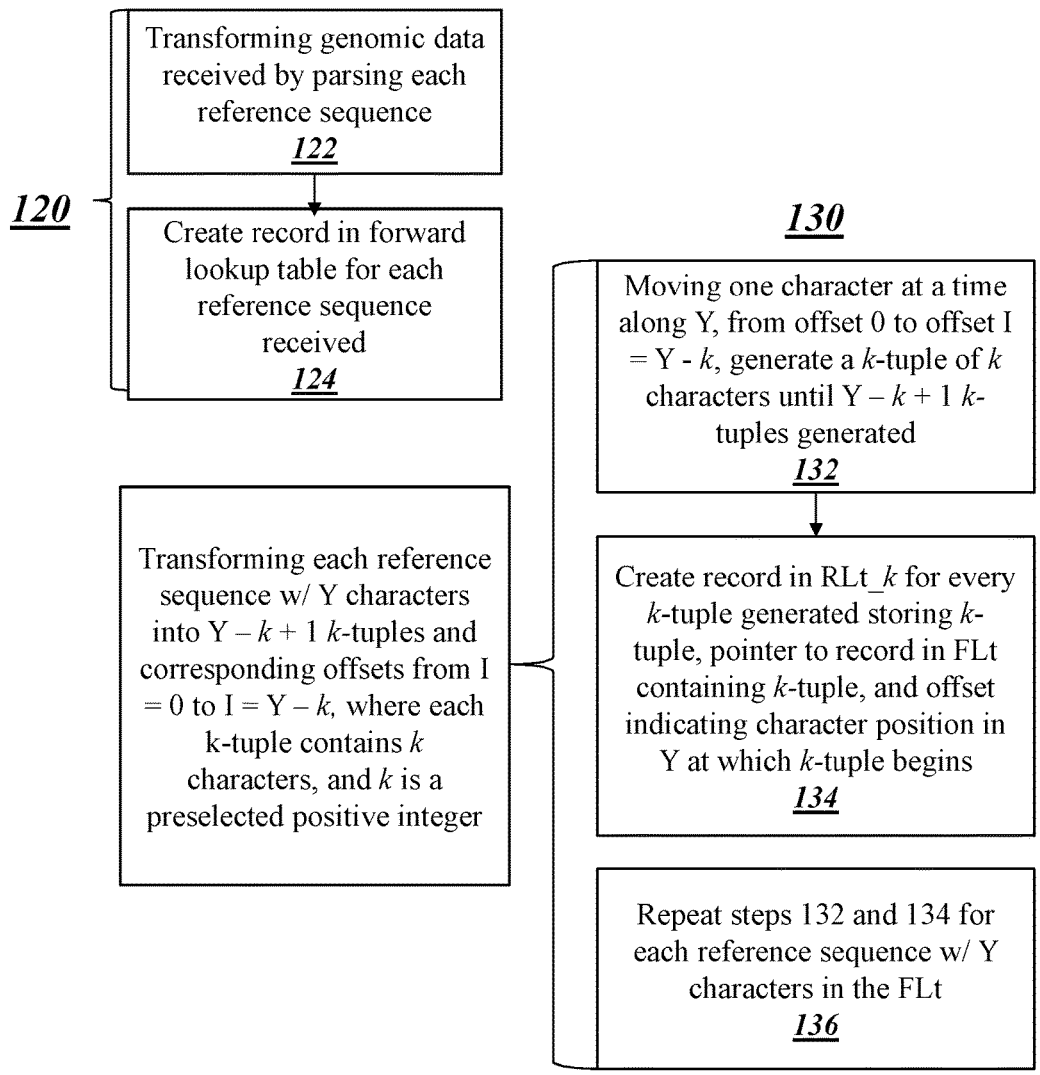
FIG. 2 is a flow chart illustrating elaborating on the process depicted in FIG. 1.

Turning now briefly to FIG. 2, there is shown a flow chart illustrating an exemplary implementation of step 120. In such implementations, constructing the forward lookup table 120 proceeds with a step 122 of transforming the genomic data into a plurality of records in the forward lookup table, for example, by parsing the genomic data and concludes with a step 124 of creating a reference sequence record in the forward lookup table for each reference sequence in the genomic data. It is contemplated that any information pertaining to genomic sequences and their organization can be stored in records of the forward lookup table. In some implementations, each record in the forward lookup table contains genomic sequence information selected from the group consisting of database of origin, accession number, recommended name, organism name, gene name, protein existence number, and sequence version. In some implementations, each record contains taxonomical information pertaining to a reference sequence.

FIG. 2 also shows a flow chart illustrating an exemplary implementation of step 130 constructing the at least one reverse lookup table, for example, by transforming each reference sequence record in the forward lookup table constructed in step 120 into a set of Y−k+1 consecutive overlapping reference sequence segments, and storing each reference sequence segment thus transformed in a record in the at least one reverse lookup table. It should be appreciated that each set of Y−k+1 consecutive overlapping reference sequence segments in a reverse lookup table may vary depending on the values for Y and k, for example each reference sequence comprising Y contiguous characters can be transformed into Y−k+1 k-tuples and corresponding offsets from I=0 to I=Y−k, when each k-tuple contains k contiguous characters and k is the preselected positive integer representing the segment size of each k-tuple in the reverse lookup table.

As shown in FIG. 2, transformation of each reference sequence in the forward lookup table can be achieved by performing steps 132, 134 and 136 for each reverse lookup table comprising a different preselected positive integer k as follows. In step 132, transformation of a reference sequence proceeds by generating a k-tuple of k contiguous characters moving one character at a time along Y, from offset 0 to offset I=Y−k, until Y−k+1 k-tuples have been generated for the reference sequence. Put differently, each transformed consecutive overlapping reference sequence segment in the set corresponds to the string of k contiguous characters that is obtained by moving incrementally, one character at time, along the second string of contiguous characters, starting at a first offset (I=0), and continuing to a last offset (I=Y−k). Next, in step 134, a record is created in the reverse lookup table (RLt_k) for every k-tuple generated in step 132 by transforming the reference sequence into the set of k-tuples. In some implementations, all possible k-tuples for a reference sequence segment are generated in step 132 before creating a record in the reverse lookup table in step 134 for those k-tuples. In other implementations, a record is created in the reverse lookup table in step 134 as each possible k-tuple is generated for a reference sequence segment in step 132. Regardless, in step 136, steps 132 and 134 are repeated for each reference sequence having Y contiguous characters in the forward lookup table until each reference sequence in the forward lookup table is transformed into a set of consecutive overlapping reference sequence segments and stored in the reverse lookup table. Each record thus created in the at least one reverse lookup table contains a reference sequence segment in which the first string of contiguous characters corresponds to k contiguous characters in the second string of contiguous characters, a pointer indicating which reference sequence record contains the reference sequence segment, and an offset (I) indicating a position at which the reference sequence segment begins in the second string of contiguous characters. In addition, each consecutive overlapping reference sequence segment in the set shares k−1 contiguous characters with at least one other consecutive overlapping reference sequence segment in the set.

The method 100, apparatus, and system described herein contemplate using any number of reverse lookup tables desired. The skilled artisan will appreciate that the number of reverse lookup tables may vary depending on the application. In some implementations, the at least one reverse lookup table comprises a first reverse lookup table, and n additional reverse lookup tables where n is a positive integer greater than or equal to 2. Regardless of the number of reverse lookup tables employed, the preselected positive integer k differs for each reverse lookup table. As used herein "preselected positive integer k" means a value of k that is already assigned to each RLt in the computer database. It is to be understood that the preselected positive integer k is assigned to each RLt as each RLt is created during the preprocessing steps of the method. The skilled artisan will appreciated that the preselected positive integer k can differ for each RLt in each database, and each database can be constructed with different numbers of RLts each having a different preselected positive integer k. That is, the preselected positive integer k for any RLt or combination of RLts can vary depending on the application, as will be appreciated by the skilled artisan. Preferably, the preselected positive integer k is largest for the first reverse lookup table and the preselected positive integer k for each additional reverse lookup table is a divisor of k that decreases as the number of reverse lookup tables increases. As used herein, a "divisor" is a number that divides into another without a remainder. For example, the number 10 has four divisors 10, 5, 2, and 1. As an example, when there are five reverse lookup tables comprising preselected positive integers $k_1$, $k_2$, $k_3$, $k_4$ and $k_5$, respectively, the integer values of k for each respective reverse lookup table would be $k_1 > k_2$ (a divisor of $k_1$) $> k_3$ (a divisor of $k_2$) $> k_4$ (a divisor of $k_3$) $> k_5$ (a divisor of $k_4$), e.g., $k_1=1000$, $k_2=500$, $k_3=100$, $k_4=50$, $k_5=10$). In some implementations, the preselected positive integer k is the largest for the first reverse lookup table and the preselected positive integer k for each additional reverse lookup table is a divisor of k that is less than k. As an example, when there are four reverse lookup tables comprising preselected positive integers $k_1$, $k_2$, $k_3$, and $k_4$, respectively, the integer values of k for each respective reverse lookup table would be $k_1 > k_2$ (a divisor of $k_1$) $> k_3$ (a divisor of $k_1$) $> k_4$ (a divisor of $k_3$), e.g., $k_1=1000$, $k_2=500$, $k_3=200$, $k_4=100$).

In some implementations, the at least one reverse lookup table comprises a first reverse lookup table, and at least a second reverse lookup table. In one such implementation, the preselected positive integer k for the first reverse lookup table is 100 and the preselected positive integer k for the second reverse lookup table is 50. In some implementations, the at least one reverse lookup table comprises a first reverse lookup table, a second reverse lookup table, and at least a third reverse lookup table. In one such implementation, the preselected positive integer k for the first reverse lookup table is 100, the preselected positive integer k for the second reverse lookup table is 50, and the preselected positive integer k for the third reverse lookup table is 10. Of course, it will be appreciated by the skilled artisan that the preselected positive integer k may differ depending on the application, as the integer k may tend to increase for larger query sequences and decrease for smaller query sequences (e.g., fragments).

Figure 10:
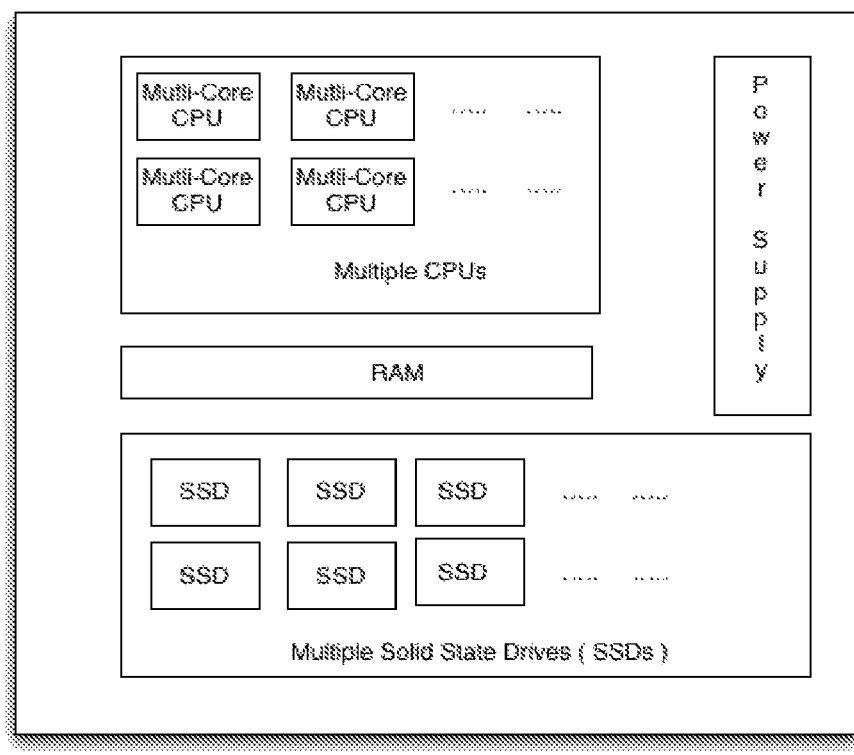
FIG. 10 is a schematic illustrating hardware components in accordance with an example embodiment of the present invention.

Turning back briefly to FIG. 1, when transformation of the genomic data into the forward lookup table and the at least one reverse lookup table is complete, step 140 begins. In step 140, the forward lookup table and the at least one reverse lookup table comprising the transformed genomic data are stored in a computer database environment maintained in a non-transitory computer readable storage medium and accessible by the data processing system. It is contemplated that any non-transitory computer readable storage medium which is accessible by the data processing system can be used. In some implementations, the non-transitory computer readable storage medium is selected from the group consisting of at least one hard disk drive, at least one solid state drive, and a combination of the at least one hard disk drive and the at least one solid state drive, each of which have persistent memory stores. It is contemplated that any equivalent persistent memory hard disk or solid state drive can be used. In some implementations, the at least one solid state drive comprises one or more PCIe cards. An exemplary implementation of such hardware of use in the present invention is shown in FIG. 10, which is described in more detail in Example 1 below. In some implementations, the non-transitory computer readable storage medium is not Random Access Memory (RAM) which is not persistent memory.

Figure 3:
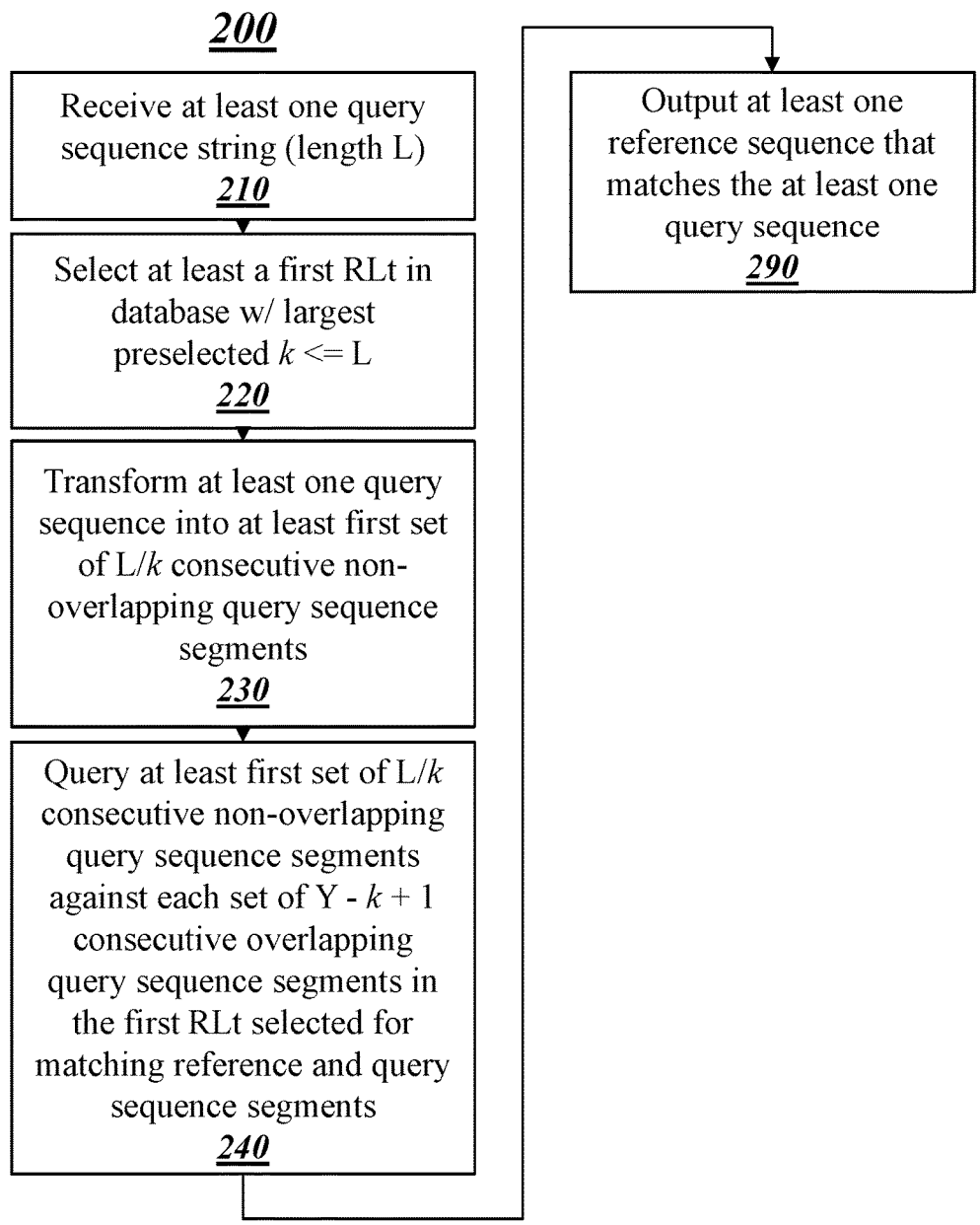
FIG. 3 is a flow chart illustrating an overview of a process for matching at least one query sequence with at least one reference sequence in accordance with an example embodiment of the present invention.

Turning now to FIG. 3, there is shown a flowchart illustrating an exemplary implementation of a computer-implemented method 200 of matching at least one query sequence with at least one reference sequence. In an exemplary implementation, process 200 begins with a step 210 of receiving, via a data processing system, a query comprising at least one query sequence comprising a third string of contiguous characters having a string length equal to L. The "third string of contiguous characters" can refer to a single query sequence, for example, when only one at least one query sequence is received in step 210, or multiple different query sequences, for example, when a plurality of at least one query sequences are received in step 210.

It is contemplated that L can be any positive integer, as the method 200 is capable of processing query sequences of any length L, regardless of how long the sequences are. It is also contemplated that the at least one query sequence can include a nucleic acid sequence (e.g., any form of deoxyribonucleic acid (DNA) or ribonucleic acid (RNA), e.g., mRNA, shRNA, siRNA, antisense oligonucleotides, etc.) and a protein sequence, i.e., the third string of contiguous characters can include bases adenine (A), cytosine (C), guanine (G), thiamine (T), uracil (U), as well as amino acid residues alanine (A), arginine (R), asparagine (N), aspartic acid (D), cysteine (C), glutamic acid (E), glutamine (Q), glycine (G), histidine (H), isoleucine (I), leucine (L), lysine (K), methionine (M), phenylalanine (F), proline (P), serine (S), threonine (T), tryptophan (W), tyrosine (Y), and valine (V). The at least one query sequence can include any number of query sequences or sets of query sequences, e.g., a number N, where N is positive integer. The at least one query sequence can be a complete sequence or a partial sequence, e.g., a fragment of a complete nucleic acid or protein sequence, e.g., 1%, 3%, 5%, 7%, 10%, 15%, 20%, 30%, 33%, 35%, 40%, 42%, 46%, 50%, 60%, 66%, 72%, 75%, 80%, 88%, 90%, 91%, 92%, 93%, 94%, 95%, 98%, or 99% or more of the complete nucleic acid or protein sequence. The at least one query sequence can include a mutation (e.g., single nucleotide polymorphism), insertion, or deletion with respect to a reference sequence. The at least one query sequence can comprise a set of multiple query sequences to be aligned with each other. In some implementations, the at least one query sequence can comprise at least one gap, e.g., an unknown nucleotide or amino acid residue, for example, represented by one or more Xs or Ns. In such implementations, each RLt_k comprising sequences with one or more Xs or Ns is expanded, e.g., a sequence ACTNG, in which N represents any nucleotide is treated as each of the following sequences ACTAG, ACTCG, ACTGG, ACTTG, and ACTUG, which are each stored in the RLt_k. In some implementations, the at least one query sequence can comprise an entire chromosome (e.g., human or bacterial chromosome) or genome (e.g., human or virus genome). In some implementations, the at least one query sequence can comprise a library of sequences.

When at least one query sequence is received in step 210, the method 200 then performs a step 220 of selecting, via the data processing system, at least a first reverse lookup table of at least one reverse lookup table in a computer database environment that has the largest preselected positive integer k that is less than or equal to L. Selecting the reverse lookup table having the largest k value that is less than or equal to L maximizes efficiency of processing by avoiding the case where the query sequence segment size is larger than the length of the query sequence itself. In some implementations, step 220 occurs in parallel with step 210 as additional at least one query sequences are received and processed. It should be appreciated that the computer database environment used to perform method 200 can be the same as the computer database environment used to perform method 100, e.g., the computer database environment can be maintained in a non-transitory computer readable storage medium and associated with the data processing system, wherein the computer database environment comprises a forward lookup table and the at least one reverse lookup table which relates reference sequence segments stored therein to reference sequences stored in the forward lookup table. As noted above, the reference sequence segments each comprise a first string of contiguous characters having a string length equal to a preselected positive integer k which differs for each of the at least one reverse lookup tables and each reference sequence comprises a second string of contiguous characters having a string length equal to a positive integer Y, and each of the at least one reverse lookup tables comprises a set of Y−k+1 consecutive overlapping reference sequence segments for each reference sequence record stored in the forward lookup table.

When the at least the first reverse lookup table is selected, the method 200 then proceeds to a step 230 of transforming, via the data processing system, the at least one query sequence into at least a first set of L/k consecutive non-overlapping query sequence segments, for example, by partitioning the third string of contiguous characters into L/k consecutive non-overlapping segments where k is equal to the preselected positive integer k for the at least the first reverse lookup table selected in step 220. Transformation step 230 is performed on each of the at least one query sequences and proceeds until each of the at least one query sequences is transformed into consecutive non-overlapping sequence segments. The method 200 is capable of performing transformation step 230 in parallel with steps 210 and 220, for example, by assigning threads to perform each of the steps for multiple at least one query sequences.

When the at least one query sequence is transformed into the at least the first set of query sequence segments in step 230, the method then proceeds to a step 240 of querying, via the data processing system, the at least the first set of L/k consecutive non-overlapping query sequence segments transformed in step 230 against each set of Y−k+1 consecutive overlapping reference sequence segments in the at least the first reverse lookup table selected in step 220 for matching reference and query sequence segments. Querying in step 240 can proceed in parallel for each additional reverse lookup table in the computer database environment, and the results can be consolidated and output, as will be explained in further detail below. When a step 240 of querying is complete for each of set of query sequence segments transformed in step 230, the method 200 may proceed to a step 290 of outputting, via the data processing system, at least one reference sequence that matches the at least one query sequence. The at least one reference sequence that matches the at least one query sequence can be output in the form of a report. The report can be formatted in a variety of ways, for example, depending on the application and analysis desired. For example, for species identification the report can comprise a histogram indicating the most likely species of origin from which the at least one query sequence is derived. In some implementations, the report can comprise an alignment of the at least one query sequence with at least one reference sequence. In some implementations, the report can comprise a mutation analysis, for example, showing a mutation, an insertion, or deletion in the at least one query sequence compared to at least one reference sequence.

Figure 4:
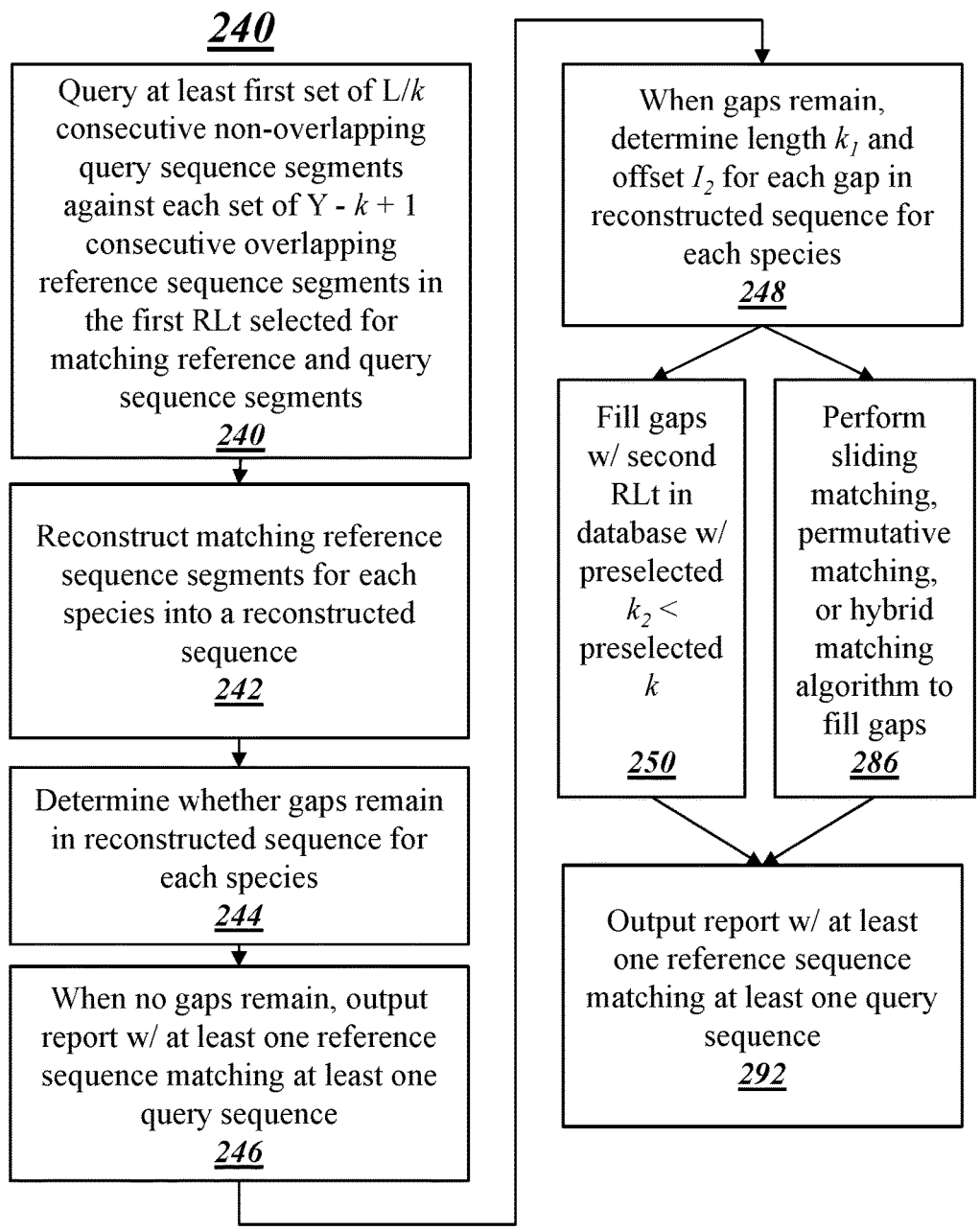
FIGS. 4, 5 and 6 are flow charts elaborating on the process depicted in FIG. 3.

Referring now to FIG. 4, there is shown an exemplary implementation of how method 200 processes results obtained by querying for matching reference and query sequence segments in step 240 using the first at least one reverse lookup table selected in step 220. As noted above, each record in the at least one reverse lookup table contains (1) a reference sequence segment in which the first string of contiguous characters corresponds to k contiguous characters in the second string of contiguous characters, (2) a pointer indicating which reference sequence record contains the reference sequence segment, and (3) a first offset ($I_1$) indicating a position at which the reference sequence segment begins in the second string of contiguous characters, and wherein each reference sequence record comprises a column indicating a species of origin associated with the reference sequence. It is to be understood that the pointer for each reference sequence segment is used to identify the organism (e.g., species of origin) in which the reference sequence segment is found and the offset is used to indicate the precise location in the reference sequence where the reference sequence segment begins. Thus the pointer and offset can be used to reconstruct matching query and reference sequence segments into reconstructed sequences for comparison between the at least one query sequence and at least one reference sequences.

Accordingly, when the results of the query performed in step 240 are returned, the method 200 proceeds to a step 242 of reconstructing each of the matching reference sequence segments for each species of origin to create a fourth string of contiguous characters (i.e., the reconstructed sequence for comparison between the at least one query sequence and at least one query sequence). The "fourth string of contiguous characters" can refer to a single reconstructed sequence, for example, when only a single set of matching reference sequence segments is returned for a single species, or multiple reconstructed sequences, for example, when multiple sets of matching reference sequence segments are returned for multiple species. To create the fourth string of contiguous characters the method 200 proceeds by filtering the results of the query by species of origin to create a set of matching reference sequence segments for each species of origin. This can be accomplished using the pointer to refer to the record in the forward lookup table that contains the matching reference sequence segment, which also indicates the organism. When the set of matching reference sequence segments is created for each species of origin, the method proceeds by sorting the set of matching reference sequence segments for each species of origin by the first offset ($I_1$) in ascending order, followed by concatenating the sorted set of matching reference sequence segments for each species of origin to reconstruct each of the matching reference sequence segments into the fourth string of contiguous characters.

When the fourth string of contiguous characters is created in step 242, the method 200 proceeds to a step 244 of determining whether any gaps remain in the fourth string of contiguous characters for each species of origin. When no gaps are determined in step 244 to remain in the fourth string of contiguous characters, the method 200 proceeds to a step 246 of outputting a report comprising the at least one reference sequence that matches the at least one query sequence. In such instance, the report comprises a histogram for the at least one query sequence indicating the most likely species of origin of the at least one query sequence. It should be appreciated that in some instances the report is generated even when gaps are determined in step 244 to remain in the fourth string of contiguous characters. For example, it may be desirable to output a histogram when a threshold percentage of the fourth string of contiguous characters is determined to be free of gaps. In some implementations, the report is output when the fourth string of contiguous characters is at least 80%, or at least 90% or more gap free as a measure of total individual character gaps in the string relative to the total overall characters in the string. When gaps are determined in step 244 to remain in the fourth string of contiguous characters for a species of origin, the method 200 proceeds to a step 248 of determining, for each gap present in the fourth string of contiguous characters, a fifth string of contiguous character gaps having a string length equal to positive integer k, which is equal to the preselected positive integer k for the at least the first reverse lookup table, and a corresponding second offset ($I_2$) indicating the position in the fourth string of contiguous characters at which the fifth string of contiguous character gaps begins. The "fifth string of contiguous characters" can refer to a gap in a single reconstructed sequence, for example, when only one a single reconstructed sequence is created in step 242 for a single species, or a gap in multiple different reconstructed sequences, for example, when multiple sequences are created in step 242 for multiple species. Step 248 can also be referred to as a "gap characterization step" in which the size and location of gaps remaining in the reconstructed sequence are characterized so that they can be eventually be filled, for example, by transforming a gap of $k_1$ contiguous characters into multiple smaller gaps of $k_2$ contiguous characters where k, equals the preselected positive integer k for the reverse lookup table used to return the matching reference sequence segments that used to form the fifth string of contiguous characters, and $k_2$ is equal to preselected positive integer k for the reverse lookup table having the next largest k value which will be used to formulate queries to fill the multiple smaller gaps created. In this way, each of the larger gaps is transformed into multiple smaller gaps that can be filled by querying the reverse lookup table having the next largest k value for matching query and reference sequence segments, and reconstructing the sequence using those matching segments, and determining whether any gaps remain. This gap filling and gap characterization process can be iterated for each reverse lookup table available in the computer database environment until either no gaps remain or all of the reverse lookup tables is exhausted and gaps remain, at which point a matching algorithm can be applied to reduce any remaining gaps. It should be appreciated, however, that a matching algorithm can also be employed after the first at least one reverse lookup table is queried, as will be explained in further detail below.

When the gap characterization step 248 is complete, method 200 may proceed to step 250 of gap filling using a second at least one reverse lookup table having a preselected $k_2$ that is less than the preselected k, for the first at least one reverse lookup table selected in step 220, step 286 of performing a sliding matching algorithm, a permutative matching algorithm, or a hybrid matching algorithm, or both steps 220 and 286, followed by a step 292 of outputting a report, as shown in FIG. 4. In step 286, method 200 proceeds by performing a sliding matching algorithm, a permutative matching algorithm, or a hybrid matching algorithm to fill the remaining gaps in the fourth string of contiguous characters. When the sliding matching algorithm, permutative matching algorithm, or hybrid matching algorithm is complete, method 200 proceeds to a step 292 of outputting a report comprising the at least one reference sequence that matches the at least one query sequence. In such a step, the report can include a histogram for the at least one query sequence indicating the most likely species of origin of the at least one query sequence, an alignment of the at least one query sequence with one or more matching reference sequences in the forward lookup table, and identification of a polymorphism in the at least one query sequence selected from the group consisting of an insertion, a deletion, or a mutation.

Figure 5:
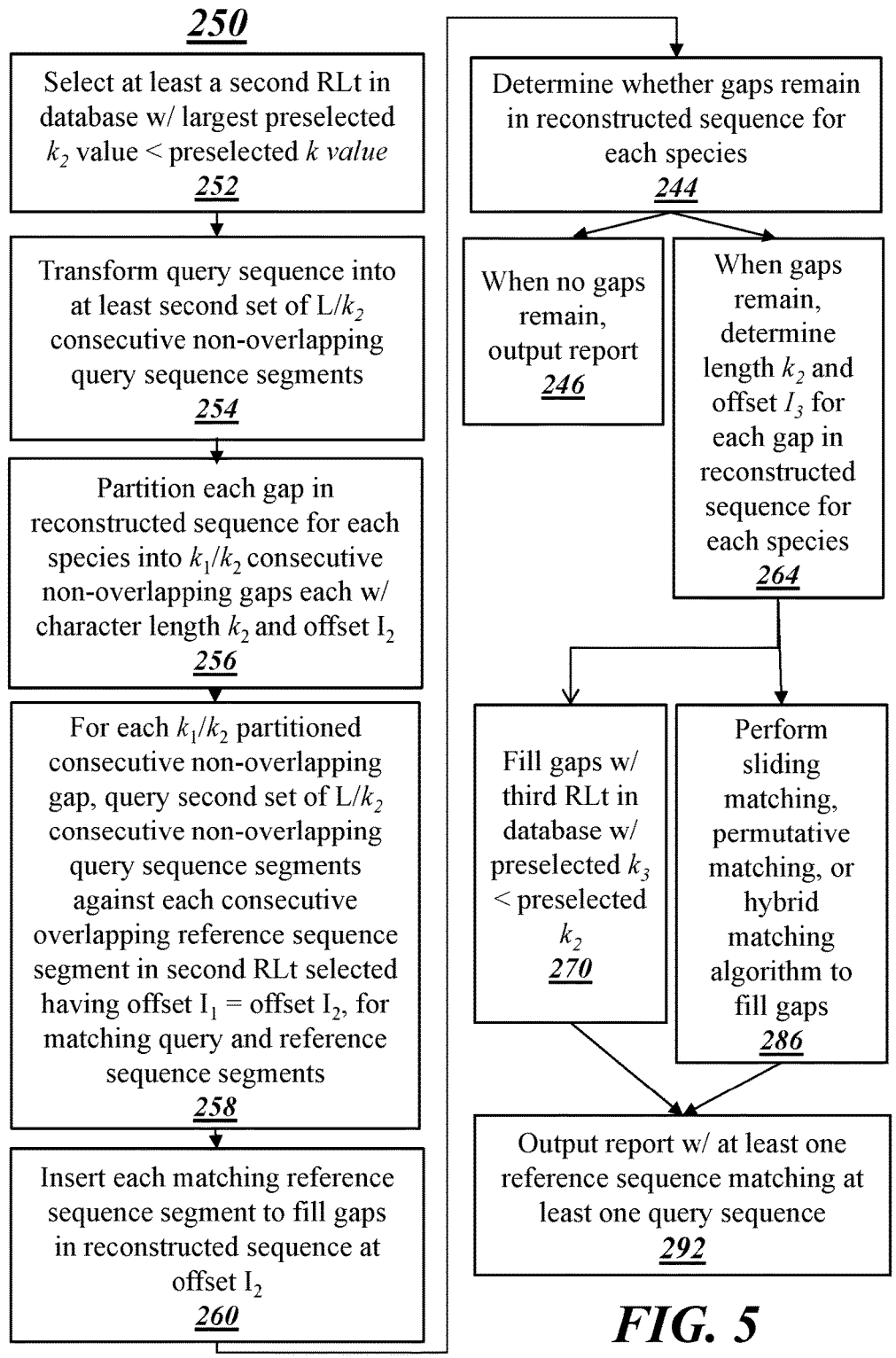

Turning now to FIG. 5, there is shown a flowchart illustrating an exemplary implementation of gap filling using a second at least one reverse lookup table. As shown in FIG. 5, the data processing system in step 252 selects at least a second reverse lookup table in the computer database environment that has a preselected positive integer $k_2$ that is less than the preselected positive integer k for the at least the first reverse look lookup table selected in step 220. When the at least the second reverse lookup table is selected in step 252, method 200 proceeds to a step 254 of transforming, via the data processing system, the at least one query sequence into at least a second set of $L/k_2$ consecutive non-overlapping query sequence segments by partitioning the third string of contiguous characters into $UL/k_2$ consecutive non-overlapping segments where $k_2$ is equal to the preselected positive integer $k_2$ for the at least the second reverse lookup table selected in step 252. When step 252 is complete, method 200 proceeds to a step 256 of partitioning the fifth string of contiguous character gaps into $k_1/k_2$ consecutive non-overlapping strings of contiguous character gaps each comprising a sixth string of $k_2$ contiguous character gaps and the corresponding second offset ($I_2$) indicating the position in the fourth string of contiguous characters at which the sixth string of $k_2$ contiguous character gaps begins. The "sixth string of contiguous characters" can refer to a gap in a single reconstructed sequence, for example, when only one a single reconstructed sequence is created in step 242 for a single species, or a gap in multiple different reconstructed sequences, for example, when multiple sequences are created in step 242 for multiple species. When the sixth string is created in step 256, method 200 proceeds to a step 258 of querying, via the data processing system, for each sixth string of $k_2$ contiguous character gaps in the fourth string of contiguous characters, the at least the second set of $L/k_2$ consecutive non-overlapping query sequence segments generated against each set of $Y-k_2+1$ consecutive overlapping reference sequence segments in the at least the second reverse lookup table selected having a first offset ($I_1$) equal to the corresponding second offset ($I_2$), for matching query and reference sequence segments. When the matching query and reference sequence segments are returned in step 258, method 200 proceeds to a step 260 of inserting each matching reference sequence segment obtained into the gaps determined to remain in the fourth string of contiguous characters at the second offset ($I_2$) to fill the gaps and form a seventh string of contiguous characters (i.e., a reconstructed sequence comprising the matching reference sequence segments from the results of the querying the first at least one reverse lookup table for each species of origin combined with the matching reference sequence segments from the results of querying the second at least one reverse lookup table for each of the same species of origin). The "seventh string of contiguous characters" can refer to a single reconstructed sequence, for example, when only a single set of matching reference sequence segments is returned for a single species, or multiple reconstructed sequences, for example, when multiple sets of matching reference sequence segments are returned for multiple species.

When the seventh string of contiguous characters is created in step 260, method 200 proceeds to a step 244 of determining whether any gaps remain in the seventh string of contiguous characters for each species of origin. When no gaps are determined in step 244 to remain in the seventh string of contiguous characters, method 200 proceeds to a step 246 of outputting a report comprising the at least one reference sequence that matches the at least one query sequence. When gaps are determined in step 244 to remain the seventh string of contiguous characters for a species of origin, method 200 proceeds to a step 264 of determining, for each gap remaining in the seventh string of contiguous characters, an eighth string of contiguous character gaps having a string length equal to positive integer $k_2$, which is equal to the preselected positive integer k, for the at least the second reverse lookup table, and a corresponding third offset ($I_3$) indicating the position in the seventh string of contiguous characters at which the eighth string of contiguous character gaps begins. The "eighth string of contiguous characters" can refer to a gap in a single reconstructed sequence, for example, when only one a single reconstructed sequence is created in step 242 for a single species, or a gap in multiple different reconstructed sequences, for example, when multiple sequences are created in step 242 for multiple species. Like step 248, step 264 can also be referred to as a "gap characterization step."

When the gap characterization step 264 is complete, method 200 may proceed to a step 270 of gap filling using a third at least one reverse lookup table having a preselected positive integer $k_3$ that is less than the preselected positive integer $k_2$ for the second at least one reverse lookup table selected in step 252, step 286 of performing a sliding matching algorithm, a permutative matching algorithm, or a hybrid matching algorithm, or both steps 220 and 286, followed by step 292 in FIG. 5. In step 286, method 200 proceeds by performing a sliding matching algorithm, a permutative matching algorithm, or a hybrid matching algorithm to fill the remaining gaps in the fourth string of contiguous characters. When the sliding matching algorithm, permutative matching algorithm, or hybrid matching algorithm is complete, method 200 proceeds to a step 292 of outputting a report comprising the at least one reference sequence that matches the at least one query sequence. In such a step, the report can include a histogram for the at least one query sequence indicating the most likely species of origin of the at least one query sequence, an alignment of the at least one query sequence with one or more matching reference sequences in the forward lookup table, and identification of a polymorphism in the at least one query sequence selected from the group consisting of an insertion, a deletion, or a mutation.

Figure 6:
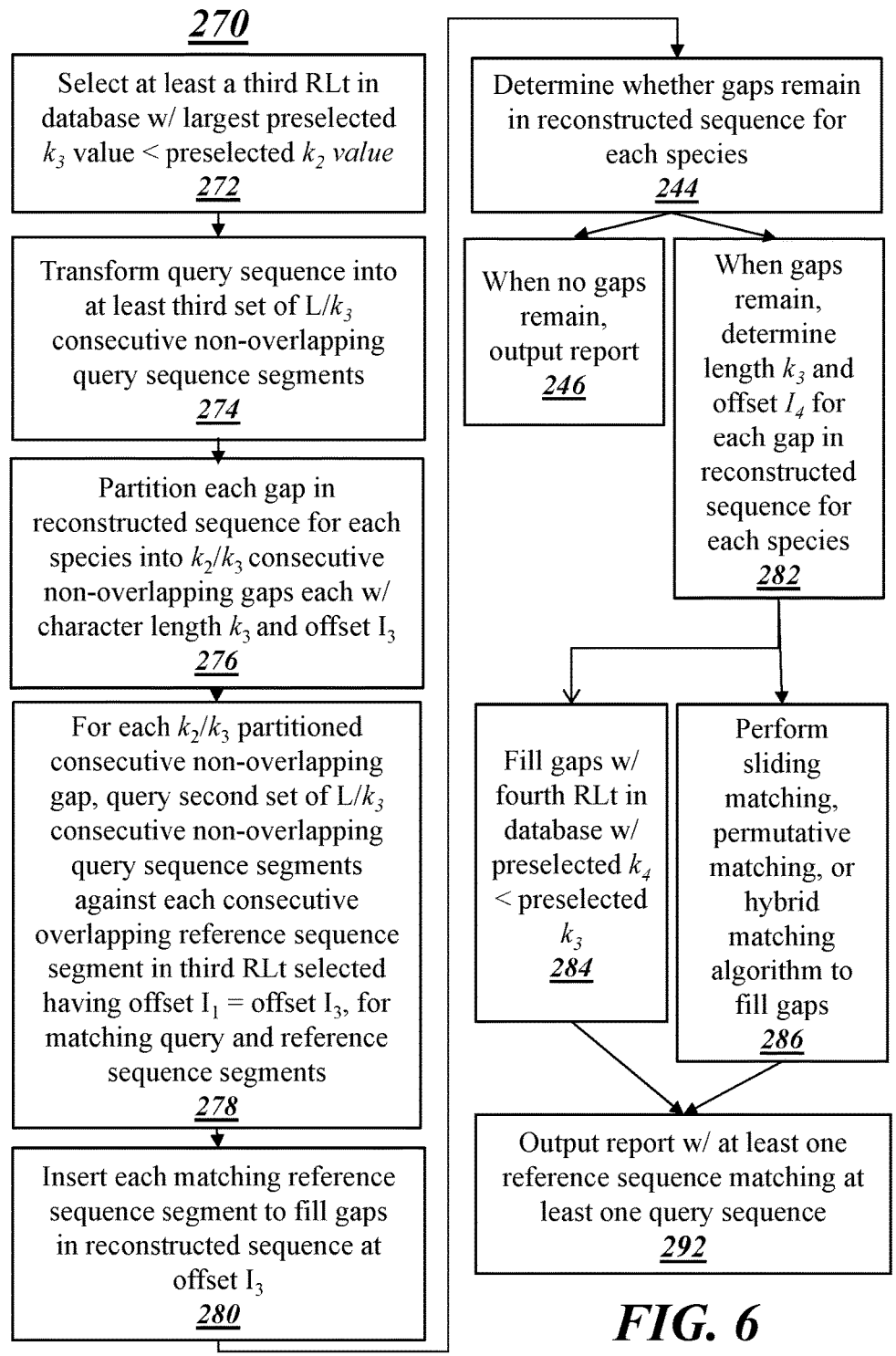

Turning now to FIG. 6, there is shown a flowchart illustrating an exemplary implementation of gap filling using the third at least one reverse lookup table. As shown in FIG. 6, the data processing system in step 272 selects at least a third reverse lookup table in the computer database environment that has a preselected positive integer $k_3$ that is less than the preselected positive integer $k_2$ for the at least the second reverse look lookup table selected in step 252. When the at least the second reverse lookup table is selected in step 272, method 200 proceeds to a step 274 of transforming, via the data processing system, the at least one query sequence into at least third second set of $L/k_3$ consecutive non-overlapping query sequence segments, for example, by partitioning the third string of contiguous characters into $UL/k_3$ consecutive non-overlapping segments where $k_3$ is equal to the preselected positive integer $k_3$ for the at least the third reverse lookup table selected. When step 272 is complete, method 200 proceeds to a step 276 of partitioning the eighth string of contiguous character gaps into $k_2/k_3$ consecutive non-overlapping strings of contiguous character gaps each comprising a ninth string of $k_3$ contiguous character gaps and the corresponding third offset ($I_3$) indicating the position in the seventh string of contiguous characters at which each ninth string of $k_3$ contiguous character gaps begins. The "ninth string of contiguous characters" can refer to a gap in a single reconstructed sequence, for example, when only one a single reconstructed sequence is created in step 260 for a single species, or a gap in multiple different reconstructed sequences, for example, when multiple sequences are created in step 260 for multiple species. When the ninth string is created in step 276, method 200 proceeds to a step 278 of querying, via the data processing system, for each ninth string of $k_3$ contiguous character gaps in the seventh string of contiguous characters, the at least the third set of $L/k_3$ consecutive non-overlapping query sequence segments generated against each set of $Y-k_3+1$ consecutive overlapping reference sequence segments in the at least the third reverse lookup table selected having a first offset ($I_1$) equal to the corresponding third offset ($I_2$), for matching query and reference sequence segments. When the matching query and reference sequence segments are returned in step 278, method 200 proceeds to a step 280 of inserting each matching reference sequence segment obtained into the gaps determined to remain in the seventh string of contiguous characters at the third offset ($I_3$) to fill gaps and form a tenth string of contiguous characters. (i.e., a reconstructed sequence comprising the matching reference sequence segments from the results of the querying the first at least one reverse lookup table for each species of origin combined with the matching reference sequence segments from the results of querying the second and third at least one reverse lookup table for each of the same species of origin). The "tenth string of contiguous characters" can refer to a single reconstructed sequence, for example, when only a single set of matching reference sequence segments is returned for a single species, or multiple reconstructed sequences, for example, when multiple sets of matching reference sequence segments are returned for multiple species.

When the tenth string of contiguous characters is created in step 280, method 200 proceeds to a step 244 of determining whether any gaps remain in the tenth string of contiguous characters for each species of origin. When no gaps are determined in step 244 to remain in the tenth string of contiguous characters, method 200 proceeds to a step 246 of outputting a report comprising the at least one reference sequence that matches the at least one query sequence. When gaps are determined in step 244 to remain the tenth string of contiguous characters for a species of origin, method 200 proceeds to a step 282 of determining, for each gap remaining in the tenth string of contiguous characters, an eleventh string of contiguous character gaps having a string length equal to positive integer $k_4$, which is equal to the preselected positive integer $k_3$ for the at least the third reverse lookup table, and a corresponding fourth offset ($I_4$) indicating the position in the tenth string of contiguous characters at which the eleventh string of contiguous character gaps begins. The "eleventh string of contiguous characters" can refer to a gap in a single reconstructed sequence, for example, when only one a single reconstructed sequence is created in step 280 for a single species, or a gap in multiple different reconstructed sequences, for example, when multiple sequences are created in step 280 for multiple species. Like steps 248 and 264, step 282 can also be referred to as a "gap characterization step."

When the gap characterization step 280 is complete, method 200 may proceed to a step 284 of gap filling using a fourth at least one reverse lookup table having a preselected positive integer $k_4$ that is less than the preselected positive integer $k_3$ for the third at least one reverse lookup table selected in step 272, step 286 of performing a sliding matching algorithm, a permutative matching algorithm, or a hybrid matching algorithm, or both steps 220 and 286, followed by step 292 in FIG. 6. The steps in method 200 can be repeated for each reverse lookup table in the database. In step 286, method 200 proceeds by performing a sliding matching algorithm, a permutative matching algorithm, or a hybrid matching algorithm to fill the remaining gaps in the eleventh string of contiguous characters. When the sliding matching algorithm, permutative matching algorithm, or hybrid matching algorithm is complete, method 200 proceeds to a step 292 of outputting a report comprising the at least one reference sequence that matches the at least one query sequence. In such a step, the report can include a histogram for the at least one query sequence indicating the most likely species of origin of the at least one query sequence, an alignment of the at least one query sequence with one or more matching reference sequences in the forward lookup table, and identification of a polymorphism in the at least one query sequence selected from the group consisting of an insertion, a deletion, or a mutation.

When gaps remain in a reconstructed sequence of matching reference sequence segments for each species, a sliding matching (or slide matching) algorithm can be performed to further reduce the gaps in the reconstructed sequence. This can be accomplished alone after any round of gap filling using the RLts, after gap filling using all the RLts, or in combination with permutative matching, for example, to identify discrete differences in nucleic acid and protein sequences between the at least one query sequence and at least one reference sequence stored in the forward lookup table. Sliding matching is exemplified throughout the Examples. In some implementations, the sliding matching algorithm comprises determining a gap length G and offset K for each gap remaining in the reconstructed sequence, transforming each gap having length G into two consecutive non-overlapping segments comprising a first overlapping segment comprising an overlapping portion beginning at offset $K=K-\frac{1}{2}G$ and a gap portion beginning at offset K and a second overlapping segment comprising a gap portion beginning at offset $K=K+\frac{1}{2}G$ and an overlapping portion beginning at offset $K=K+G$, transforming the at least one query sequence into two query sequence segments comprising a first query sequence segment comprising G contiguous characters beginning at an offset I corresponding to the offset K of the overlapping portion of the first overlapping segment and a second query sequence segment comprising G contiguous characters beginning at an offset I corresponding to the offset K of the gap portion of the second overlapping segment, querying the first and second query sequences against the reference sequence in the forward lookup table for each species and inserting matching query sequence characters and reference sequence characters into a reconstructed sequence to reduce any gaps remaining in the sequence after gap filling. It should be appreciated that the gaps do not need to be divided in half as in the example above, for example, the algorithm can proceed by sliding the two consecutive overlapping segments anywhere along each gap between a first offset K=(K−(G−1)) and a second offset K=(K+(G−1)), respectively and repeating the process above to fill each remaining gap until a discrete difference is identified between the at least one query sequence and at least one reference sequence. In such implementations, the gaps can be divided into unequal and overlapping gaps and starting at off-center offsets. After slide matching, any gaps remaining in a gap that was reduced with slide matching can be reinserted into the slide matching algorithm, and the process can continue until all of the gaps are filled or a discrete difference between the at least one query sequence and at least one reference sequence is determined.

Permutative matching is exemplified throughout the Examples. In some implementations, the permutative matching algorithm comprises generating all possible characters available to fill the gaps and querying each of the possible characters at each position in the gap against the reverse lookup table comprising a preselected positive integer k that is equal to the gap length and permutatively filling the gaps. Permutative matching can be performed before sliding matching, after sliding matching, or together with sliding matching in the form of hybrid matching. The hybrid matching algorithm comprises a combination of the permutative matching algorithm and the sliding matching algorithm. In some implementations, hybrid matching involves performing a round of sliding matching and then filling remaining gaps with permutative matching. In some implementations, hybrid matching comprises performing a round of permutative matching to fill at least a portion of a gap, for example, until a gap remaining has a length matching an RLt_k available, and then using sliding matching to fill the remaining gaps. In some implementations, hybrid matching comprise alternating back and forth between sliding matching and permutative matching until all of the gaps are resolved and discrete differences are determined between the at least one query sequence and a matching at least one reference sequence.

In some implementations, step of querying (e.g., 240, 258, 278) is always performed without concurrently constructing each of the at least one reverse lookup tables.

In some implementations, the data processing system comprises a thread manager configured to concurrently generate the set of Y−k+1 consecutive overlapping query sequence segments, query the set of Y−k+1 consecutive overlapping query sequence segments against the at least the first set of L/k consecutive non-overlapping reference sequence segments, create a set of matching reference sequence segments for each species of origin. In some implementations, the thread manager is optionally configured to apply the sliding matching algorithm, permutative matching algorithm, and hybrid matching algorithm concurrently with transforming the at least one query sequence into the at least the first set of L/k consecutive non-overlapping query sequence segments, querying the at least the first set of L/k consecutive non-overlapping query sequence segments against each set of Y−k+1 consecutive overlapping reference sequence segments, and creating the set of matching reference sequence segments for each species of origin. In some implementations, wherein the at least one query sequence comprises a plurality of query sequences comprising n query sequences where n is a positive integer greater than 2, and the thread manager is configured to concurrently transform the plurality of query sequences into sets of consecutive non-overlapping query sequence segments and process the consecutive non-overlapping query sequence segments, and consolidate data correlating to each of the concurrently processed sequences to generate a report selected from the group consisting of a histogram for the at least one query sequence indicating the most likely species of origin of the at least one query sequence, an alignment of the at least one query sequence with one or more matching reference sequences in the forward lookup table, and identification of a polymorphism in the at least one query sequence selected from the group consisting of an insertion, a deletion, or a mutation.

In some embodiments, the present invention provides a data processing system for matching at least one query sequence with at least one reference sequence, for example, using a cascading parallelization schema as described in Example 3. The data processing system includes a computer database environment and a processor circuit. The computer database environment includes a forward lookup table and a plurality of reverse lookup tables maintained in a non-transitory computer readable storage medium and configured to relate each set of Y−k+1 consecutive overlapping reference sequence segments stored in records of the plurality of reverse lookup tables to reference sequences stored in records of the forward lookup table, wherein each set of Y−k+1 consecutive overlapping reference sequence segments comprises a first string of contiguous characters having a length equal to a preselected positive integer k which differs for each of the reverse lookup tables. The processor circuit includes a thread manager configured to create a maximum number of threads available in response to receiving a query comprising at least one query sequence comprising a second string of contiguous characters having a length equal to a positive integer L, wherein the maximum number of threads comprise a first at least one thread for partitioning the at least one query sequence, a second at least one thread for querying the plurality of reverse lookup tables, and a third at least one thread for gap filling, and wherein the maximum number of threads perform asynchronously and in parallel the following steps of transforming, querying, gap filling, and outputting. In some implementations, the processor circuit performs the step of transforming, for each query sequence via the first at least one thread, each query sequence of the at least one query sequence into a set of L/k consecutive non-overlapping equally sized query sequence segments each having a string length of k contiguous characters which corresponds to the preselected positive integer k for each reverse lookup table in the computer database environment. In some implementations, the processor circuit performs the step of querying, via the second at least one thread, each set of transformed consecutive non-overlapping query sequence segments comprising the string length of k contiguous characters against the corresponding reverse lookup table comprising the preselected positive integer k for each set of Y−k+1 consecutive overlapping reference sequence segments in the corresponding reverse lookup table that match non-overlapping query sequence segments, wherein matching sets of Y−k+1 consecutive overlapping reference sequence segments are sorted by species and preselected positive integer k to create a set of equally sized matching reference sequence segments for each species. In some implementations, the processor circuit is configured to perform a step of gap filling, for each set of equally sized matching refer sequence segments via the third at least one thread, to match the at least one query sequence with at least one reference sequence in the forward lookup table. The at least one reference sequence that matches the at least one query sequence is then output. Gap filling is performed for each species by iterating through each of the reverse lookup tables as described above. In some implementations, the processor circuit further comprises at least one central processing unit (CPU) having at least one processing core. In some implementations, the maximum number of threads available depends on the number of CPUs and cores per CPU. It should be appreciated that multiple CPUs each having multiple processing cores can provide for a large maximum number of available threads. In some implementations, the processor circuit includes a fourth at least one thread for permutative matching, for example, to fill gaps remaining after gap filling. In some implementations, the processor circuit includes a fifth at least one thread for sliding matching, for example, to fill gaps remaining after gap filling. In some implementations, the processor circuit includes a sixth at least one thread for hybrid matching, for example, to fill gaps remaining after gap filling. It should be appreciated that permutative matching can also be used to fill gaps remaining after sliding matching and vice versa, as is done in the hybrid matching algorithm.

In some implementations, wherein the maximum number of threads available is equal to a number of threads required to match each query sequence of the at least one query sequence. In some implementations, the number of threads required to match each query sequence of the at least one query sequence is equal to the number of query sequences in the at least one query sequence and the number of offset alignments to be tried for each of the query sequences. In some implementations, when more threads are needed than the maximum number of threads available additional tasks are queued until threads become available. In some implementations, the thread manager assigns each thread a hashed sequence, offset and segment size, up to maximum number of threads. In such implementations, additional hashed sequence, sequence offsets, and segment sizes can be queued for later processing.

In some implementations, the database comprises multiple redundant copies of each database in the computer database environment. In some implementations, multiple copies of each database are saved on multiple different solid state drives. In some embodiments, the computer database environment comprises a different database for different taxonomical groups. For example, human genomic data transformed into a forward lookup table and a plurality of reverse lookup tables can be stored in a first database, bacterial genomic data can be transformed into a forward lookup table and a plurality of reverse lookup tables and stored in a second database, viral genomic data transformed into a forward lookup table and a plurality of reverse lookup tables can be stored in a third database, fungal genomic data transformed into a forward lookup table and a plurality of reverse lookup tables can be stored in a fourth database, etc. In such implementations, the different databases can each be stored on the same at least one hard disk, at least one solid state drive (e.g., PCIe SSD card), or stored on different at least one hard disk, or at least one solid state drive (e.g., PCIe SSD card). In some embodiments, the database is broken into several portioned databases to increase optimization of database querying. In some such implementations, the thread manager can assign the same at least one query sequence to several threads, but assign each thread to a unique portioned database. In some implementations, each reverse lookup table is partitioned into one or more smaller reverse lookup tables. In some implementations, RAM provides working space for multiple computing threads that simultaneously query the databases and process the results.

EXAMPLES

Example 1

Example 1 describes an exemplary method, apparatus, and system for performing a process for matching at least one query sequence with at least one reference sequence. The method, apparatus, and system described herein efficiently matches an undefined DNA or RNA sequence to a DNA or RNA sequence stored in a database of DNA or RNA sequences from individual species. The method, apparatus, and system are comprised of an optimized hardware piece and an optimized software architecture, both optimized to the specific problem of matching biological sequences (e.g., DNA/RNA). Matching is efficiently achieved using a combination of two elements: the unique structure of the database and the unique matching algorithm that relies on bit operations rather than string operations. A computer database environment is created by transforming public and private databases, which contain organism DNA/RNA sequence information into a database of hashed DNA/RNA sequences of different lengths. Records in the hashed database contain partial "reverse" records. Each hashed DNA/RNA record provides descriptions of all the organisms that contain that particular DNA/RNA sequence. The hashed database is stored in either several asynchronously accessible solid state drives (SSD) or can alternatively be stored in random-access memory (RAM), however persistent memory is preferred. In some implementations of the method, apparatus, and system described herein multiple complete databases accessed independently and asynchronously. Matching is completed by breaking the undefined DNA/RNA query sequence into segments, which are then matched "in order" to segments in the database while accounting for mutation and misalignment possibilities.

Modern DNA/RNA sequencing has reached the point where DNA/RNA can be sequenced inexpensively. This makes the ability to sequence widely available. However, many questions still exist regarding how a sequence can be used. One possibility is a medical diagnostic tool that exactly identifies pathogens in patient samples. Other possibilities include use for drug research and general academic style research. Current DNA/RNA matching tools are too slow and inaccurate to make these possibilities feasible.

Existing DNA/RNA fast matching algorithms are not parallelized and utilize string matching techniques. In some implementations the method, apparatus and system described herein improves on these algorithms by converting the DNA/RNA sequence to a tuple with each DNA/RNA residue represented by a three bit integer. This allows for bitwise operations rather than string operations for matching. The method, apparatus, and system described herein for fast DNA/RNA matching is preferable over existing methods because it greatly reduces the number of operations for DNA/RNA matching. It further reduces time by creating a custom novel parallel computing environment specifically tailored to permit fast DNA/RNA matching.

Figure 7:
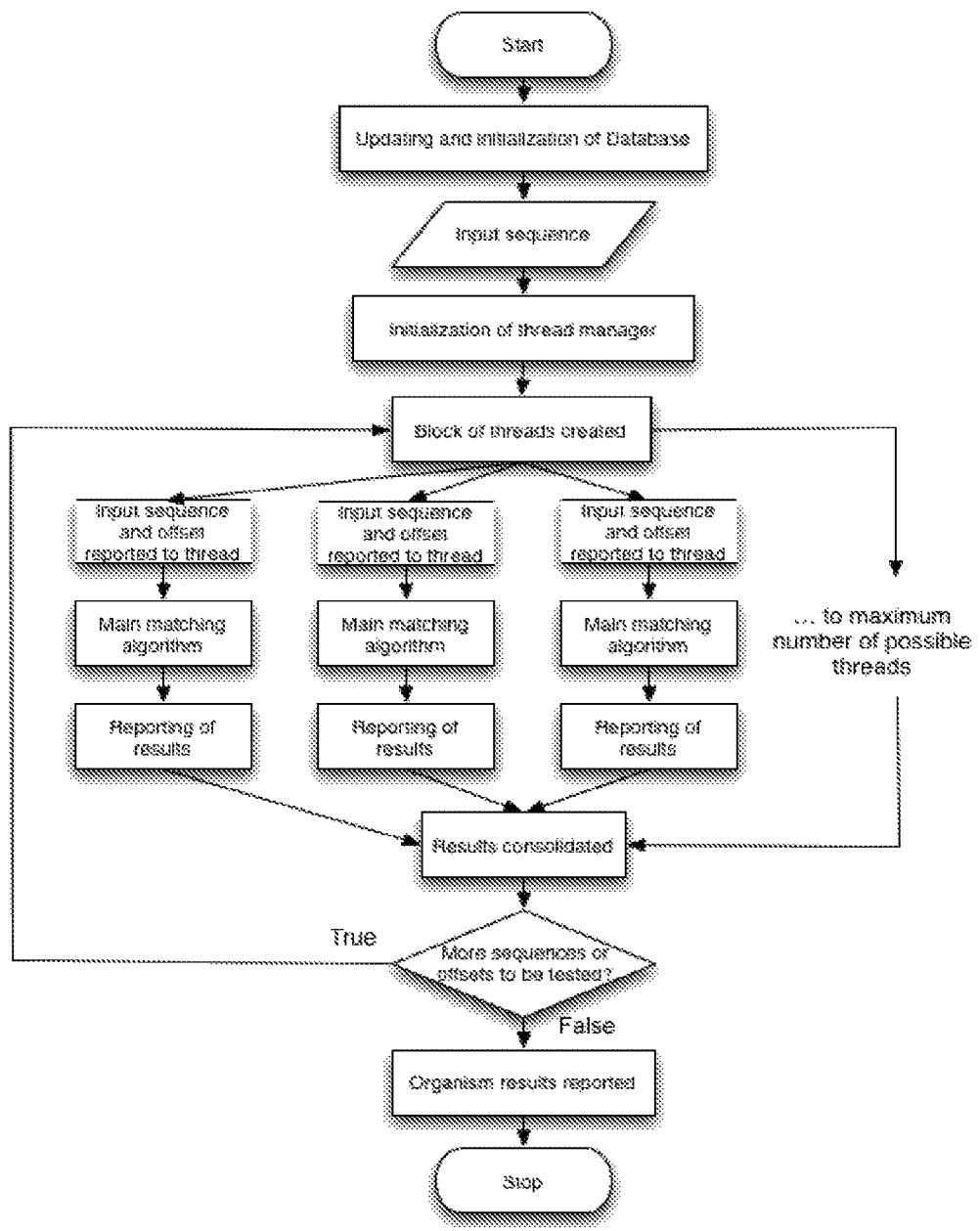
FIG. 7 is a flow chart illustrating a process for matching at least one query sequence with at least one reference sequence in accordance with an example embodiment of the present invention.
Figure 8:
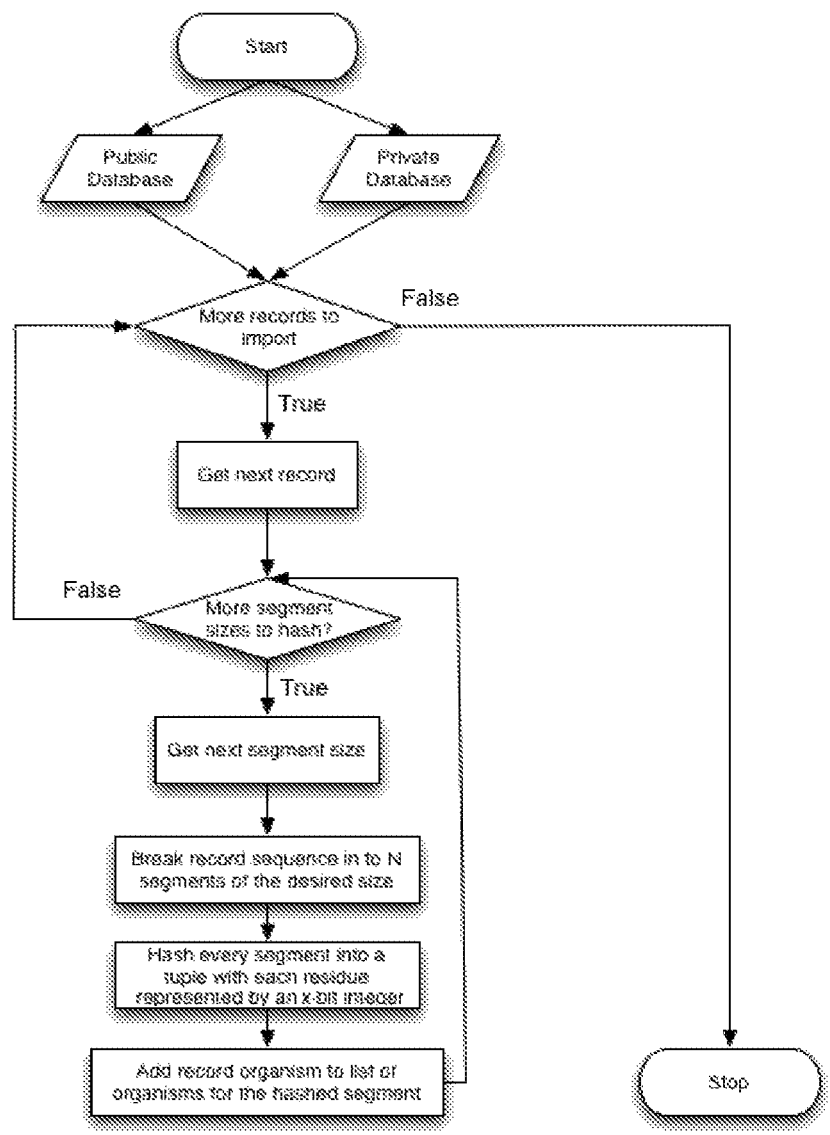
FIG. 8 is a flow chart illustrating an overview of a process for transforming genomic data into a computer database environment comprising a forward lookup table and a plurality of reverse lookup tables which relate consecutive overlapping reference sequence segments to reference sequences stored in the forward lookup table in accordance with an example embodiment of the present invention.
Figure 9:
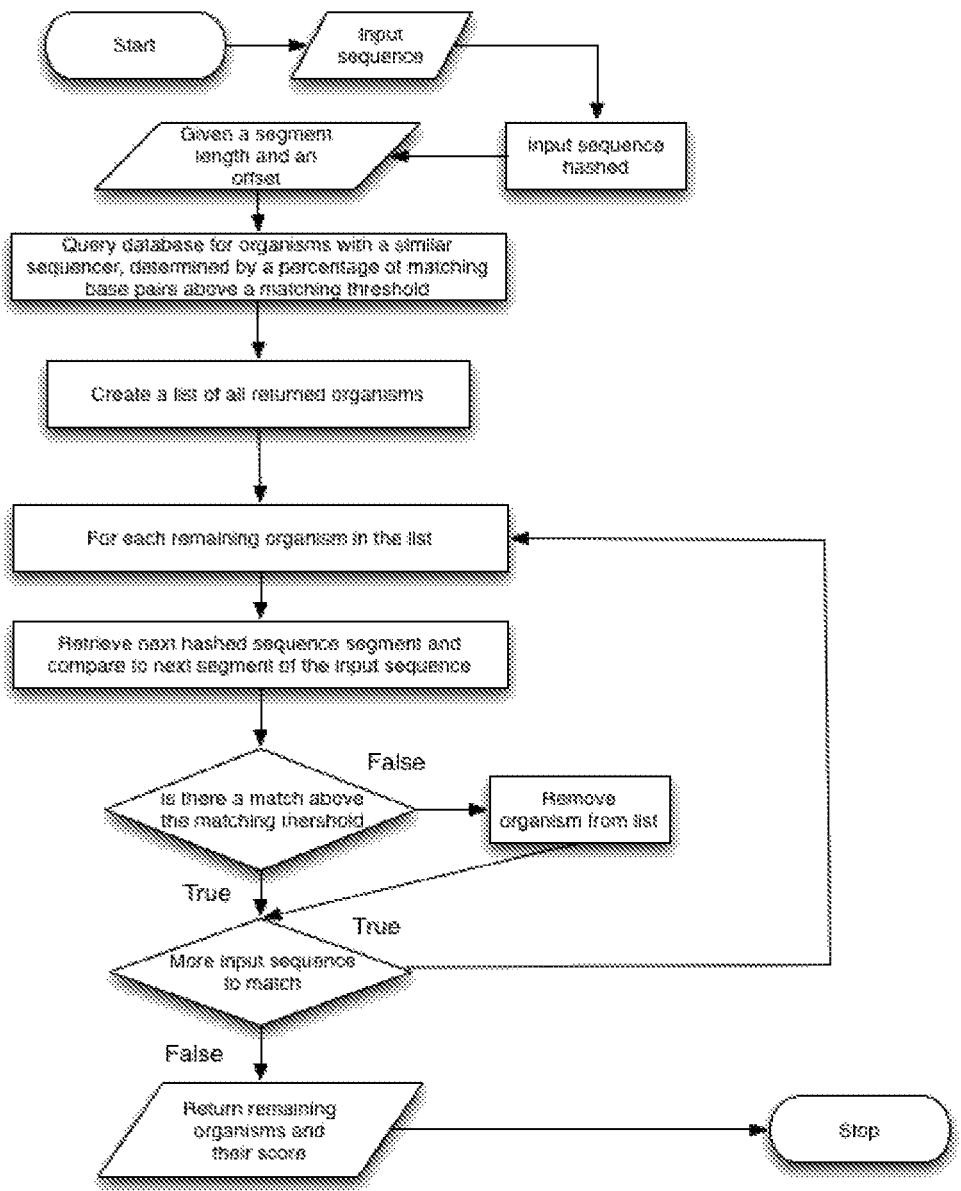
FIG. 9 is a flow chart illustrating a process for matching at least one query sequence with at least one reference sequence in accordance with an example embodiment of the present invention.
Figure 11:
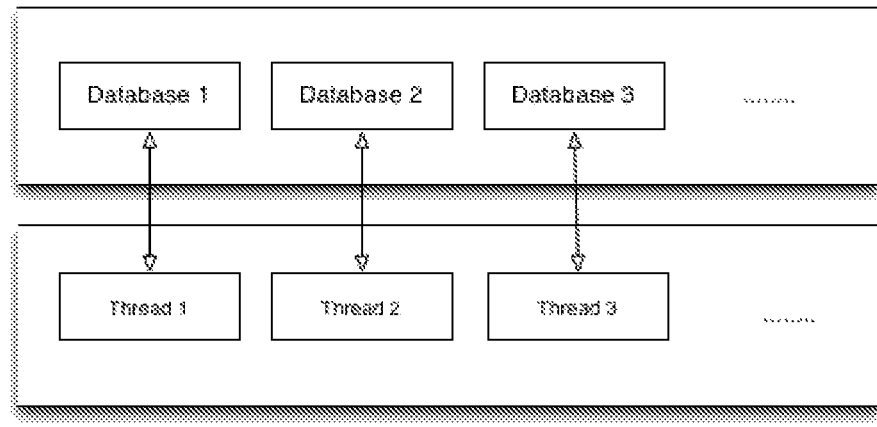
FIG. 11 is a schematic illustrating a parallelization schema in accordance with an example embodiment of the present invention.
Figure 11:
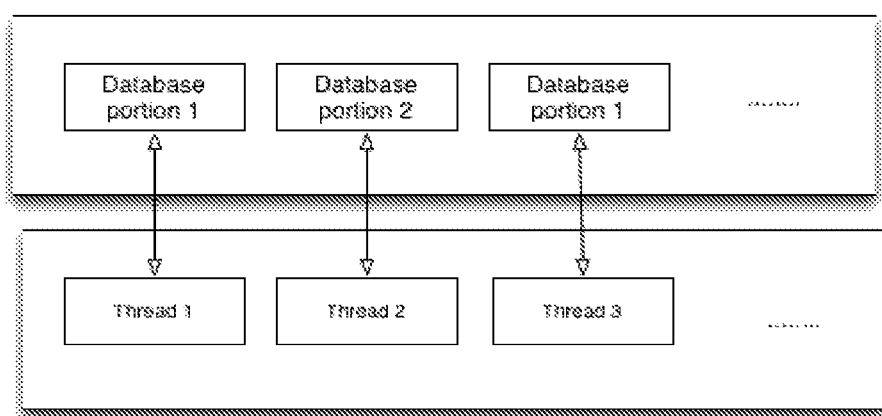
Figure 12:
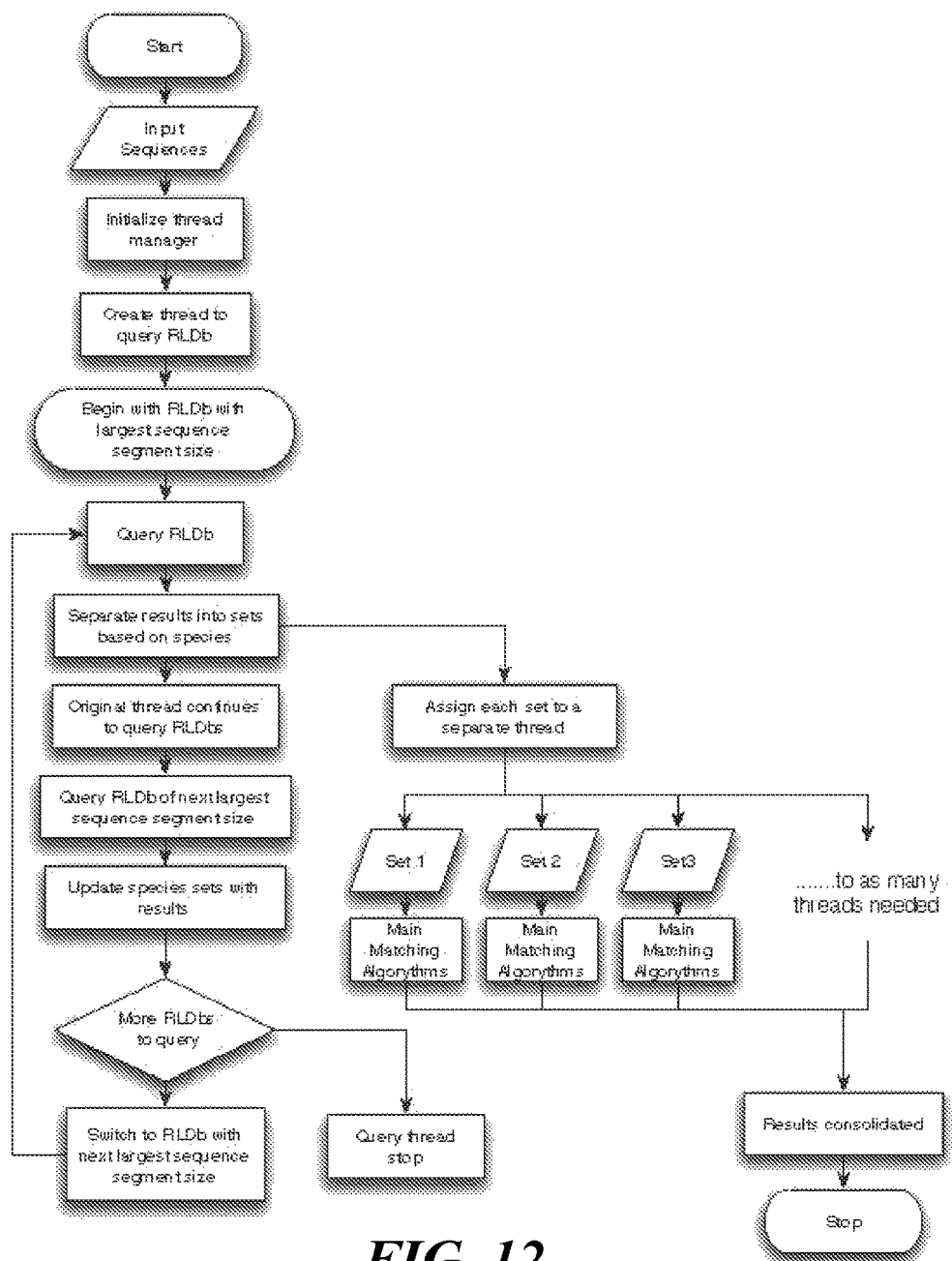
FIG. 12 is a flow chart illustrating a process for matching at least one query sequence with at least one reference sequence in accordance with an example embodiment of the present invention.
Figure 13:
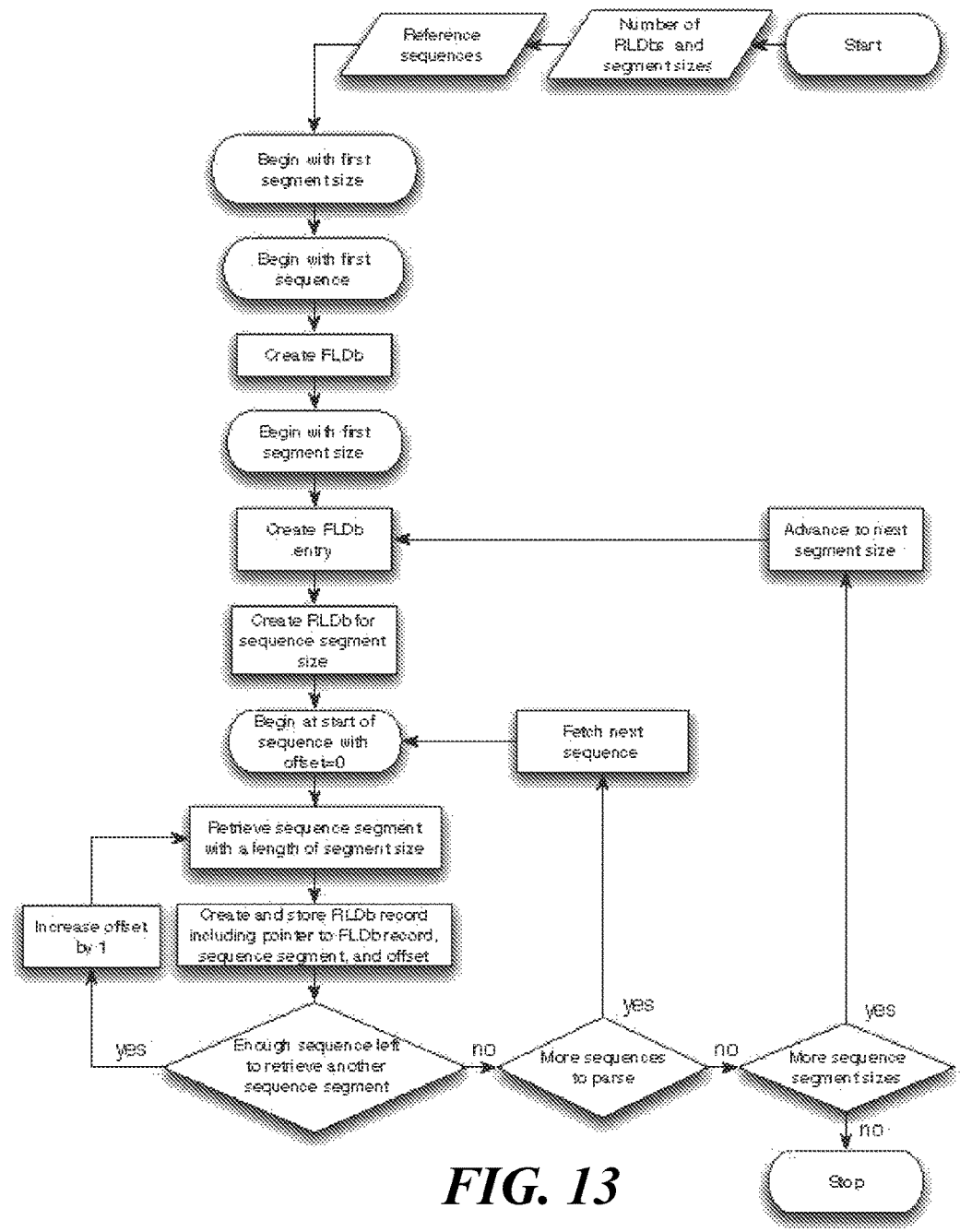
FIG. 13 is a flow chart illustrating a process for transforming genomic data into a computer database environment comprising a forward lookup table and a plurality of reverse lookup tables which relate consecutive overlapping reference sequence segments to reference sequences stored in the forward lookup table in accordance with an example embodiment of the present invention.
Figure 14:
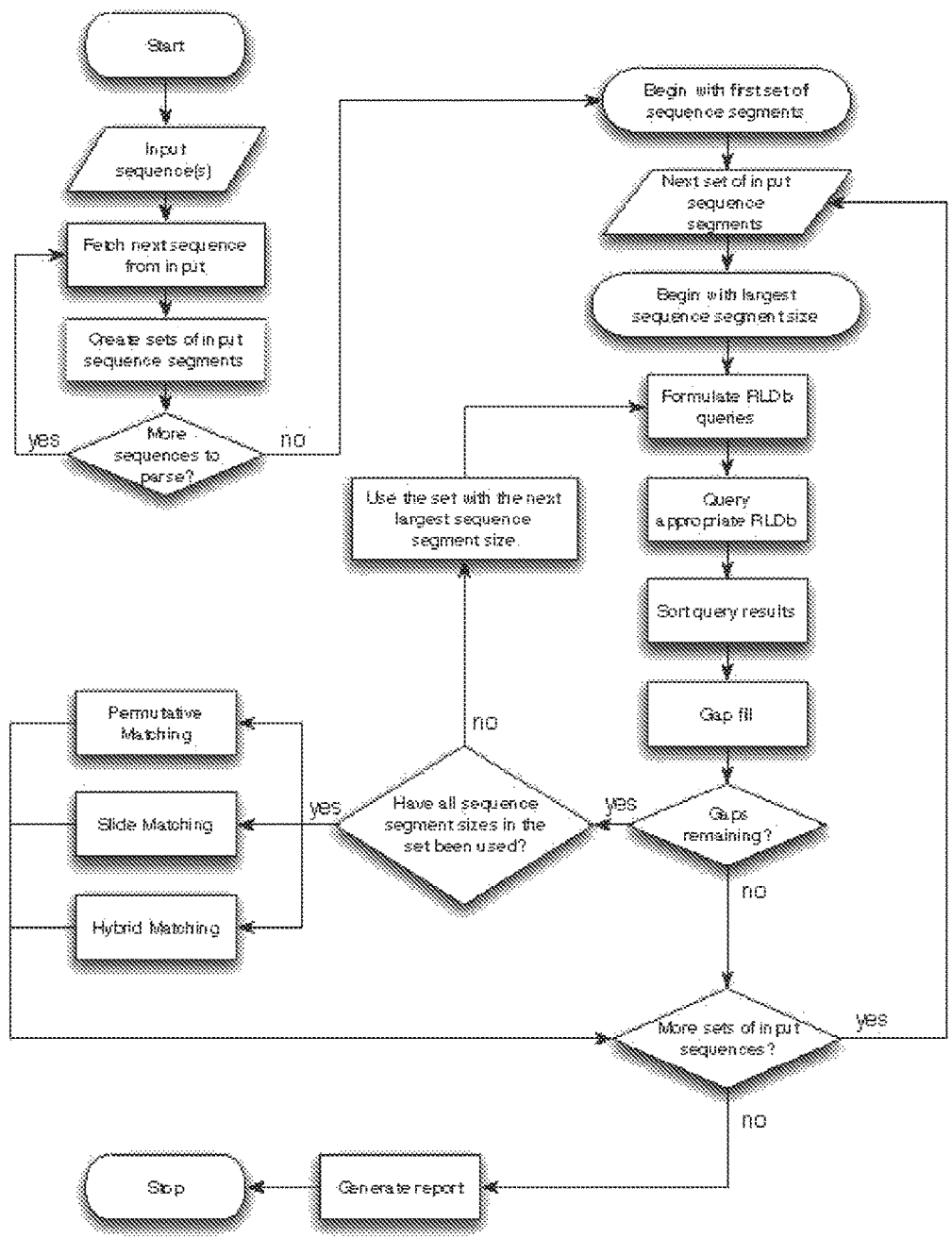
FIG. 14 is a flow chart illustrating a process for matching at least one query sequence with at least one reference sequence in accordance with an example embodiment of the present invention.

As will be explained in further detail below, FIG. 7 is a flow chart illustrating the overall process for fast DNA/RNA matching, FIG. 8 is a flow chart illustrating an exemplary implementation of the creation of the hashed database, FIG. 9 is flow chart illustrating an exemplary implementation of the matching algorithm, FIG. 10 is a diagram showing an exemplary selection of hardware components used in the method, apparatus and system described herein, and FIG. 11 is a diagram showing an exemplary implementation of the parallelization schemas used in the method, apparatus and system described herein.

Exemplary components of the method, apparatus and system described herein are an algorithm for creating a hashed tuple from a DNA/RNA sequence, an algorithm for creating a database containing the complete records from publically and privately available organism specific DNA/RNA information, an algorithm for deciding into what size tuples to segment the input DNA/RNA, an algorithm to deal with alignment and mutation sequence differences, which is based on a scoring schema and referred to herein as "permutative matching," a hardware parallelization schema (see FIG. 10 consisting of multiple SSDs and large amounts of RAM to host multiple identical but asynchronous hashed databases, a software parallelization schema (see FIG. 11) consisting of multiple querying threads controlled by one master thread, parallel computing threads connected to a unique sub-database containing only a specific portion of the entire hashed database, a computing thread manager that coordinates connecting of threads to sub-databases and the dispersal of searches across available threads.

In some implementations, computer database environment is employed in which multiple identical instances are used and contain some or all of the following: records indexed by hashed DNA/RNA sequence segments that identify all organisms containing that DNA/RNA sequence as well as information about where in the organisms full DNA/RNA sequence the segment can be found, and records containing the full hashed sequence for an organism. Assembling the above listed hardware components will be obvious to anyone with ordinary skills in computer assembly.

The hardware components listed in FIG. 10 (motherboard, CPUs, power supply, SSDs, and DDR RAM) are standard components available from a wide variety of suppliers. The above algorithms can be readily coded by one of ordinary skill in the art based on the teaching of the present disclosure. The method, apparatus and system described herein achieves its results as follows. The computer hardware show in FIG. 10 creates a specific environment to allow parallelization of the algorithms used in the invention. Multiple SSDs provide a framework to house several identical but asynchronously accessible databases. Each SSD could hold a portion of a database, one database, or several databases. A large amount of RAM is used to create additional identical databases, whether single or multiple complete databases, or single or multiple portions of the database. The RAM also provides a working space for the multiple computing threads that will be simultaneously querying the databases and processing the results. A large number of computing threads is provided by multiple CPUs that each have multiple processing cores. On each SSD single or multiple complete databases, or single or multiple database portions are stored. The databases, whether single or multiple complete databases, or single or multiple database portions can also be stored in RAM. Before the method, apparatus, and system described herein can match undefined DNA/RNA to DNA/RNA from the database, the database must be prepared. The database is created from existing public or privately supplied databases. Each record from a private or public database is transformed to create several records in the database. The first record in the database is the name of the organism, species, or as much taxonomical detail as is provided; and the hashed DNA/RNA sequence. Then DNA/RNA from the public or private databases is broken into segments of each required segment size. Each new segment is hashed according to the hashing algorithm. Then if an identical hashed sequence segment already exists in the database, the organism or taxonomical record is added to the existing record with identical hashed sequence segment, along with information regarding where in the organism's or taxonomical record's full sequence the sequence segment is located. If no identical hashed sequence segment exists a new record is created and the organism or taxonomical record added, along with information regarding where in the organism's or taxonomical record's full sequence the sequence segment is located. These records are "reverse" records in that they point a sequence segment back to an organism or taxonomical record.

The database can be maintained in several forms: the entire database, or broken into several portioned databases to increase optimization of database querying. When broken into several portioned databases, the thread manager assigns the same input sequence to several threads, but assigns each thread a unique portioned database. For a given hashed DNA/RNA sequence segment, the database has a record of each known organism that contains that DNA/RNA sequence segment, information about where in the organisms DNA/RNA that sequence segment can be found, and the location of the nearest stop codon identified by one of the base combinations: TAG, TGA, TAA. The database or portioned database contains reverse look-up records for one or more segment sizes. Different segment sizes are used based on the length of the DNA/RNA sequence to be identified.

In some implementations, a DNA/RNA sequence or sequence segment is hashed into a tuple of three bit integers. In such implementations, each base in the DNA/RNA sequence or sequence segment is assigned a three bit value, and thus an integer value from 0-7. Only the values 0-3 are assigned to the bases of the sequence or sequence segment. The extra bit is to accommodate "wildcard" bases, for example from incomplete records in the public and private databases or when sequences are missing for a species, but a general sequence is provided for a higher taxonomical group. Matching between hashed sequence segments or hashed sequences is then done very efficiently with bitwise operations.

After the database or portioned databases are prepared, it is loaded into a SQL or NoSQL database and stored either long term on the SSDs or during run time in RAM. Once the database or portioned databases are prepared and an undefined sequence, sequence segment or multiple undefined sequences or sequence segments are provided, the thread handler is engaged to create as many threads as possible given the number of CPUs and cores per CPU. The number of required threads is determined by the number of provided undefined sequences or undefined sequence segments and the number of offset alignments to be tried for each undefined sequence or undefined sequence segment. If more threads are needed then the maximum number of available threads, then additional required tasks are queued until threads become available. The thread handler assigns each thread a hashed sequence, sequence offset and sequence segment size, up to the maximum number of threads. Additional hashed sequences, sequence offsets, and segment sizes are queued for later processing.

Each thread then takes the given hashed sequence, sequence offset, sequence segment size and assigned database or portioned database and undergoes the matching algorithm depicted in FIG. 9. A hashed sequence segment of length equal to the sequence segment length and beginning at the sequence offset is then copied from the hashed sequence and used to query the database or portioned database. The database or portioned database then returns a list of all organisms or taxonomical groups containing the hashed sequence and an offset indicating where in that organism's or taxonomical group's sequence the sequence segment was found. The matching score for this initial matched sequence segment is then considered 1. If no records are returned, the given sequence is altered in the following manner and this shall be referred to as permutative matching: N*3 new sequences are created where N is the length of the sequence segment. A new sequence changes one base, such that the N*3 new sequences provide all possibilities of changing one base to one of the three other options. Each new sequence is queried against the database or portioned database and all returned records are added to the list. The matching score for each of these records is N−1/N. If no records are returned after this, then this technique is repeated for changing two bases at a time, then three, then four and so on, with the reported scores being (N−B)/N where B is the number of bases changed. Once a list of returned records has been obtained, the thread continues the matching process as follows: For each of the organisms on the list, obtain the next sequence segment of sequence segment length, or obtain the remaining sequence. Calculate a matching score using bitwise operations. This calculation tells the percentage of bases that match. If this percentage is above a matching threshold, accept the segment as a match, record the matching percentage as the matching score and move onto the next segment. If this is the last segment for this record, move onto the next organism or record. If this percentage is not above a matching threshold. Offset the organism sequence by one, two, and so on until reaching the length of the sequence segment to find all alignments with a matching score above the matching threshold. Offset the organism sequence to align the organism sequence with the input sequence in such a way to align the nearest stop codon base combinations. Undergo the permutative matching and find permutative scores above the matching threshold. Then accept the alignment or permutation with the highest score, record the score, and move onto the next segment. If this is the last segment for this organism record, move onto the next organism or record. The total score is reported as a combination of the sum of the individual percentage scores, the product of the individual percentage scores, the number of permutations and/or offset alignments used, and the total length of the sequence. After all organisms and taxonomical records have been scored, these scores are reported to the thread manager to be consolidated and reported with all other threads. At this point an individual thread is released and can be reused by the thread manager if additional matching algorithms are still in the queue.

Example 2—Workflow for Hypothetical Sequence

Example 2 illustrates an exemplary implementation of the method, apparatus and system described herein using hypothetical sequences. This example divides the exemplary implementation into different parts including a "preprocessing" which describes creation of the computer database environment comprising a forward lookup table (FLt) and at least one reverse lookup table (RLt) which relates reference sequence segments (k-tuples) stored therein to reference sequences stored in the Fit, an "input processing" section which describes transformation of at least one query sequence into sets of corresponding query sequence segments which are used to query the computer database environment, a "Querying" section which describes how the transformed query sequence segments are used to query the RLts in the computer database environment, and a "Processing" section which describes how the query results are processed to match the at least one query sequence to at least one reference sequence stored in the forward lookup table, followed by sections exemplifying "Permutative Matching," "Sliding Matching" and "Hybrid Matching."

Preprocessing

Before the algorithms can be used there is a preprocessing step to generate the databases required by the algorithms. Unlike other algorithms that preprocess references and store binary trees in memory/RAM, our preprocessing stores the results in a database stored long term outside of RAM. Thus the preprocessing step does not happen each time the algorithms are used.

A computer database environment contains a Forward Lookup Database (FLt) and at least one, or at least two, or at least three, if not more, Reverse Lookup Databases (RLts). Records in the FLt are generated directly by transforming genomic data (e.g., sequence files (nucleotide or protein (aka amino acids)), usually from public sources such as the NIH, into a plurality of records in the Fit, for example, by parsing and header and genomic sequence information for each reference sequence in the genomic data to create the plurality of unique records in the Fit. Each unique record contains database of origin, accession number, recommended name, organism name, gene name, protein existence number, and sequence version. An exemplary record in the FLt is shown in Table 1 below.

TABLE 1

{"_id" : ObjectId("53ab7e8f36832540e2e16cd0"), "Gen_Bank_accession" : "AAB05651",
"Strain" : "F45",
"Description" : "outer capsid VP4 (Rotavirus A F45)",
"Country" : "",
"ViPR_ID" : "1619765",
"sequence" :MASPFYRQLLTNSYSVDLHDEIEQIGSEKTQNVTVNPGPFAQTRYAP
(SEQ ID NO: 1)" }

Each RLt is an inverted index, and has an assigned sequence segment size (e.g. 10, 50, 100). Each record in an RLt is indexed off a sequence segment and contains a pointer to a record in the FLt and a sequence offset. An exemplary record in an RLt is shown in Table 2.

TABLE 2

{ "_id" : ObjectId("53ac1f133d4149c0d971c9fb"),
"word" : "MASPFYRQLL (SEQ ID NO: 2)",
"forwardRowId" : "53ab7e8f36832540e2e16cd0", "offset" : 0 }

As shown in Table 2, the pointer (i.e., "forwardRowId") to the FLt record identifies the species/strain/subspecies sequence segment is contained in, and the offset indicates where in the species/strain/subspecies sequence the sequence segment is found. Querying an RLt with a sequence segment then returns a list of all FLt records the sequence segment is found in. Table 3 lists a sample of results obtained by querying an RLt having segment size 10 for a query sequence segment comprising 10 amino acids "MASPFYRQLL (SEQ ID NO: 2)."

TABLE 3

{"word" : "MASPFYRQLL (SEQ ID NO: 2)", "forwardRowId" : "53ab7e8f36832540e2e16cd0", "offset" : 0 }
{"word" : "MASPFYRQLL (SEQ ID NO: 2)", "forwardRowId" : "53ab803f36832540e2e2c8bf", "offset" : 0 }
{"word" : "MASPFYRQLL (SEQ ID NO: 2)", "forwardRowId" : "53ab81cf36832540e2e3c6b2", "offset" : 0 }
{"word" : "MASPFYRQLL (SEQ ID NO: 2)", "forwardRowId" : "53ab842c36832540e2e58cdd", "offset" : 0 }
{"word" : "MASPFYRQLL (SEQ ID NO: 2)", "forwardRowId" : "53ab84a336832540e2e5e70b", "offset" : 0 }

Each RLt is constructed from the FLt and a given sequence segment size k, by transforming each reference sequence stored in the FLt in to a set of Y−k+1 reference sequence segments, given the length Y of the full sequence in the FLt, and corresponding offsets. Offset 0 in the full sequence indicates the beginning of the sequence, and offset I would indicate the (I+1)th character in the full sequence. Table 4 below shows an example of computer readable code which can be used to transform each reference sequence in the FLt into a set of reference sequence segments.

TABLE 4

```
for ( I = 0; I <X+Y+1; ++I) {
    starting at offset I retrieve X characters from the sequence
}
```

Each sequence segment thus transformed, its offset I, and the pointer to the FLt record are then stored as one record in the RLt_k (meaning RLt of sequence segment size k). Table 5 below lists an exemplary RLt_10 record for transformed reference sequence segment MASPFYRQLL (SEQ ID NO: 2), the pointer indicating the FLt record where the transformed reference sequence segment can be found, along with offset I=0 indicating that the sequence segment begins at the N-terminus of the protein sequence.

TABLE 5

{"word" : "MASPFYRQLL (SEQ ID NO: 2)", "forwardRowId" : "53ab7e8f36832540e2e16cd0", "offset" : 0 }

This process is repeated for all RLt sizes, resulting in a computer database environment comprising a FLt and a plurality of RLts. In one implementation, each reference sequence in the FLt is transformed into sets of reference sequence segments having k sizes of 10, 50, and 100 (FLtRLt_10, RLt_50, RLt_100).

Input Processing

Input for the algorithms can be any type of file, media, serial/usb/network connection from which at least one query sequence comprising a third string of contiguous characters can be extracted. The input can contain any number of full or partial sequences.

Each full or partial at least one query sequence with length L provided as input is transformed into N sets of consecutive non-overlapping query sequence segments, where N is the number of RLts available, each with sequence segment size k, for example, by partitioning each set of input query sequences into L/X consecutive non-overlapping segments, while recording the offsets of each of the consecutive non-overlapping reference sequence segments in the input query sequence. Table 6 illustrates transformation of the query sequence "ABCDEFGH," using RLts with sizes 2, 4, and 8, into N=3 sets of consecutive non-overlapping query sequence segments.

TABLE 6

8 : "ABCDEFGH":0
4 : "ABCD:0", "EFGH":4
2 : "AB":0, "CD":2, "EF":4, "GH":6

Querying

In some implementations, each set of consecutive non-overlapping query sequence segments thus transformed is then used to form queries against the appropriate RLt. Using the example above, the first set of transformed consecutive non-overlapping query sequence segments having a segment size k of 8 is used to form queries for the RLt_8 table, the second set of transformed consecutive non-overlapping query sequence segments having a segment size k of 4 is used to form queries for the RLt_4 table, the third set of transformed consecutive non-overlapping query sequence segments having a segment size k of 2 is used to form queries for the RLt_2 table, and the results returned are stored (e.g., in shared memory).

Processing

Processing the stored results from querying the RLts depends on the results desired. If the desired analysis is species identification a histogram can be generated indicating the most likely species the at least one query sequence originated from. A separate histogram can be separately generated for each set of transformed consecutive overlapping query sequence segments. The query results for each set of consecutive overlapping query sequence segments may contain a number of different species. The histogram for each set of consecutive overlapping query sequence segments can describe the frequency of each species. As will be appreciated by the skilled artisan, from this histogram the most likely species of origin can be determined.

For alignment analysis (for standard genetic alignment, mutation analysis, SNP determination, and other applications apparent to the skilled artisan) a "gap filling" algorithm is used alone, or in combination with permutative matching, slide matching, or hybrid matching.

Gap filling begins with the query results from the RLt with the largest sequence segment size that is less than or equal to the length L of the at least one query sequence, and iterates through the other RLt's in order of decreasing sequence segment size k. The query results from the RLt with the largest sequence segment size k are filtered into to create a set of matching consecutive overlapping reference sequence segments of size k for each species of origin. The set of matching consecutive overlapping reference sequence segments for each species can be sorted such that the offset for each consecutive overlapping reference sequence segment in the set is ascending. Then, knowing the sequence segment size k of the RLt in which the consecutive overlapping reference sequence segments are found, any gaps may be identified as missing offsets.

Continuing with the ABCDEFGH example above, when the set with consecutive non-overlapping query sequence segment size k of 8 was queried against RLt_8 (searching for sequences that contain "ABCDEFGH") and after separating by species and sorting, one species set contained the offsets listed in Table 7 below.

TABLE 7

0, 8, 20, 30

The list of offsets in Table 7 indicates that the query sequence segment "ABCDEFGH" was found at those offsets. Reconstructing the sequence in the order of ascending offset results in the reconstructed sequence shown in Table 8 below.

TABLE 8

ABCDEFGHABCDEFGH????ABCDEFGH??ABCDEFGH

The question marks in Table 8 indicate unmatched segments, or gaps. Attempting to fill the gaps, or gap filling, means searching the results of the queries from the query sequence segment sets of smaller sequence segment size k. For example, the gap at offset 16 has a size of four contiguous character gaps, so the results from query generated from query sequence segments having a size k of four can be searched for the same species and the appropriate offset. If a match is found the gap can be filled, and the remaining gaps of size four dealt with. If no match is found, the gap of size four is considered as two gaps of size two for the next iteration which would use the RLt of smallest consecutive overlapping reference sequence segment size k of 2, in this case.

For each iteration, remaining gaps of a size larger than the current RLt sequence segment size can be handled consecutively or with the sliding matching algorithm described below. For example, the gap of size four from above can be partitioned into two gaps of size two starting at offsets 16, and 18 or one gap of size two starting at offset 17. Using a gap of size two at offset 17 may match if the two gaps of size two and offsets 16 and 18 return no matches. The other case is a gap whose size is not an integer multiple of any of the RLt sequence segment sizes. For example, with the above example, a gap of size three at offset J would then be represented by two gaps of size two, one with offset J and the other with offset J+1.

After exhausting all available RLt consecutive overlapping reference sequence segment sizes there may still exist unmatched gaps. For genomic analysis these gaps could be due to mutations, variants, indel editing, bad DNA/RNA sequence, or other reasons. For the purpose of alignment scoring and general analysis it is favorable to eliminate as many remaining gaps as possible. To this end, the method, apparatus and system described herein can use permutative matching, slide matching, or hybrid matching—a combination of the two.

Permutative Matching

For permutative matching, for each remaining gap, generate all possible nucleotide sequences (number is (gap size)^4) and query each against the appropriate RLts (e.g. if the gap is 100 query against RLt_100, if the gap is 50 query against RLt_10). Then use results to fill gaps, filling the filled gaps as permutatively filled. For example, permutative matching, when a query sequence is abcd, a reference sequence is ABTD, and the gap size is equal to 4, all possible permutations of a sequence of size 4 are generated and used to formulate queries, for example, for a nucleotide sequence of size 4 the number is 3^4=81 (3 is used because the query sequence is known to not match, only leaving 3 possible nucleotides per position)). After submitting the queries, any results that fill the gap can be compared to the query sequence to identify variants.

Slide Matching

Slide matching uses overlapping query sequence segments to eliminate as many remaining gaps as possible. Initially the at least one query sequence was transformed into consecutive non-overlapping query sequence segments. Slide matching overlaps one consecutive segment onto another in an effort to reduce to gap sizes smaller than the smallest sequence segment size available in the RLts. As an example, consider the example query sequence and reference sequences shown in Table 8 below (lower case will be used for query sequence and upper case for reference sequence for clarity).

TABLE 8 query sequence : abcdefgh
reference sequence: ABCDETGH

Querying and iterating using the sets of transformed consecutive non-overlapping query sequence segments (e.g., having segment sizes k of 8, 4 and 2, respectively) in the "ABCDEFGH" example above results in the reconstructed sequences listed in Table 9.

TABLE 9

ABCD????
ABCD??GH

In this case slide matching generates two overlaps. The gap of size two at offset 4 is broken in half, into two gaps of size two at offsets three and five, even though no gap exists at offsets three and five. The at least one query sequence can be transformed into two consecutive non-overlapping query sequence segments to generate queries for, in this case "de" and "fg". Matching these two consecutive overlapping query sequence segments with the reference sequence results in the reconstructed sequence shown in Table 10.

TABLE 10

ABCDE?GH

As shown in Table 10, the sliding matching algorithm has reduced the gaps remaining in the reconstructed sequences, thereby identifying a discrete difference between the at least one query sequence and the reference sequence.

This is generalized as follows. For any remaining gaps create new sequence segments to generate queries from, these new sequence segments are allowed to overlap areas without gaps. These new sequence segments do not have to be evenly offset in the gap (e.g. meeting in the middle of the gap) but can be slid around to eliminate as much of the gap as possible. Continuing with the "ABCDEFGH" example above, imagine a gap of size eight at some offset K. Breaking the gap in half and creating two new sequence segments with offsets K−4 and K+4, and querying may not return any matches to fill the gap. In which case slide the new sequence segments to new offsets K−A and K+A (such that there is still an overlap, moving to K−8 and K+8 is the same as querying for the entire gap and thus pointless). Generate new queries and query, if a match is found for one of the two new sequence segments, fill in the appropriate gap pieces, and then treat the remaining gap as a new gap and start the slide matching process over, and iterate until no more possible slide matching remains.

Hybrid Matching

The hybrid matching algorithm comprises a combination of the permutative matching algorithm and the sliding matching algorithm. In some implementations, hybrid matching involves performing a round of sliding matching and then filling remaining gaps with permutative matching. In some implementations, hybrid matching comprises performing a round of permutative matching to fill at least a portion of a gap, for example, until a gap remaining has a length matching an RLt_k available, and then using sliding matching to fill the remaining gaps. In some implementations, hybrid matching comprise alternating back and forth between sliding matching and permutative matching until all of the gaps are resolved and discrete differences are determined between the at least one query sequence and a matching at least one reference sequence. In some implementations, when sliding matching leaves a gap larger than one, permutative matching can be used to effectively fill the gap.

Example 3—Cascading Parallelization

This Example demonstrates how when used in parallel the algorithms are put under a cascading parallel schema. This is the type of parallel schema used when a process has several steps that must occur sequentially, but the process is iterated many times. For example, a query may contain many individual sequences, and query all of the sequences against all of the RLts, each sequence must be transformed into sets of L/k consecutive non-overlapping query sequence segments for each RLt, and each set of consecutive non-overlapping query sequence segments must be queried against corresponding sets of Y−k+1 consecutive overlapping reference sequence segments in each RLt for each sequence, and matching query sequence segments and reference sequence segments must be filtered by species and sorted by offset in ascending order to create matching sets of reference sequence segments for each species which are used to fill gaps in the reconstructed matching reference sequences iteratively through each RLt from the RLt having the largest preselected integer k to the RLt having the largest preselected inter k until all of the RLts are exhausted. This can done in parallel with three threads, one thread that reads transforms the query sequences into the sets of L/k (e.g., $L/k_1$, $L/k_2$, $L/k_3$, $L/k_4$, $L/k_5$) consecutive non-overlapping query sequence segments, one thread that queries each set of transformed query sequence segments against equally sized consecutive overlapping reference sequence segments in the appropriate RLt_k, and one thread that iterates through the RLts to fill gaps in the reconstructed matching reference sequences for each species. When run, the second thread is idle until given a sequence by the first thread, and likewise the third thread is idle until given a set of matching overlapping reference sequence segments by the second thread. The first thread starts the process by transforming the first query sequence, with the second and third threads idle. Next the first thread transforms the second query sequence at the same time the second thread is querying the first set of transformed consecutive non-overlapping query sequence segments and the third thread idle. Then the first thread transforms the third query sequence, while the second thread queries the second set of transformed consecutive non-overlapping query sequence segments, while the third thread fills the gaps in the reconstructed matching reference sequences from the results of the first query, and so on and so forth. It should be appreciated that the at least one query sequence can be many query sequences received in a single query or multiple single query sequences received in multiple individual queries.

Figure 15A:
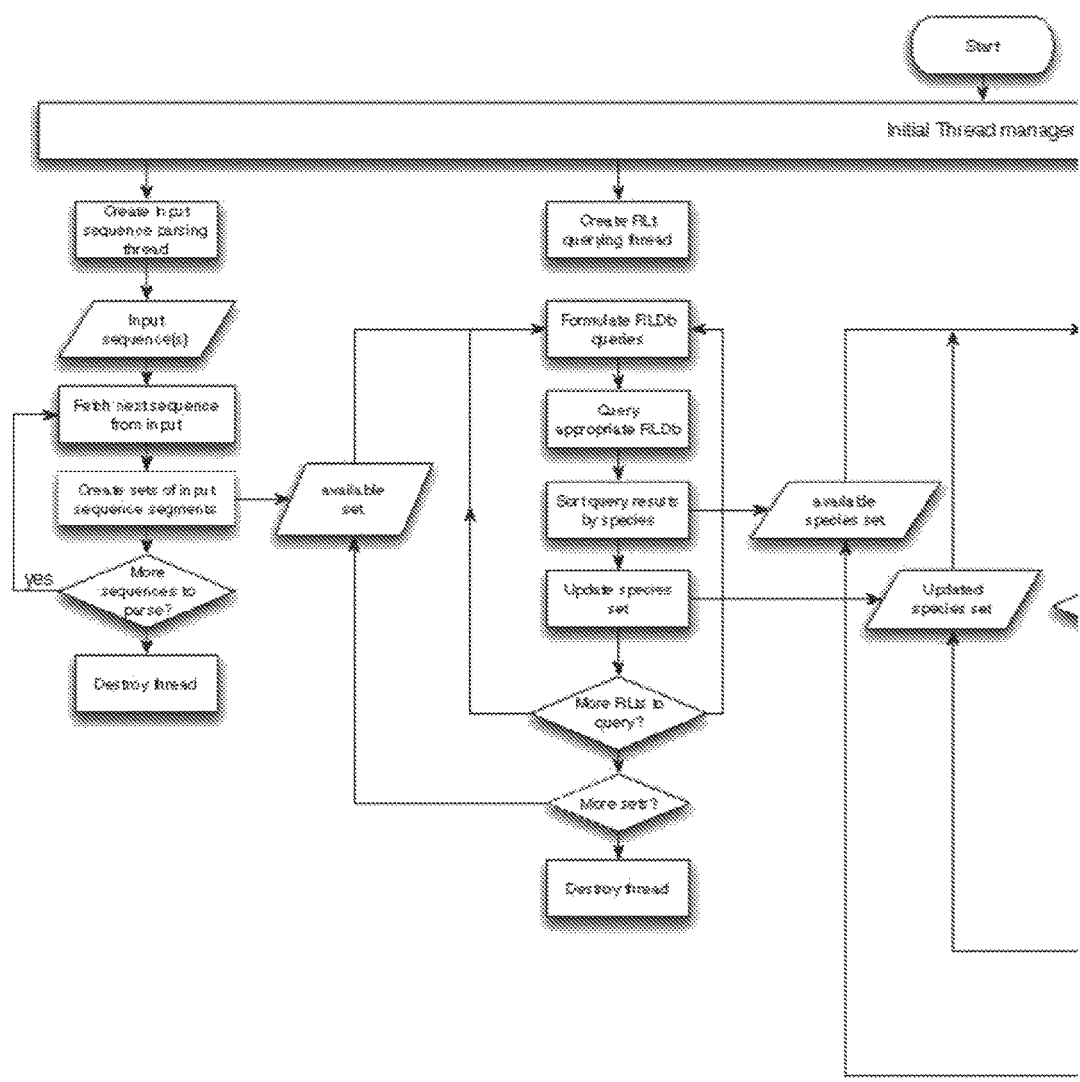
FIGS. 15A and 15B are a schematic illustrating a parallelization schema for performing the process of matching at least one query sequence with at least one reference sequence in accordance with an example embodiment of the present invention.
Figure 15B:
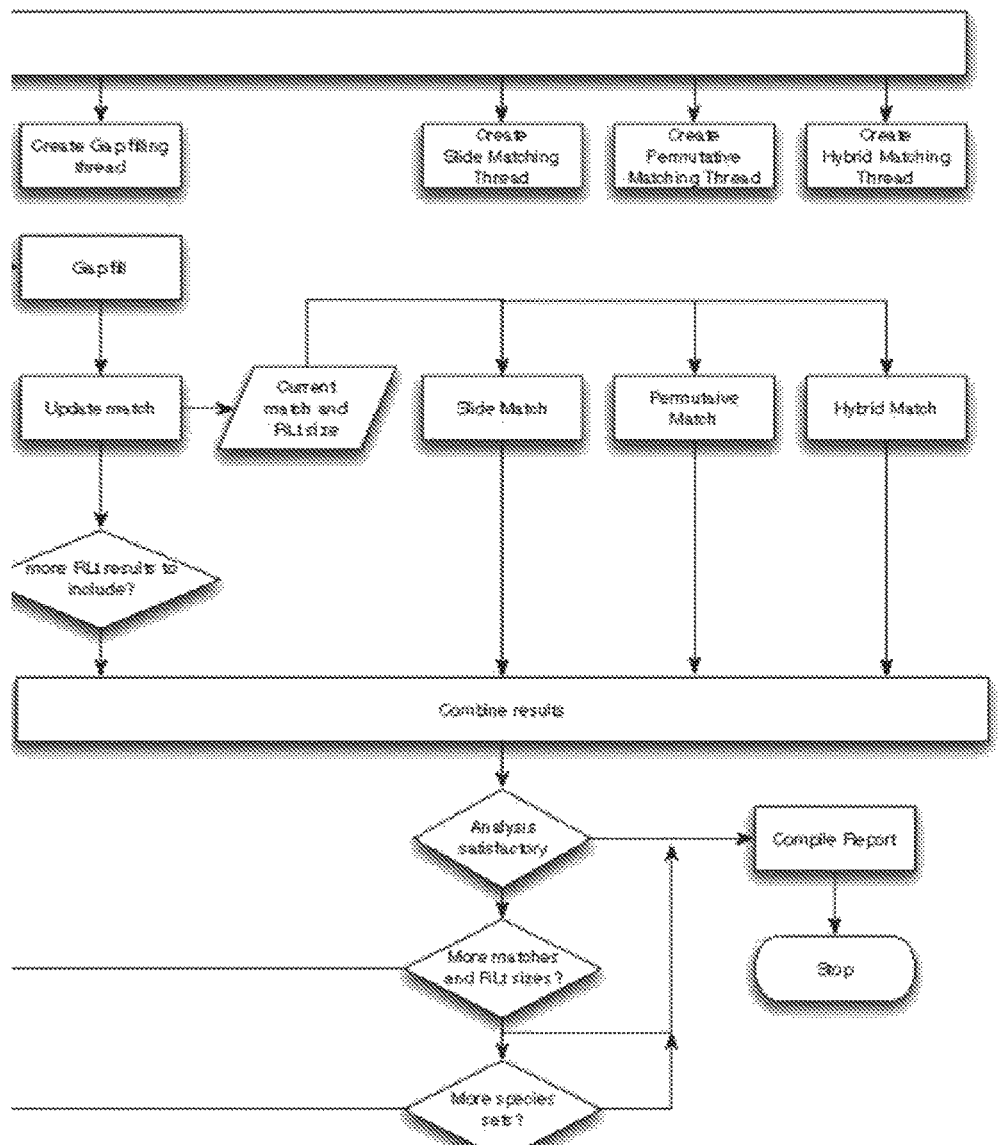

In an exemplary implementation of the method, apparatus and system described herein six threads can be created a first at least one thread for transforming the at least one query sequence, a second at least one thread for querying the plurality of reverse lookup tables, a third at least one thread for gap filling, a fourth at least one thread for permutative matching, a fifth at least one thread for sliding matching, and a sixth at least one thread for hybrid matching, as is shown in FIGS. 15A and 15B. It should be appreciated that the fourth at least one thread, the fifth at least one thread, and the sixth at least one threads are optional, depending on the application.

The cascade happens as follows. First, the thread manager initializes the first at least one thread for transforming the at least one query sequence. Once one the at least one query sequence has been transformed into the sets of consecutive non-overlapping query sequence segments, the set is put into shared memory for the second at least one thread for querying the plurality of reverse lookup tables to access, and the first at least one thread continues transforming each of the at least one query sequences into consecutive non-overlapping query sequence segments and adding sets to the shared memory. Upon seeing an available set of transformed consecutive non-overlapping query sequence segments the second at least one thread formulates RLt queries, submits the queries then sorts the results based upon species and RLt segment size, and stores the results into shared memory between the second at least one thread, and the third at least one thread for gap filling.

The third at least one thread for gap filling accesses the shared memory between the second at least one thread and the third at least one thread to update and gap fill based on species. It should be appreciated that the order is not important. For example, when there is a set of human with RLt_100 and RLt_50 results and primate with RLt_100 results, the third at least one thread will maintain the gap filling results across the RLt segment sizes, so it does not matter if the thread processes human RLt_100 then primate RLt_100 then human RLt_50. The gap filling thread maintains these results in memory shared between the gap filling thread and any matching threads in use. From the example described above, the skilled artisan will appreciate how the fourth at least one thread, the fifth at least one thread, and the sixth at least one thread can function in parallel to perform permutative matching, sliding matching, and hybrid matching in parallel with the first, the second and third at least one thread.

Example 4—Comparison to SSAHA

This Example describes how the method, apparatus and system described herein differs compared to SSAHA with respect to preprocessing, querying, processing, followed by a comparison of the run times demonstrating how the method, apparatus, and system described herein perform surprisingly and unexpectedly faster than SSAHA.

Preprocessing

The SSAHA algorithm builds a hash table from consecutive segments of the reference sequences, e.g. with reference sequence ABCDEFGH the SSAHA algorithm creates the following sequence segments: AB, CD, EF, GH. The method, apparatus, and system described herein builds the RLTs by transforming reference sequences into sets of consecutive overlapping segments, e.g. the method, apparatus and system described herein transform the above reference sequence ABCDEFGH into the following segments having a size k of 2: AB, BC, CD, DE, EF, FG, and GH.

Another difference is the SSAHA algorithms build the hash table and store it in active memory (RAM) every time the algorithms are run, meaning the preprocessing step is considered part of the matching algorithm. The method, apparatus, and system described herein however separate the preprocessing step and the matching algorithms. This is achieved by storing the results of the preprocessing step on hard drives (and/or SSDs) usually inside a database, but not limited to a database. The RLts are created and updated independent of the matching algorithms, allowing the matching algorithms to run without the preprocessing step. SSAHA contemplates the possibility of moving the hash tables from RAM to storage for use again in the future, but this future use would again be from RAM.

Querying

The SSAHA algorithm breaks the query sequence to search for into segments step-wise while the method, apparatus, and system described herein transforms the at least one query sequence into consecutive non-overlapping segments. For example, to search for ABCDEFGH, SSAHA would create: AB, BC, CD, DE, etc., whereas the method, apparatus, and system described herein create AB, CD, EF, GH, which increases time and resources preprocessing to achieve a faster matching time. Given a length L of a sequence to search for, and a tuple size k, the SSAHA algorithms submit L−k+1 queries in contrast to the method, apparatus, and system described herein which submit L/k queries. It is easy to show that for integer k>1, L/k is always less than L−k+1, and here L and k have to be integers of at least a value of 1. More so as L increases L/k becomes much less than L−k+1, e.g. a human genome with L=3.2 billion and k=10. The SSAHA algorithm would require 3,199,999,990 queries while the method, apparatus, and system described herein only requires 320 million. This is further reduced by the use of multiple RLts each with a different reference sequence segment size k, use of RLt_100 reduce the number of queries to 32 million while SSAHA would still require 3,199,999,900 queries. Similarly, using two RLts of size 10 and 100, require 320 million+32 million=352 million queries, which is still an order of magnitude fewer than SSAHA, resulting in a significantly and unexpectedly shorter processing time.

Processing

Here the two methods diverge significantly. SSAHA's authors note that "It is easy to see that the SSAHA algorithm will under no circumstances detect a match of less than k consecutive matching base pairs between match and subject, and almost as easy to see we require 2k−1 consecutive matching bases to guarantee that the algorithm will register a hit at some point in the matching region. (in the search sensitivity on page 1728). In contrast, the method, apparatus, and system described herein uses multiple RLts, permutative matching, and slide matching. Slide matching allows for gaps of any size to be filled regardless of the smallest RLt segment size, without order of magnitude computational costs. The SSAHA authors suggest one substitution of a −k-tuple but this comes with a ten-fold increase CPU time therefore large permutative matching using SSAHA would have high computational costs, but slide matching described herein is minimal. Slide matching on a gap often, at most requires 10 additional queries, and exactly identifies any mutations. This is vastly different then guessing one substitution at a cost of a 10 fold increase in CPU time.

Further differences are the use of multiple RLts with decreasing segment sizes to quickly resolve gaps. As the results from the previous RLt query are being processed, the next (in decreasing order) RLt is queried, allowing for a cascade style parallelization schema, further reducing overall CPU time. In addition to that the use of permutative matching, slide matching, or the hybrid combination further increase the matching ability.

Run Times

The SSAHA paper includes table 3 with hashing and searching times for the SSAHA algorithm. Three columns are included, 90%, 95%, and 100%. The percentages indicate what portion of the hash table is retained. Meaning after creating the hash table, the table is trimmed to 90% or 95% of its original-k-tuples. The method, apparatus, and system described herein do not trim the reference sequences at all, so the correct comparison is the 100% column. The results in Table 10 below only indicate the difference by inverting the consecutive and step wise sequence segmenting, as the multiple RLt difference affects accuracy as well, though overall performance is still improved with the multiple RLt setup and permutative/slide/hybrid matching.

TABLE 10

| k | SSAHA | Invention |
|---|---|---|
| 10 | 389.5 s | 115 seconds |
| 50 | N/A | .5 seconds |
| 100 | N/A | 0.1 seconds |

As shown in Table 10, ignoring the cascading parallelization schema and running the three k sizes in sequence is still surprisingly and unexpectedly orders of magnitude faster than SSAHA.

Example 5—Mutation Analysis to Detect a BRCA1 SNP

BRCA1 is a human tumor suppressor gene, and SNPs in this gene are known to cause different levels of risk for breast cancer. One of these SNPs is Rs16942, located at position 43091983 on human chromosome 17. BRCA1 is comprised of locations 43044295 to 43125483.

As a query sequence I took locations 43044295 to 43125483 of human chromosome 1, and changed position 43091983 from G to T. Beginning with RLt_100 from the HG38NTchr17 (a computer database environment constructed from human genome reconstruction 38), a two continuous sequences were found, from 43044295 to 43091894 and then from 43091995 to 43125495, indicating a gap between 43091894 and 43091995.

Next creating two queries with locations 43091894 through 43091945 and 43091946 through 43091995 and querying against RLt_50, the first gap is filled, leaving the gap from 43091946 to 43091995.

Building ten queries of size ten from the gap 43091946 to 43091995 and querying against RLt_10 results in matches that fill the first 3 size ten gaps, aka 43091946 to 43091975, and the last ten segment gap, 43091986 to 43091995, leaving a gap from 43091976 to 43091985.

Table 11 below lists the subject gap with the nucleotide difference between the query sequence and reference sequence italicized.

TABLE 11

| | |
|---|---|
| Query sequence: | GAAAGGATAG (SEQ ID NO: 3) |
| Reference: | GAAAGGAGAG (SEQ ID NO: 4) |

Performing a slide matching algorithm results in generation of four queries, which are listed in Table 12 below.

TABLE 12

| | |
|---|---|
| Query A | last 4 nucleotides are GAAA (the first six overlapping before the gap) |
| Query B | last 6 nucleotides are GAAAGG (the first four overlapping before the gap) |
| Query C | first 4 nucleotides are ATAG (last six overlapping after the gap) |
| Query D | first 6 nucleotides are GGATAG (last four overlapping after the gap) |

The results from these queries will fill the gap from 43091976 to 4309181, leaving the result shown in Table 13 below.

TABLE 13

| | |
|---|---|
| Query: | ATAG |
| Reference: | AGAG |

Another round of slide matching is performed by creating two new queries E and F, which are shown in Table 14 below.

TABLE 14

| |
|---|
| Query E last 2 nucleotides are AT (the first 8 overlapping before the gap) |
| Query F first 2 nucleotides are AG (the last 8 overlapping after the gap) |

The results of this query fill the gap from 4309184 to 4309185, leaving only the gap at locations 4309183 to 4309184.

Now permutative matching generates all possibilities of the sequence shown in Table 15 below.

TABLE 15

| |
|---|
| GAAAGGNNAG (SEQ ID NO: 6) |

In the sequence shown in Table 15, N is one of A, T, C, G, but in this case do not generate the combination AT (as it has already been found not to match). After formulation generate queries for each of these sequences, and submit the queries. The only filling result is GAAAGGAGAG (SEQ ID NO: 4) and comparison to the original query sequence GAAAGGATAG (SEQ ID NO: 3) indicates the SNP, which is italicized in the eighth nucleotide G in SEQ ID NO: 4. Accordingly, the method and system described herein can be used to identify discrete differences in protein and nucleotide sequences, such as inserts, deletions, and mutations, e.g., SNPs.

Example 6—Comparison to BLAST

To compare the method and system described herein to the BLAST algorithms the BLAST package was downloaded from the NCBI website and installed on the same machine as the method and system described herein. For a proper comparison the example query sequence that comes with BLAST was added to the computer database environment. This query sequence is shown in FIG. 16 in FASTA format as SEQ ID NO: 7.

One initial difference is the reference database that comes with BLAST, the refseq_rna.00 database has a size of 1.5 Gigabytes, while the computer database environment used in this Example is 185 Gigabytes.

Running the exact example query sequence provided by BLAST resulted in an exact match by both BLAST and the present invention, with the run times shown in Table 16 below.

TABLE 16

| |
|---|
| BLAST: 11.296 seconds |
| Method of the present invention: 0.25 seconds |

The query sequence has a length of 2663 nucleotides. The first queries performed by the method of the present invention were against RLt_100 and returned continuous matches from position 1 through 2599 of SEQ ID NO: 7. The remaining 2600 through 2663 nucleotides are not yet matched. Next the RLt_50 queries are formed for positions 2600-2649 of SEQ ID NO: 7 and returned a match to fill that gap and extend the match to positions 1 through 2649 of SEQ ID NO: 7. One query was then formed for nucleotides 2650-2659 of SEQ ID NO: 7 and submitted to RLt_10, which provided a match to fill that gap.

The remaining gap, 2660-2663, being less than a size of 10 is first attempted by a slide match. A query is formed from the nucleotides at positions 2654-2663, and submitted against RLt_10, which in this case returns a match. For a better test I altered the first three nucleotides of SEQ ID NO: 7 and tested each system. In the case of BLAST the runtime was roughly the same at 12.4 seconds. BLAST reported a different score, the initial BLAST run returned a score of 4758 and the second run returned a score of 4753. The method of the present invention completed the query in 0.27 seconds and proceeded as above with the exception of the first 100 nucleotides. After the RLt_100 query there will be a gap from 1-99 (the new gap), and 2600-2663 (the same gap as above and resolved the same way). The new gap was resolved analogous to the 2600-2663 gap, querying against RLt_50 will fill 50-99, then querying RLt_10 will fill 10-49, leaving an unresolved gap from 1-9.

At this point slide matching created a query from positions 5-14 and submitted the query to RLt_10, which returned a match to reduce the gap to 1-4. The next query was formed from positions 3-12, submitted to RLt_10, and this result returned no matches that would fill the gap. "Sliding to the right" a query was formed from positions 4-13, and this query returned a result that reduced the gap to positions 1-3. Next permutative matching generated 27 queries (every possible combination of NNN followed by the nucleotides from position 4-9, except for the nucleotides at positions 1, 2, and 3 in the original query sequence) and submitted them to RLt_10. One result filled the gap, and comparing this result to the original query sequence revealed the difference.

Example 7—Virus Homology

This Example demonstrates the ability of the method and system described herein to match homologous species. As a homology test, the at least one query sequence comprising a protein sequence of SEQ ID NO: 8 shown in FIG. 17 (Maize Iranian mosaic virus), underwent a species identification to test the differentiation abilities of the system and method described herein. The following description omits the gap filling steps, as they will be apparent to the skilled artisan based on the present disclosure. SEQ ID NO: 8 (i.e., the at least one query sequence) has a length L of 1926 amino acid residues, as shown in FIG. 17.

Initially, the SEQ ID NO: 8 was transformed into a set of L/100, and queries against RLt_100. Two species were gap filled from 1-1919: Maize Iranian mosaic virus UNKNOWN-NC_011542 and Maize Iranian mosaic virus UNKNOWN-DQ186554. Moving onto RLt_50, no new species were identified and no gaps in the two species from the RLt_100 results were filled. Moving onto RLt_10, many new species were identified, and no gaps were filled on the original two species. Those of minimal interest are listed below in Table, but not discussed in detail herein. For simplicity, the new species are listed in Table 17 below in order of interest followed by the gaps they had filled.

TABLE 17

| Species | Gaps Filled |
|---|---|
| Taro vein chlorosis virus UNKNOWN-AY674964 and Taro vein chlorosis virus UNKNOWN-NC_006942 | 39-48, 289-298, 458-467, 528-547, 558-567, 588-607, 678-687, 708-717, 758-777, 788-807, 808-817, 1018-1037, 1158-1167, 1218-1227, 1238-1257, 1268-1277, 1388-1397, 1488-1497 |
| Maize mosaic virus UNKNOWN--AY618418 and Maize mosaic virus UNKNOWN-NC_005975 | 38-47, 288-297, 457-466, 527-536, 557-576, 677-686, 697-716, 757-786, 807-816, 1037-1046, 1147-1166, 1227-1246, 1267-1276 |
| Cynodon rhabdovirus RLL-2008 UNKNOWN-EU650683 | 70-79, 100-119, 140-169, 190-199, 210-219 |
| Taro vein chlorosis virus TMo1-1 | 56-65, 86-95, 136-145, 176-185 |

Notably, at this point slide matching could be used to identify differences in the non-Maize Iranian mosaic virus sequences (slide matching on the Maize Iranian mosaic virus fills the remaining gap at positions 1920-1926) but for the point of species identification it is not needed. Massah et al. ("Analysis of nucleotide sequence of Iranian maize mosaic virus confirms its identity as a distinct nucleorhabdovirus," 2008; 153(6):1041-7) present data on homologies between the Maize Iranian mosaic virus and the Taro vein chlorosis virus and the group of rhabdoviruses (to which both the Cynodon rhabdovirus and the Taro vein chlorosis virus belong), as the results have shown. It should also be noted there are more rhabdoviruses listed below in Table 18 and Table 19 in the species of less interest.

TABLE 18

Species with two segment matches from RLt_10

Vesicular stomatitis Indiana virus
Nucleorhabdovirus SR/Kadapa Kadapa
Nucleorhabdovirus SR/Tirupati Tirupati
Nucleorhabdovirus SR/Kurnool Kurnool
Nucleorhabdovirus SR/Kurnool sorghum---Kurnool

TABLE 19

Species with one segment match from RLt_10

Soybean cyst nematode associated northern cereal mosaic virus
Eggplant mottled dwarf virus EG1035

TABLE 19-continued

Species with one segment match from RLt_10

Eggplant mottled dwarf virus UNKNOWN---KF410949
Eggplant mottled dwarf virus Agapanthus
Vesicular stomatitis virus UNKNOWN---X00939
Vesicular stomatitis Indiana virus UNKNOWN---NC_001560

Accordingly, the method and system described herein can be used to identify homologous species. In some implementations, the method and system can be used to identify homologous proteins. In some implementations, the method and system can be used to identify homologous viruses. In some implementations, the method and system can be used to identify homologous yeast. In some implementations, the method and system can be used to identify homologous mammals. In some implementations, the method and system can be used to identify related ancestors. In some implementations, the method and system can be used to identify homologous bacteria.

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the present invention, and exclusive use of all modifications that come within the scope of the appended claims is reserved. Within this specification embodiments have been described in a way which enables a clear and concise specification to be written, but it is intended and will be appreciated that embodiments may be variously combined or separated without parting from the invention. It is intended that the present invention be limited only to the extent required by the appended claims and the applicable rules of law.

It is also to be understood that the following claims are to cover all generic and specific features of the invention described herein, and all statements of the scope of the invention which, as a matter of language, might be said to fall there between.

What is claimed is:

1. A computer-implemented method, comprising:
   a) receiving, via a data processing system, genomic data comprising a plurality of reference sequences;
   b) constructing, via the data processing system, a forward lookup table and at least one reverse lookup table which relates reference sequence segments stored therein to reference sequences stored in the forward lookup table, wherein the reference sequence segments each comprise a first string of contiguous characters having a string length equal to a preselected positive integer k and each reference sequence comprises a second string of contiguous characters having a string length equal to a positive integer Y, wherein constructing the forward lookup table comprises transforming the genomic data into a plurality of records in the forward lookup table, wherein transforming comprises parsing the genomic data to create a reference sequence record in the forward lookup table for each reference sequence in the genomic data, wherein constructing the at least one reverse lookup table comprises:
      i) transforming each reference sequence record in the forward lookup table into a set of Y−k+1 consecutive overlapping reference sequence segments; and
      ii) storing each reference sequence segment thus transformed in a record in the at least one reverse lookup table;
   c) storing, via the data processing system, the forward lookup table and the at least one reverse lookup table in a computer database environment maintained in a non-transitory computer readable storage medium and accessible by the data processing system, wherein each record in the at least one reverse lookup table contains a reference sequence segment in which the first string of contiguous characters corresponds to k contiguous characters in the second string of contiguous characters, a pointer indicating which reference sequence record contains the reference sequence segment, and an offset (I) indicating a position at which the reference sequence segment begins in the second string of contiguous characters, wherein each reference sequence record comprises a column indicating a species of origin associated with the reference sequence;
   d) receiving, via a data processing system, a query comprising at least one query sequence comprising a third string of contiguous characters having a string length equal to L;
   e) selecting, via the data processing system, at least a first reverse lookup table of the at least one reverse lookup table that has the largest preselected positive integer k that is less than or equal to L;
   f) transforming, via the data processing system, the at least one query sequence into at least a first set of L/k consecutive non-overlapping query sequence segments by partitioning the third string of contiguous characters into L/k consecutive non-overlapping segments where k is equal to the preselected positive integer k for the at least the first reverse lookup table;
   g) querying, via the data processing system, the at least the first set of L/k consecutive non-overlapping query sequence segments against each set of Y−k+1 consecutive overlapping reference sequence segments in the at least the first reverse lookup table for matching reference and query sequence segments; and
   h) outputting, via the data processing system, at least one reference sequence that matches the at least one query sequence.

2. The method of claim 1, wherein each consecutive overlapping reference sequence segment in the set generated corresponds to the string of k contiguous characters that is obtained by moving incrementally, one character at time, along the second string of contiguous characters, starting at a first offset (I=0), and continuing to a last offset (I=Y−k).

3. The method of claim 1, wherein each consecutive overlapping reference sequence segment in the set shares k−1 contiguous characters with at least one other consecutive overlapping reference sequence segment in the set.

4. The method of claim 1, wherein the at least one reverse lookup table comprises a first reverse lookup table, and n additional reverse lookup tables where n is a positive integer greater than or equal to 2.

5. The method of 4, wherein the preselected positive integer k differs for each reverse lookup table.

6. The method of claim 5, wherein the preselected positive integer k is largest for the first reverse lookup table and the preselected positive integer k for each additional reverse lookup table is a divisor of k that decreases as the number of reverse lookup tables increases.

7. The method of claim 6, wherein the at least one reverse lookup table comprises a first reverse lookup table, and at least a second reverse lookup table.

8. The method of claim 7, wherein the preselected positive integer k for the first reverse lookup table is 100 and the preselected positive integer k for the second reverse lookup table is 50.

9. The method of claim 6, wherein the at least one reverse lookup table comprises a first reverse lookup table, a second reverse lookup table, and at least a third reverse lookup table.

10. The method of claim 9, wherein the preselected positive integer k for the first reverse lookup table is 100, the preselected positive integer k for the second reverse lookup table is 50, and the preselected positive integer k for the third reverse lookup table is 10.

11. The method of claim 1, wherein each record in the forward lookup table contains genomic sequence information selected from the group consisting of database of origin, accession number, recommended name, organism name, gene name, protein existence number, and sequence version.

12. The method of claim 1, wherein the plurality of reference sequences are selected from the group consisting of nucleic acid sequences and protein sequences.

13. The method of claim 1, wherein the non-transitory computer readable storage medium is not RAM.

14. The method of claim 1, wherein the non-transitory computer readable storage medium is selected from the group consisting of at least one hard disk drive, at least one solid state drive, and a combination of the at least one hard disk drive and the at least one solid state drive.

15. The method of claim 1, further comprising a step of reconstructing each of the matching reference sequence segments for each species of origin to create a fourth string of contiguous characters, wherein reconstructing comprises i) filtering the results of the query by species of origin to create a set of matching reference sequence segments for each species of origin, ii) sorting the set of matching reference sequence segments for each species of origin by the first offset (I1) in ascending order, and concatenating the sorted set of matching reference sequence segments for each species of origin to reconstruct each of the matching reference sequence segments into the fourth string of contiguous characters.

16. The method of claim 15, further comprising a step of determining whether any gaps remain in the fourth string of contiguous characters for each species of origin,
wherein when no gaps are determined to remain in the fourth string of contiguous characters, performing a step of outputting a report comprising the at least one reference sequence that matches the at least one query sequence, wherein the report comprises a histogram for the at least one query sequence indicating the most likely species of origin of the at least one query sequence, and
wherein when gaps are determined to remain in the fourth string of contiguous characters for a species of origin, performing a step of determining, for each gap present in the fourth string of contiguous characters, a fifth string of contiguous character gaps having a string length equal to positive integer k1, which is equal to the preselected positive integer k for the at least the first reverse lookup table, and a corresponding second offset (I2) indicating the position in the fourth string of contiguous characters at which the fifth string of contiguous character gaps begins.

17. The method of claim 16, further comprising, a step of selecting, via the data processing system, at least a second reverse lookup table in the computer database environment that has a preselected positive integer k2 that is less than the preselected positive integer k for the at least the first reverse look lookup table selected in step b), and/or
performing a sliding matching algorithm, a permutative matching algorithm, or a hybrid matching algorithm to fill the remaining gaps in the fourth string of contiguous characters and outputting a report comprising the at least one reference sequence that matches the at least one query sequence,
wherein the report is selected from the group consisting of a histogram for the at least one query sequence indicating the most likely species of origin of the at least one query sequence, an alignment of the at least one query sequence with one or more matching reference sequences in the forward lookup table, and identification of a polymorphism in the at least one query sequence selected from the group consisting of an insertion, a deletion, or a mutation.

18. The method of claim 17, further comprising, a step of transforming, via the data processing system, the at least one query sequence into at least a second set of L/k2 consecutive non-overlapping query sequence segments by partitioning the third string of contiguous characters into L/k2 consecutive non-overlapping segments where k2 is equal to the preselected positive integer k2 for the at least the second reverse lookup table selected.

19. The method of claim 18, further comprising, a step of partitioning the fifth string of contiguous character gaps into k1/k2 consecutive non-overlapping strings of contiguous character gaps each comprising a sixth string of k2 contiguous character gaps and the corresponding second offset (I2) indicating the position in the fourth string of contiguous characters at which the sixth string of k2 contiguous character gaps begins.

20. The method of claim 19, further comprising, a step of querying, via the data processing system, for each sixth string of k2 contiguous character gaps in the fourth string of contiguous characters, the at least the second set of L/k2 consecutive non-overlapping query sequence segments generated against each set of Y−k+1 consecutive overlapping reference sequence segments in the at least the second reverse lookup table selected having a first offset (I1) equal to the corresponding second offset (I2), for matching query and reference sequence segments.

21. The method of claim 20, further comprising, a step of inserting each matching reference sequence segment obtained into the gaps determined to remain in the fourth string of contiguous characters at the second offset (I2) to fill the gaps and form a seventh string of contiguous characters.

22. The method of claim 21, further comprising, a step of determining whether any gaps remain in the seventh string of contiguous characters for each species of origin,
wherein when no gaps are determined to remain in the seventh string of contiguous characters, performing a step of
outputting a report comprising the at least one reference sequence that matches the at least one query sequence, wherein the report is selected from the group consisting of a histogram for the at least one query sequence indicating the most likely species of origin of the at least one query sequence, an alignment of the at least one query sequence with one or more matching reference sequences in the forward lookup table, and identification of a polymorphism in the at least one query sequence selected from the group consisting of an insertion, a deletion, or a mutation, or
wherein when gaps are determined to remain the seventh string of contiguous characters for a species of origin, performing a step of
determining, for each gap remaining in the seventh string of contiguous characters, an eighth string of contiguous character gaps having a string length equal to positive integer k2, which is equal to the preselected positive integer k1 for the at least the second reverse lookup table, and a corresponding third offset (I3) indicating the position in the seventh string of contiguous characters at which the eighth string of contiguous character gaps begins.

23. The method of claim 22, further comprising, a step of selecting, via the data processing system, at least a third reverse lookup table in the computer database environment that has a preselected positive integer k3 that is less than the preselected positive integer k2 for the at least the second reverse look lookup table selected, and/or performing a sliding matching algorithm, a permutative matching algorithm, or a hybrid matching algorithm to fill the remaining gaps in the fourth string of contiguous characters and outputting a report comprising the at least one reference sequence that matches the at least one query sequence, wherein the report is selected from the group consisting of a histogram for the at least one query sequence indicating the most likely species of origin of the at least one query sequence, an alignment of the at least one query sequence with one or more matching reference sequences in the forward lookup table, and identification of a polymorphism in the at least one query sequence selected from the group consisting of an insertion, a deletion, or a mutation.

24. The method of claim 23, further comprising, a step of transforming, via the data processing system, the at least one query sequence into at least third second set of L/k3 consecutive non-overlapping query sequence segments by partitioning the third string of contiguous characters into L/k3 consecutive non-overlapping segments where k3 is equal to the preselected positive integer k3 for the at least the third reverse lookup table selected.

25. The method of claim 24, further comprising, a step of partitioning the eighth string of contiguous character gaps into k2/k3 consecutive non-overlapping strings of contiguous character gaps each comprising a ninth string of k3 contiguous character gaps and the corresponding third offset (I3) indicating the position in the seventh string of contiguous characters at which each ninth string of k3 contiguous character gaps begins.

26. The method of claim 25, further comprising, a step of querying, via the data processing system, for each ninth string of k3 contiguous character gaps in the seventh string of contiguous characters, the at least the third set of L/k3 consecutive non-overlapping query sequence segments generated against each set of Y−k+1 consecutive overlapping reference sequence segments in the at least the third reverse lookup table selected having a first offset (I1) equal to the corresponding third offset (I3), for matching query and reference sequence segments.

27. The method of claim 26, further comprising, a step of inserting each matching reference sequence segment obtained into the gaps determined to remain in the seventh string of contiguous characters at the third offset (I3) to fill gaps and form a tenth string of contiguous characters.

28. The method of claim 27, further comprising, a step of determining whether any gaps remain in the tenth string of contiguous characters for each species of origin, wherein when no gaps are determined to remain in the tenth string of contiguous characters, performing a step of outputting a report comprising the at least one reference sequence that matches the at least one query sequence, wherein the report is selected from the group consisting of a histogram for the at least one query sequence indicating the most likely species of origin of the at least one query sequence, an alignment of the at least one query sequence with one or more matching reference sequences in the forward lookup table, and identification of a polymorphism in the at least one query sequence selected from the group consisting of an insertion, a deletion, or a mutation; and wherein when gaps are determined to remain in the tenth string of contiguous characters, performing a step of determining, for each gap remaining in the tenth string of contiguous characters, an eleventh string of contiguous character gaps having a string length equal to positive integer k4, which is equal to the preselected positive integer k3 for the at least the third reverse lookup table, and a corresponding fourth offset (I4) indicating the position in the tenth string of contiguous characters at which the eleventh string of contiguous character gaps begins.

29. The method of claim 28, further comprising a step of performing a sliding matching algorithm, a permutative matching algorithm, or a hybrid matching algorithm to fill the remaining gaps in the fourth string of contiguous characters, and outputting a report comprising the at least one reference sequence that matches the at least one query sequence, wherein the report is selected from the group consisting of a histogram for the at least one query sequence indicating the most likely species of origin of the at least one query sequence, an alignment of the at least one query sequence with one or more matching reference sequences in the forward lookup table, and identification of a polymorphism in the at least one query sequence selected from the group consisting of an insertion, a deletion, or a mutation.

30. The method of claim 29, wherein the sliding matching algorithm comprises determining a gap length G and offset K for each gap remaining in the reconstructed sequence, transforming each gap having length G into two consecutive non-overlapping segments comprising a first overlapping segment comprising an overlapping portion beginning at offset $K=K-\frac{1}{2}G$ and a gap portion beginning at offset K and a second overlapping segment comprising a gap portion beginning at offset $K=K+\frac{1}{2}G$ and an overlapping portion beginning at offset $K=K+G$, transforming the at least one query sequence into two query sequence segments comprising a first query sequence segment comprising G contiguous characters beginning at an offset I corresponding to the offset K of the overlapping portion of the first overlapping segment and a second query sequence segment comprising G contiguous characters beginning at an offset I corresponding to the offset K of the gap portion of the second overlapping segment, querying the first and second query sequences against the reference sequence in the forward lookup table for each species and inserting matching query sequence characters and reference sequence characters into a reconstructed sequence to reduce any gaps remaining in the sequence after gap filling.

31. The method of claim 29, wherein the permutative matching algorithm comprises generating all possible characters available to fill the gaps and querying each of the possible characters at each position in the gap against the reverse lookup table comprising a preselected positive integer k that is equal to the gap length.

* * * * *

SEQUENCE LISTING

```
<160> NUMBER OF SEQ ID NOS: 8

<210> SEQ ID NO 1
<211> LENGTH: 47
<212> TYPE: PRT
<213> ORGANISM: Artificial
<220> FEATURE:
<223> OTHER INFORMATION: outer capsid VP4 (Rotavirus A F45)

<400> SEQUENCE: 1

Met Ala Ser Pro Phe Tyr Arg Gln Leu Leu Thr Asn Ser Tyr Ser Val
1               5                   10                  15

Asp Leu His Asp Glu Ile Glu Gln Ile Gly Ser Glu Lys Thr Gln Asn
            20                  25                  30

Val Thr Val Asn Pro Gly Pro Phe Ala Gln Thr Arg Tyr Ala Pro
        35                  40                  45

<210> SEQ ID NO 2
<211> LENGTH: 10
<212> TYPE: PRT
<213> ORGANISM: Artificial
<220> FEATURE:
<223> OTHER INFORMATION: outer capsid VP4 (Rotavirus A F45)

<400> SEQUENCE: 2

Met Ala Ser Pro Phe Tyr Arg Gln Leu Leu
1               5                   10

<210> SEQ ID NO 3
<211> LENGTH: 10
<212> TYPE: DNA
<213> ORGANISM: Artificial
<220> FEATURE:
<223> OTHER INFORMATION: query sequence segment

<400> SEQUENCE: 3
gaaaggatag                                                            10

<210> SEQ ID NO 4
<211> LENGTH: 10
<212> TYPE: DNA
<213> ORGANISM: Artificial
<220> FEATURE:
<223> OTHER INFORMATION: reference sequence segment

<400> SEQUENCE: 4
gaaaggagag                                                            10

<210> SEQ ID NO 5

<400> SEQUENCE: 5

000

<210> SEQ ID NO 6
<211> LENGTH: 10
<212> TYPE: DNA
<213> ORGANISM: Artificial
<220> FEATURE:
<223> OTHER INFORMATION: permutatively matched sequence
<220> FEATURE:
<221> NAME/KEY: misc_feature
<222> LOCATION: (7)..(8)
<223> OTHER INFORMATION: n is a, c, g, or t

<400> SEQUENCE: 6
```
gaaaggnnag                                                            10

<210> SEQ ID NO 7
<211> LENGTH: 2662
<212> TYPE: DNA
<213> ORGANISM: Homo sapiens

<400> SEQUENCE: 7

| | | | | | |
|---|---|---|---|---|---|
| gaagagaccc | agcaacccac | agagttgaga | aatttgactg | gcattcaagc | tgtccaatca | 60 |
| atagctgccg | ctgaagggtg | gggctggatg | gcgtaagcta | cagctgaagg | aagaacgtga | 120 |
| gcacgaggca | ctgaggtgat | tggctgaagg | cacttccgtt | gagcatctag | acgtttcctt | 180 |
| ggctcttctg | gcgccaaaat | gtcgttcgtg | gcaggggtta | ttcggcggct | ggacgagaca | 240 |
| gtggtgaacc | gcatcgcggc | gggggaagtt | atccagcggc | cagctaatgc | tatcaaagag | 300 |
| atgattgaga | actgtttaga | tgcaaaatcc | acaagtattc | aagtgattgt | taaagaggga | 360 |
| ggcctgaagt | tgattcagat | ccaagacaat | ggcaccggga | tcaggaaaga | agatctggat | 420 |
| attgtatgtg | aaaggttcac | tactagtaaa | ctgcagtcct | ttgaggattt | agccagtatt | 480 |
| tctacctatg | gctttcgagg | tgaggctttg | gccagcataa | gccatgtggc | tcatgttact | 540 |
| attacaacga | aaacagctga | tggaaagtgt | gcatacagag | caagttactc | agatggaaaa | 600 |
| ctgaaagccc | ctcctaaacc | atgtgctggc | aatcaaggga | cccagatcac | ggtggaggac | 660 |
| ctttttttaca | acatagccac | gaggagaaaa | gctttaaaaa | atccaagtga | agaatatggg | 720 |
| aaaattttgg | aagttgttgg | caggtattca | gtacacaatg | caggcattag | tttctcagtt | 780 |
| aaaaaacaag | gagagacagt | agctgatgtt | aggacactac | ccaatgcctc | aaccgtggac | 840 |
| aatattcgct | ccatctttgg | aaatgctgtt | agtcgagaac | tgatagaaat | tggatgtgag | 900 |
| gataaaaccc | tagccttcaa | aatgaatggt | tacatatcca | atgcaaacta | ctcagtgaag | 960 |
| aagtgcatct | tcttactctt | catcaaccat | cgtctggtag | aatcaacttc | cttgagaaaa | 1020 |
| gccatagaaa | cagtgtatgc | agcctatttg | cccaaaaaca | cacccattt | cctgtacctc | 1080 |
| agtttagaaa | tcagtcccca | gaatgtggat | gttaatgtgc | accccacaaa | gcatgaagtt | 1140 |
| cacttcctgc | acgaggagag | catcctggag | cgggtgcagc | agcacatcga | gagcaagctc | 1200 |
| ctgggctcca | attcctccag | gatgtacttc | acccagactt | tgctaccagg | acttgctggc | 1260 |
| ccctctgggg | agatggttaa | atccacaaca | agtctgacct | cgtcttctac | ttctggaagt | 1320 |
| agtgataagg | tctatgccca | ccagatggtt | cgtacagatt | cccgggaaca | gaagcttgat | 1380 |
| gcatttctgc | agcctctgag | caaacccctg | tccagtcagc | cccaggccat | tgtcacagag | 1440 |
| gataagacag | atatttctag | tggcagggct | aggcagcaag | atgaggagat | gcttgaactc | 1500 |
| ccagcccctg | ctgaagtggc | tgccaaaaat | cagagcttgg | aggggatac | aacaaagggg | 1560 |
| acttcagaaa | tgtcagagaa | gagaggacct | acttccagca | accccagaaa | gagacatcgg | 1620 |
| gaagattctg | atgtggaaat | ggtggaagat | gattcccgaa | aggaaatgac | tgcagcttgt | 1680 |
| accccccgga | gaaggatcat | taacctcact | agtgttttga | gtctccagga | agaaattaat | 1740 |
| gagcagggac | atgaggttct | ccgggagatg | ttgcataacc | actccttcgt | gggctgtgtg | 1800 |
| aatcctcagt | gggccttggc | acagcatcaa | accaagttat | accttctcaa | caccaccaag | 1860 |
| cttagtgaag | aactgttcta | ccagatactc | atttatgatt | ttgccaattt | tggtgttctc | 1920 |
| aggttatcgg | agccagcacc | gctctttgac | cttgccatgc | ttgccttaga | tagtccagag | 1980 |
| agtggctgga | cagaggaaga | tggtcccaaa | gaaggacttg | ctgaatacat | tgttgagttt | 2040 |
| ctgaagaaga | aggctgagat | gcttgcagac | tatttctctt | tggaaattga | tgaggaaggg | 2100 |

```
aacctgattg gattacccct tctgattgac aactatgtgc cccctttgga gggactgcct    2160
atcttcattc ttcgactagc cactgaggtg aattgggacg aagaaaagga atgttttgaa    2220
agcctcagta aagaatgcgc tatgttctat tccatccgga agcagtacat atctgaggag    2280
tcgaccctct caggccagca gagtgaagtg cctggctcca ttccaaactc ctggaagtgg    2340
actgtggaac acattgtcta taaagccttg cgctcacaca ttctgcctcc taaacatttc    2400
acagaagatg gaaatatcct gcagcttgct aacctgcctg atctatacaa agtctttgag    2460
aggtgttaaa tatggttatt tatgcactgt gggatgtgtt cttctttctc tgtattccga    2520
tacaaagtgt tgtatcaaag tgtgatatac aaagtgtacc aacataagtg ttggtagcac    2580
ttaagactta tacttgcctt ctgatagtat tcctttatac acagtggatt gattataaat    2640
aaatagatgt gtcttaacat aa    2662
```

<210> SEQ ID NO 8
<211> LENGTH: 1926
<212> TYPE: PRT
<213> ORGANISM: Artificial
<220> FEATURE:
<223> OTHER INFORMATION: Maize Iranian mosaic virus query sequence

<400> SEQUENCE: 8

```
Met Asp Thr Glu Glu Pro Ile Ser Gln Asp Asp Leu Asp Ala Leu Asp
1               5                  10                  15

Gly Leu Leu Gln Ala Glu Glu Gly Glu Glu Thr Thr Asp Glu Asp
            20                  25                  30

Gly Gly Ser Met Leu Gly Gly Met Gly Asp Tyr His Leu Lys Ser Ala
        35                  40                  45

Leu Arg Gly Phe Asp Asp Met Met Arg His Pro Ile Phe Arg Lys Glu
    50                  55                  60

Phe Glu Lys Ala Ile Val Ser Phe Asn Ile Ser His Asn Asn Met Leu
65                  70                  75                  80

Ser Gln Ile Glu Thr Met Phe Phe Met Met Asn Asp Thr Pro Ile Ile
                85                  90                  95

Pro Arg Arg Gly Met Leu Leu Gly Asp Phe Gln Gln Arg Val Val Ala
            100                 105                 110

Leu Pro His Gly Glu Asp Val Phe Asp Ile Ile His Ala Glu Ile Cys
        115                 120                 125

Val Leu His Pro His Leu Gln Leu Ser Leu Ser Val Ser Ala Val Arg
    130                 135                 140

Asp Ile Val Arg Leu Val Met Glu Lys Val Ala Lys Asp Asp Phe Ala
145                 150                 155                 160

Ser Met Thr Trp Ala Ala Ala Ile Met Ile Lys Asn Phe Ile Pro Ala
                165                 170                 175

Trp Lys Lys Arg Gly Lys Gln Leu Leu Asp Trp Pro Ser Val Asn Phe
            180                 185                 190

Asp Ala Glu Thr Gly Tyr Val Arg Met Val Leu Glu Gly Asp Leu Ile
        195                 200                 205

Ile Tyr Met Gly Ser Asp Ile Cys Ile Ile Glu Lys Tyr Pro Asn Val
    210                 215                 220

Arg Trp Ala Pro Val Ser Tyr Ile Leu Asn Gly Ala Asp Lys Leu Ala
225                 230                 235                 240

Glu Arg Tyr Asn Val Arg Leu Tyr Ser Gly Ile Cys Asp His Leu Ser
                245                 250                 255
```

```
Ile Pro Asp Arg Val Ser Leu Asp Leu Asn Arg Ile Ile Asp Val
            260                 265                 270

Gly Asp Arg Cys Leu Asp Glu Leu Gly Asn Glu Gly Tyr Ala Val Ile
        275                 280                 285

Ala Ser Tyr Glu Ala Leu Leu Ala Gly Ile Ile Gln Met Arg Asp Asp
    290                 295                 300

Asp Lys Leu Ile Ala Asp Val Gly Leu Leu Arg Arg Thr Thr Leu Glu
305                 310                 315                 320

Glu Phe Ala Asn Thr Arg Gly Gly Lys Tyr Leu Ala Glu Trp Asp Arg
                325                 330                 335

Met Phe Leu Asn Met Ser Ala Glu Gln Val Ala Cys Ala His Gly Leu
            340                 345                 350

Tyr Arg Ile Trp Gly Leu Pro Val Val Asp Ile Leu Gly Gly Ile Leu
        355                 360                 365

Lys Met Lys Glu Val Ala Ser Val Lys Lys Cys Pro Asp Glu Ser Val
370                 375                 380

Leu Lys Asp Ile Gly Arg Gln Phe Lys Glu Met Phe Phe Thr Ala Tyr
385                 390                 395                 400

His Arg Leu His Lys His Tyr Pro Lys Ser Asp Ile Leu Pro Gly Phe
                405                 410                 415

Pro Lys Lys Ser Tyr Ile Ile Glu Ala Leu Gln Asn Asn Thr Ser Ile
            420                 425                 430

Asn Val Lys Val Val Gly Tyr Val Phe Leu Asp Trp Asp Tyr Val Glu
        435                 440                 445

Leu Lys Gln Asn Phe Glu Val Pro Tyr Ser Trp Asn Leu Val His Asn
450                 455                 460

Leu Lys Asp Lys Ala Ile Ser Pro Thr Arg Lys Glu Ile Tyr His Thr
465                 470                 475                 480

Leu Val Arg Arg Asn Thr Ile Phe Gly Ala Glu Asn Arg Arg Gly Ile
                485                 490                 495

Leu Lys Ser Leu Lys Met Glu Thr Val Gln Leu Arg Glu Phe Leu Gln
            500                 505                 510

Ser Val Asn Asp Asp Gly Leu Pro Asp Glu Asp Arg Ile Ile Gly Val
        515                 520                 525

Tyr Pro Lys Glu Arg Glu Leu Lys Ile Lys Ala Arg Leu Phe Ser Leu
530                 535                 540

Met Ser Phe Lys Leu Arg Leu Tyr Ile Val Ser Thr Glu Ala Leu Leu
545                 550                 555                 560

Gly Asp Lys Ile Leu Lys Tyr Phe Pro Gln Ile Thr Met Ser Leu Asp
                565                 570                 575

Met Leu Thr Met Ile Lys Lys Met Phe Arg Val Ser Ser Gln Thr Thr
            580                 585                 590

Arg Gly Asp Asp Ser Val Thr Val Ile Phe Asn Leu Asp Phe Val Lys
        595                 600                 605

Trp Asn Leu Gln Met Arg Lys Asn Ile Cys His Pro Val Phe Arg Gln
610                 615                 620

Leu Gly Glu Leu Phe Gly Met Lys Asp Leu Tyr Asp Arg Thr His Asp
625                 630                 635                 640

Leu Phe Arg Thr Ser Thr Ile Tyr Leu Cys Ser Gly Glu Gly Glu Leu
                645                 650                 655

Thr Ala Asp Pro Glu Tyr Gly Val Asn Pro Asn Gly Ile Trp Ala Trp
            660                 665                 670

Thr Gly Asp Glu Ser Gly Lys Glu Gly Leu Arg Gln Lys Gly Trp Thr
```

-continued

```
            675                 680                 685
Ile Leu Thr Val Val Ala Ile Met Leu Ile Ala Lys Arg His Asn Val
            690                 695                 700
Asp Val Ser Leu Met Gly Gly Asp Asn Gln Val Leu Gly Ile Thr
705                 710                 715                 720
Ile Ser Gly Met Val Arg Asp Ser Met Asn Gly Leu Thr Asp Glu Ser
                    725                 730                 735
Lys Gly Val Ala Ser Lys Ile Ile Lys Ser Phe Thr Asp Asp Leu Leu
                740                 745                 750
Thr Thr Phe Gln Asp Leu Gly Leu Pro Leu Lys Ala Ser Glu Thr Trp
            755                 760                 765
Val Ser Asp Ser Leu Phe Met Tyr Asn Lys His Met Phe Tyr Lys Gly
            770                 775                 780
Ile Pro Leu Arg Ser Pro Leu Lys Ala Val Ser Arg Ile Phe Pro Leu
785                 790                 795                 800
Ala Asn Asp Ser Ile Met Thr Leu Asp Asn Met Ile Asn Asn Ile Ser
                805                 810                 815
Ser Gly Val Lys Ala Ala Cys Met Lys Glu Arg Asn Gly Ile Pro Leu
                820                 825                 830
Ile Phe Leu Lys Ala Leu Ser Tyr Arg Arg Ala Ala Glu Ile Val Leu
            835                 840                 845
Thr Leu His Pro Leu Val Thr Cys Phe Arg Ala Pro Ser Leu Pro Thr
            850                 855                 860
Gln Gly Ile Val Met Arg Ser Ser Lys Lys Thr Asn Val Lys Val Thr
865                 870                 875                 880
Ser Lys Gln Leu Arg Asn Tyr Phe Ala Cys Cys Leu Thr Gly Ala Ser
                885                 890                 895
Ile Met Gly Thr Pro Gly Thr Ile His Val Thr Asp Met Ile Met Arg
                900                 905                 910
Gly Phe Pro Asp Pro Leu Thr Gly His Leu Ala Phe Ile Gly Ala Leu
            915                 920                 925
Ala Thr Arg Ile Gln Ser Val His Leu Arg Ala Val Glu Lys Met
930                 935                 940
Ser His Met Ser Ile Asn Arg Ser Ile Glu Tyr Ala Lys Leu Val Glu
945                 950                 955                 960
Asp Pro Ala Ser Ile Asn His Asp Ala Pro Thr His Gly Leu Asn Glu
                965                 970                 975
Leu Arg Gln Met Ser Arg Asp Phe Leu Met Lys Thr Thr Leu Ala Thr
                980                 985                 990
Asn Pro Tyr Leu Thr Asp Leu Phe  Ser Leu Leu Asp Arg  Lys Ser Glu
            995                 1000                1005
Ser Ala  Phe Tyr Glu Gln Leu  Cys Ser Ala Glu Glu  Leu Asp Val
     1010                1015                1020
Lys Val  Leu His Glu Ile Ala  Gly Ala Thr Leu Tyr  Gly Tyr Thr
     1025                1030                1035
Asn Gly  Ile Ala Ser Arg Ile  Asp Gln Thr Arg Thr  Val Arg Ala
     1040                1045                1050
Leu Asn  Glu Asn Glu Asp Val  Met Lys Arg Met Ala  Asp Ala Glu
     1055                1060                1065
Trp Arg  Tyr Val Gly Tyr Leu  Leu Ala Arg Asp Ile  Leu Thr His
     1070                1075                1080
Asp Leu  Val Pro Asp Glu Cys  Ser Arg Val Ser Ala  Asp Arg Tyr
     1085                1090                1095
```

-continued

```
Arg Leu Tyr Ser Trp Arg Lys Pro Val Ile Gly Val Thr Val Pro
              1100            1105            1110

His Pro Ile Glu Met Cys Ser Val Thr Ser Gln Thr Arg Thr Ser
    1115            1120            1125

Tyr Met Asp Ala Val Ile Cys Trp Ser Asp Asn Val Gln Gly Asn
    1130            1135            1140

Asp Ile Tyr Thr Thr Met Gly Leu Gly Lys Ile Tyr Gln Gly Ser
    1145            1150            1155

Tyr Thr Lys Glu Arg Phe Lys Ala Thr Asp Ile Ala Ala Ala Tyr
    1160            1165            1170

Gly Asn Glu Asp Ile Leu Ser Lys Ala Val Arg Ile Gln Lys Leu
    1175            1180            1185

Ile Asn Trp Arg Tyr Asp Glu Thr Ser Asn Phe Ala Asp Ile Ile
    1190            1195            1200

Arg Leu Thr Leu Lys Ala Ile Thr Asp Ala Asp Thr Glu Gly Phe
    1205            1210            1215

His Arg Ser Lys Glu Glu Ile Lys Gly Glu Phe Asp His Arg Arg
    1220            1225            1230

Gly Ile Ser Gly Asp Ile Ser Gly Gly Ile Pro Asn Phe Leu Val
    1235            1240            1245

Thr Pro Thr Ser His Phe Ser Ser Thr Thr Ser Ser Trp Thr Ser
    1250            1255            1260

His Ser Arg Gly Gly Lys Asn Glu Asn Ile His Phe Gln Ser Val
    1265            1270            1275

Leu Ile Asn Leu Leu Tyr Arg Ala Met Val Phe Arg Gly Ser Ser
    1280            1285            1290

Leu Ser Thr Ser Pro Val Val Trp Tyr Ser Glu Glu Arg Cys Pro
    1295            1300            1305

His Cys Ile Val Glu Ile Arg Glu Pro Asp Pro Ser Arg Thr Thr
    1310            1315            1320

Pro Lys Leu Asp Lys Ile Pro Thr Ala Pro Gly Asn Pro Phe Ala
    1325            1330            1335

Phe Ile Glu Ser Ile Asn Val Lys Leu Asp Tyr His His Ile Val
    1340            1345            1350

Glu Ile His Lys Gly Asn Glu Glu Glu Asn Leu Ile Asn Ser Ser
    1355            1360            1365

Trp Asp Gly Thr Asn Ile Ser Cys Asn Gln Glu Ala Gly Leu Leu
    1370            1375            1380

Leu Phe Leu Met Val Ile Gly Ser Arg Gln Ile Ser Glu Ser Phe
    1385            1390            1395

Ile Leu Leu Met Arg Glu Arg Val Gln Ala Ser Glu Val Leu Gln
    1400            1405            1410

Met Val Ile Asn Arg Ile Thr Leu Met Arg Arg Met Gly Leu Asp
    1415            1420            1425

Lys Gln Phe Pro Val Arg Ser Thr Ser Cys Leu Asn Leu Leu Leu
    1430            1435            1440

Gly Thr Asp Gln Asn Leu Ser Arg Cys His Asp Arg Phe Gly Val
    1445            1450            1455

Glu Ile Val Ser Gly Ser Trp Glu Lys Gly Ile Gln Leu Asp Ala
    1460            1465            1470

Ser Phe Ile Tyr Arg Asp Asp Leu Ala Thr Thr Gly Asp Leu His
    1475            1480            1485
```

-continued

```
Val Asn Val Tyr Leu Gln Asn Val Pro Leu Gln Leu Ala Leu Ser
    1490                1495                1500

His Ala Ala Ser Arg Val Glu Val Gln Arg Cys Leu Glu Cys Cys
    1505                1510                1515

Ala Ile Ile Ser Asp Arg Val Ser Lys Arg Asp Ser Pro Asn His
    1520                1525                1530

Leu His Trp Arg Cys Pro Glu His Met Asp Lys Asp Phe Ser Pro
    1535                1540                1545

Thr Ile Val Arg Ile His Ser Glu Lys Leu Ile Lys Gly Glu Asn
    1550                1555                1560

Ile Ile Asp Gly His Glu Phe Ser Ile Pro Phe Ile Asp Glu Pro
    1565                1570                1575

Val Ala Leu Glu Val Ala Asp Arg Thr Glu Ala Asp Leu Asn Glu
    1580                1585                1590

Trp Ser Met Pro Ile Tyr Met Tyr Ser Ala Trp Glu Asn Ile Leu
    1595                1600                1605

Pro Gln Leu Tyr Val Thr Met Lys Ser Ala Ile Leu Tyr Thr Lys
    1610                1615                1620

Val Thr Ser Ile Ile Val Glu Asp Glu Ile Thr Leu Ile Asn Leu
    1625                1630                1635

Val Ala Arg Cys Leu Asn Asp Leu Arg Arg Ser Met Ser Ile Tyr
    1640                1645                1650

Val Leu Ser Asp Glu Phe Ser Gly Thr Glu Ile Asn Asn Lys Tyr
    1655                1660                1665

Asp Asn Met Arg Leu Leu Pro Pro Gly Ile Arg Asp Thr Ile Arg
    1670                1675                1680

Leu Tyr Glu Glu Ser Lys His Glu Val Cys Lys Glu Thr Ala Leu
    1685                1690                1695

Val Val Asn Pro Ser Ser Lys Ala Pro Ile Glu Gly Gly Ser Leu
    1700                1705                1710

His Val Ile Trp Ala Asp Asn Trp Thr Gln Val Arg Glu Thr Thr
    1715                1720                1725

Gly His Met Tyr His Thr Ser Val Arg Ile Ala Ser Gly Tyr Cys
    1730                1735                1740

Gly Ile Leu Glu Val Phe Asp Arg Glu Thr Pro Ala Leu Phe Ser
    1745                1750                1755

Leu Ala Gly Ser Val Leu Ser Trp Glu Lys Lys Pro Ile Asp His
    1760                1765                1770

Glu Arg Ala Lys Ile Gln Glu Thr Pro Ile Gln Leu Ser Arg Val
    1775                1780                1785

Leu Gly Cys Ser Arg Leu Gly Val Arg Gly Met Arg Trp Val Met
    1790                1795                1800

Trp Asp Ser Ala Leu Gly Leu Glu Arg Ile Ile Arg Thr Leu Arg
    1805                1810                1815

Ser Lys Leu Leu Ser Leu Ser Ser Asn Pro Gly Arg Ala Asp His
    1820                1825                1830

Trp Lys Arg Ala Cys Gln Lys Ile Leu Lys Thr Phe Met Ile Ser
    1835                1840                1845

Leu Tyr Ala His Val Gln Gly Asp Met Leu Glu Arg Ala Gly Ser
    1850                1855                1860

Leu Val Gly Val Arg Val His Gly Ala Leu Ser Gly Ile Thr Ala
    1865                1870                1875

Val His Asp Ala Ala Ser Glu Asn Arg Leu Gln Arg Arg Gln Tyr
```

-continued

```
              1880                1885                1890
Ile Tyr  Ile Lys Glu Asn Ser  Lys Glu Gly Pro Phe  Ile Leu Arg
    1895              1900                   1905

Asn Arg  Val Glu Arg Arg Ile  Ser Leu Met Ser Ala  Val Tyr Asp
    1910              1915                   1920

Leu Leu  Gly
    1925
```